(12) United States Patent
Hata et al.

(10) Patent No.: US 10,653,672 B2
(45) Date of Patent: May 19, 2020

(54) MYOGENESIS PROMOTOR, MUSCLE ATROPHY INHIBITOR, MEDICAL COMPOSITION AND TAZ ACTIVATOR

(71) Applicant: National University Corporation Tokyo Medical and Dental University, Tokyo (JP)

(72) Inventors: Yutaka Hata, Tokyo (JP); Hiroyuki Kagechika, Tokyo (JP); Kentaro Nakagawa, Tokyo (JP); Shigeru Ito, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 15/117,340

(22) PCT Filed: Feb. 6, 2015

(86) PCT No.: PCT/JP2015/053400
§ 371 (c)(1),
(2) Date: Aug. 8, 2016

(87) PCT Pub. No.: WO2015/119249
PCT Pub. Date: Aug. 13, 2015

(65) Prior Publication Data
US 2016/0346251 A1 Dec. 1, 2016

(30) Foreign Application Priority Data
Feb. 7, 2014 (JP) .................................. 2014-022287

(51) Int. Cl.
| A61K 31/4178 | (2006.01) |
| A61K 31/454 | (2006.01) |
| A61K 31/5377 | (2006.01) |
| A61K 31/4164 | (2006.01) |
| A61K 31/4402 | (2006.01) |

(52) U.S. Cl.
CPC ...... *A61K 31/4164* (2013.01); *A61K 31/4178* (2013.01); *A61K 31/4402* (2013.01); *A61K 31/454* (2013.01); *A61K 31/5377* (2013.01)

(58) Field of Classification Search
CPC .............. A61K 31/535; A61K 31/4164; A61K 31/4178; A61K 31/454; A61K 31/5377
USPC ..................................................... 514/235.8
See application file for complete search history.

(56) References Cited

U.S. PATENT DOCUMENTS

| 5,326,776 A | 7/1994 | Winn et al. |
| 5,968,952 A | 10/1999 | Venet et al. |
| 8,846,704 B2 | 9/2014 | Bourke et al. |

| 2007/0037752 A1 | 2/2007 | Ansorge et al. |
| 2008/0312305 A1* | 12/2008 | Bauer ............. C07D 233/88 514/398 |
| 2009/0136481 A1 | 5/2009 | Kambadur et al. |
| 2010/0305324 A1 | 12/2010 | Kim et al. |
| 2012/0296403 A1 | 11/2012 | Glass et al. |

FOREIGN PATENT DOCUMENTS

| EP | 514192 A1 | 11/1992 |
| JP | H06211845 A | 8/1994 |
| JP | H11514635 A | 12/1999 |

(Continued)

OTHER PUBLICATIONS

Yang, Molecular and Cellular Biology, vol. 34, No. 9, May 2014, p. 1607-1621.*
Shuck-Lee, Antimicrobial Agents and Chemotherapy, Sep. 2008, p. 3169-3179.*
Gewald, Monatshefte Fur Chemie, vol. 107, 1976, p. 1413-1421.*
DeVries, J. Org. Chem. vol. 39, No. 12, 1974, p. 1707-1710.*
J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*

(Continued)

*Primary Examiner* — Jeffrey S Lundgren
*Assistant Examiner* — Chris E Simmons
(74) *Attorney, Agent, or Firm* — Marshall, Gerstein & Borun LLP

(57) ABSTRACT

The invention provides a novel myogenesis promotor, a novel muscle atrophy inhibitor, a novel composition or a novel TAZ activator. The myogenesis promotor, the muscle atrophy inhibitor, the composition and the TAZ activator include a composition represented by the following Formula (I) as an active ingredient. In Formula (I), $R^1$ represents a hydrogen atom or an alkyl group; $R^2$ represents an aryl group, a heterocyclic group, an alkyl group or the like; $R^3$ represents $-NR^5R^6$ or $-N=C-R^7$; each of $R^5$ and $R^6$ independently represents a hydrogen atom, an alkyl group or the like; $R^7$ represents $-NR^{10}R^{11}$, an aryl group or a heterocyclic group; $R^8$ represents a hydrogen atom, an alkyl group or the like; $R^9$ represents a hydrogen atom, an alkyl group or the like; each of $R^{10}$ and $R^{11}$ independently represents a hydrogen atom, an alkyl group or the like; $R^4$ represents a cyano group or $-C(=O)R^{12}$; and $R^{12}$ represents an aryl group, a heterocyclic group, an alkyl group or the like.

(1)

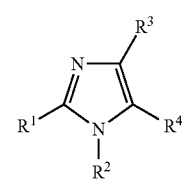

4 Claims, 16 Drawing Sheets
Specification includes a Sequence Listing.

(56) References Cited

FOREIGN PATENT DOCUMENTS

| JP | 2004/505111 A | | 2/2004 |
|---|---|---|---|
| JP | 2007-508349 | * | 4/2007 |
| JP | 2007/508349 A | | 4/2007 |
| JP | 2008/530004 A | | 8/2008 |
| JP | 2009-521429 | | 6/2009 |
| JP | 2010516788 A | | 5/2010 |
| JP | 2010-280658 | | 12/2010 |
| JP | 2013-519869 | | 5/2013 |
| WO | WO-2011/076765 A1 | | 6/2011 |

OTHER PUBLICATIONS

Gewald et al. ("4-Amino-Imidazoles by Thorpe-cyclization", Monatshefte für Chemie (1976); vol. 107:1413-1421). (Year: 1976).*
Gewald et al. ("4-Amino-Imidazoles by Thorpe-cyclization", Monatshefte für Chemie (1976); vol. 107:1413-1421). (Year: 1976). English translation.*
Yang et al., "Screening with a Novel Cell-Based Assay for TAZ Activators Identifies a Compound That Enhances Myogenesis in C2C12 Cells and Facilitates Muscle Repair in a Muscle Injury Model", Molecular and Cellular Biology, vol. 34, No. 9, May 2014, pp. 1607-1621.
Jeong et al., "TAZ as Novel Enhancer of MyoD-mediated Myogenic Differentiation", The FASEB Journal, vol. 24, Sep. 2010, pp. 3310-3320.
Jang et al., "TM-25659 Enhances Osteogenic Differentiation and Suppresses Adipogenic Differentiation by Modulating the Transcriptional co-activator TAZ", British Journal of Pharmacology, vol. 165, 2012, pp. 1584-1594.
Byun, "TAZ is required for the Osteogenic and Anti-adipogenic Activities of Kaempferol", Bone, vol. 50, 2012, pp. 364-372.
Murakami, "Transcriptional Activity of Pax3 is co-activated by TAZ", Biochemical and Biophysical Research Communications, vol. 339, 2006, pp. 533-539.
Shuck-Lee et al., "Heterocyclic Compounds That Inhibit Rev-RRE Function and Human Immunodeficiency Virus Type 1 Replication", Antimicrobial Agents and Chemotherapy, Sep. 2008, pp. 3169-3179.
Search Report and Written Opinion in International Application No. PCT/JP2015/053400 dated Apr. 14, 2015, 8 pages.
Bao et al., "Roles of Mammalian Sterile 20-like Kinase 2-dependent Phosphorylations of Mps one Binder 1B in the Activation of Nuclear Dbf2-related Kinases", Genes to Cells, vol. 14, 2009, pp. 1369-1381.
Bao et al., "A Cell-Based Assay to Screen Stimulators of the Hippo Pathway Reveals the Inhibitory Effect of Dobutamine on the YAP-dependent Gene Transcription", J. Biochem., vol. 150 (2), 2011, pp. 199-208.
Hirabayashi et al., "Threonine 74 of MOBI is a Putative Key Phosphorylation Site by MST2 to form the Scaffold to Activate Nuclear Dbf2-related Kinase 1", Oncogene, vol. 27, 2008, pp. 4281-4292.
Ikeda et al, Hippo Pathway-Dependent and -Independent Roles of RASSF6, Cell Biology, www.sciencesignaling.org, vol. 2, Issue 90 ra59, Sep. 29, 2009, 12 pages.
Gewald et al., "4-Amino-imidazoles by Thorpe-cyclization", Monatshefte Für Chemie, vol. 107, 1976, pp. 1413-1421.
Schaefer et al., "One Step Synthesis of Arylaminomethylene-cyanamides", Journal f. prakt. Chemie. Band 318, Heft 2, 1976, pp. 347-349.
Gewald et al., "Substituted 2-Alkoxy-5-amino- and -2,5-diamino-imidazoles from Oxazol-2-yliden-cyanamides", Monatshefte Für Chemie, vol. 127, 1996, pp. 313-318.
Cai et al., "Dication $C(R^1)$-$N(R^2)_2$ Synthons and Their Use in the Synthesis of Formamidines, Amidines, and α-Aminonitriles", Tetrahedron, vol. 56, 2000, pp. 8253-8262.
Schaefer et al., "One Step Synthesis of Arylaminomethylene-cyanamides", Journal for Practical Chemistry, vol. 318, No. 2, 1976, pp. 347-349 (one page—partial translation).
Verkoyen et al., "Aryl-Substituted Purines I, Synthesis of 7 Phenylguanine and of 2-Substituted 7 Arylhypoxanthines", Liebigs Annalen Der Chemie, No. 11, 1987, pp. 957-960.
Extended European Search Report in EP Application No. 15746721.8 dated Sep. 4, 2017, 10 pages.
Office Action in JP Application No. 2015-561058 dated Dec. 11, 2018, 5 pages.

* cited by examiner

Bar : 100 μm

C2C12 differentiation 72h

C2C12 differentiation 24h

Bar: 50μm

MYOGENESIS PROMOTOR, MUSCLE ATROPHY INHIBITOR, MEDICAL COMPOSITION AND TAZ ACTIVATOR

TECHNICAL FIELD

The invention relates to a myogenesis promotor, a muscle atrophy inhibitor, a medical composition and a TAZ activator.

BACKGROUND ART

Various types of diseases are caused by muscle damage or atrophy, or by muscle reduction or deficiency due to inadequate development, such as sarcopenia, steroid myopathy and muscular dystrophy. Sarcopenia is a syndrome induced by muscle reduction with aging. Development of therapeutic approaches for sarcopenia has become an important health issue for elderly people. Along with kinetic or dietary treatments, treatment and prevention by medicines are prospective means for alleviating the symptoms of sarcopenia. Further, for patients who are suffering significant muscle reduction, use of medicines to enhance their muscles and enable them to take exercise is a beneficial measure.

As medicines for sarcopenia, a substance that inhibits the activity of myostatin, which is a negative regulator of myogenesis (see, for example, the Japanese translation of PCT International Application Publication No. 2008-530004), and a Fbxo40 antagonist that inhibits insulin receptor substrate 1 (IRS1) that induces myogenesis (see, for example, the Japanese translation of PCT International Application Publication No. 2013-519869) have been proposed. However, these proposals have not yet led to practical applications.

Meanwhile, there have been reports on several research outcomes regarding the relationship between the activity of TAZ, which is a transcriptional coactivator, and the formation and differentiation of skeletal muscles (see, for example, FASEB J 24: 3310-3320 and Biochem. Biophys. Res. Commun. 339: 533-539). These reports suggest that a substance that activates TAZ may promote formation and differentiation of skeletal muscles. As the substances that activate TAZ, a phenyltetrazole derivative (see, for example, Japanese Patent Application Laid-Open No. 2010-280658), kaempferol (see, for example, Bone 50: 364-372) and TM-25659 (see, for example, Br. J. Pharmacol. 165: 1584-1594) are known.

SUMMARY OF THE INVENTION

Problems to be Solved by the Invention

As mentioned above, although some medicines and therapeutic methods with regard to formation and differentiation of muscles have been proposed, they have not reached a satisfactory level in terms of practical application. In view of such circumstances, the invention aims to provide a novel myogenesis promotor, a muscle atrophy inhibitor, a medical composition and a TAZ activator by focusing on TAZ activation. The invention also aims to provide novel functions for a composition having a specific structure, including promoting differentiation of myoblast cells, inhibition of muscle atrophy and TAZ activation; and a novel use of a composition having a specific structure to which the function of activating TAZ can be applied.

Means for Solving the Problem

The means for solving the problem include the following embodiments.

<1> A myogenesis promotor or a muscle atrophy inhibitor, including a compound represented by the following Formula (1) as an active ingredient.

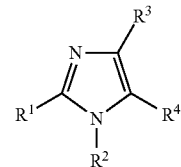

(1)

In Formula (1), $R^1$ represents a hydrogen atom or an alkyl group having 1 to 10 carbon atoms; $R^2$ represents an aryl group, a heterocyclic group, an alkyl group having 1 to 10 carbon atoms, an alkenyl group having 2 to 10 carbon atoms or an alkynyl group having 2 to 10 carbon atoms; $R^3$ represents $-NR^5R^6$ or $-N=C-R^7$; each of $R^5$ and $R^6$ independently represents a hydrogen atom, an alkyl group having 1 to 10 carbon atoms, an alkenyl group having 2 to 10 carbon atoms, an alkynyl group having 2 to 10 carbon atoms, $-C(=O)R^8$ or $-COOR^9$; $R^7$ represents $-NR^{10}R^{11}$, an aryl group or a heterocyclic group; $R^8$ represents a hydrogen atom, an alkyl group having 1 to 10 carbon atoms, an alkenyl group having 2 to 10 carbon atoms or an alkynyl group having 2 to 10 carbon atoms; $R^9$ represents a hydrogen atom, an alkyl group having 1 to 10 carbon atoms, an alkenyl group having 2 to 10 carbon atoms, or an alkynyl group having 2 to 10 carbon atoms; each of $R^{10}$ and $R^{11}$ independently represents a hydrogen atom, an alkyl group having 1 to 10 carbon atoms, an alkenyl group having 2 to 10 carbon atoms, or an alkynyl group having 2 to 10 carbon atoms; $R^4$ represents a cyano group or $-C(=O)R^{12}$; and $R^{12}$ represents an aryl group, a heterocyclic group, an alkyl group having 1 to 10 carbon atoms, an alkenyl group having 2 to 10 carbon atoms, an alkynyl group having 2 to 10 carbon atoms, an alkoxy group having 1 to 10 carbon atoms, an adamanthyl group or a norbornyl group.

<2> The myogenesis promotor or the muscle atrophy inhibitor of <1>, in which $R^2$ is a group represented by following Formula (2) or Formula (3).

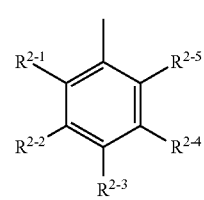

(2)

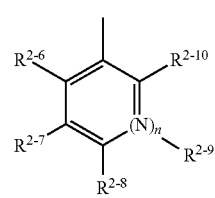

(3)

In Formula (2) and Formula (3), each of $R^{2-1}$ to $R^{2-10}$ independently represents a hydrogen atom, an alkyl group having 1 to 10 carbon atoms, an alkoxy group having 1 to 10 carbon atoms, a cyano group, a nitro group, an amino group or a halogen atom; and n represents the number of nitrogen atoms in the hetero ring, and is an integer from 1 to 6.

<3> The myogenesis promotor or the muscle atrophy inhibitor of <1> or <2>, which is a therapeutic medicine for a disease selected from the group consisting of sarcopenia, steroid myopathy, muscular dystrophy, muscle atrophy due to motor nerve disorder, and muscle atrophy due to cachexia.

<4> A medical composition including a compound represented by Formula (1) as an active ingredient.

<5> The medical composition of <4>, for use in promotion of myogenesis or inhibition of muscle atrophy.

<6> The medical composition of <5>, in which the promotion of myogenesis or the inhibition of muscle atrophy is for treatment of a disease selected from the group consisting of sarcopenia, steroid myopathy, muscular dystrophy, muscle atrophy due to motor nerve disorder, and muscle atrophy due to cachexia.

<7> A TAZ activator including a compound represented by Formula (1).

<8> A compound represented by Formula (1), for use as a medicine for promoting myogenesis or inhibiting muscle atrophy.

<9> The compound of <8>, in which the medicine is for treatment of a disease selected from the group consisting of sarcopenia, steroid myopathy, muscular dystrophy, muscle atrophy due to motor nerve disorder, and muscle atrophy due to cachexia.

<10> Use of a compound represented by Formula (1) for production of a medicine.

<11> The use of <10>, in which the medicine is for promoting myogenesis or inhibiting muscle atrophy.

<12> The use of <11>, in which the medicine for promoting myogenesis or inhibiting muscle atrophy is for treatment of a disease selected from the group consisting of sarcopenia, steroid myopathy, muscular dystrophy, muscle atrophy due to motor nerve disorder, and muscle atrophy due to cachexia.

<13> A method of promoting myogenesis or inhibiting muscle atrophy, including any one of the following (1) to (3).

(1) Administering a compound represented by Formula (1) to an individual.

(2) Contacting a compound represented by Formula (1) with an organ or a tissue.

(3) Contacting a compound represented by Formula (1) with a cell.

<14> A treatment method for a disease selected from the group consisting of sarcopenia, steroid myopathy, muscular dystrophy, muscle atrophy due to motor nerve disorder, and muscle atrophy due to cachexia.

<15> A method of activating TAZ, including any one of the following (1) to (3).

(1) Administering a compound represented by Formula (1) to an individual.

(2) Contacting a compound represented by Formula (1) with an organ or a tissue.

(3) Contacting a compound represented by Formula (1) with a cell.

Effect of the Invention

According to the invention, a novel myogenesis promotor, a novel muscle atrophy inhibitor, a novel medical composition and a novel TAZ activator can be provided.

EMBODIMENTS FOR IMPLEMENTING THE INVENTION

Figure 1A:
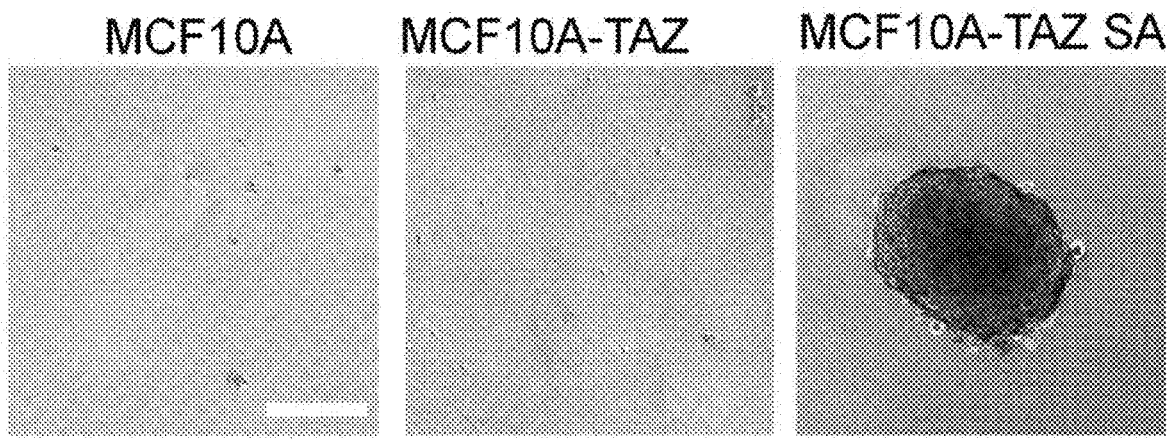
FIG. 1A is a drawing showing the result of sphere formation test of MCF10A cells.
Figure 1B:
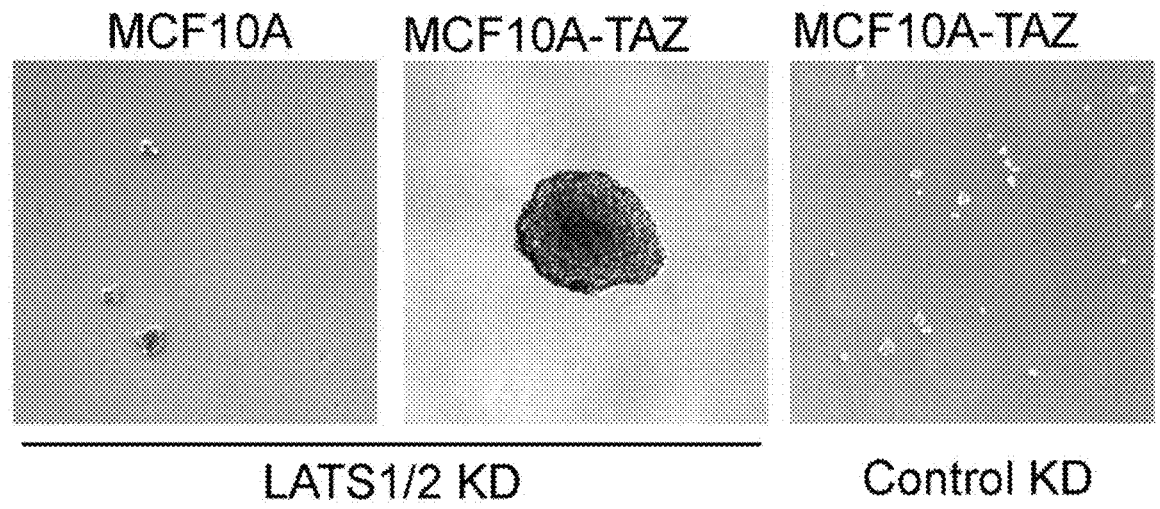
FIG. 1B is a drawing showing the result of sphere formation test of MCF10A cells.
Figure 1C:
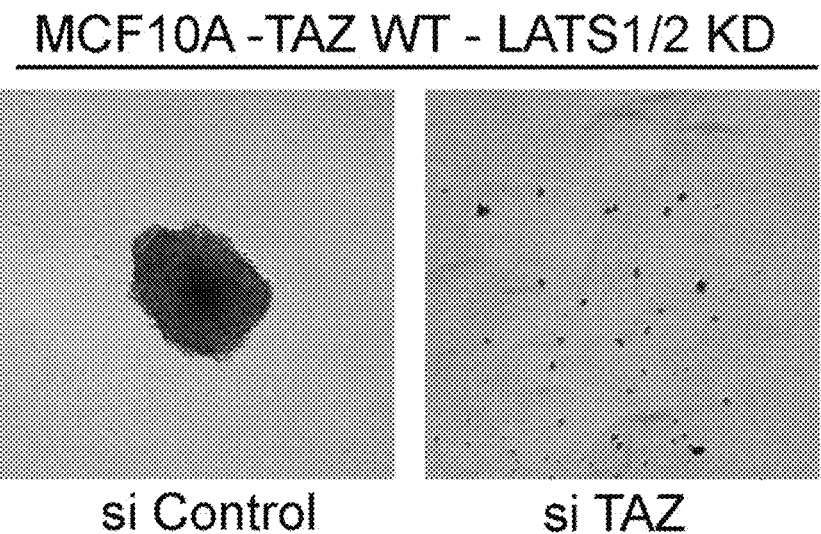
FIG. 1C is a drawing showing the result of sphere formation test of MCF10A cells.

In the specification, the term "myogenesis" refers to a process until myoblast cells form muscle fibers via proliferation and differentiation. The type of the myoblast cell is not specifically limited. The term "promotion of muscle formation" includes supplementing the total or part of the volume of muscle that has reduced by atrophy or damage to muscle fibers, with newly generated muscle fibers, in addition to increasing the volume of muscle by increasing the number or the size of muscle fibers. The term "muscle atrophy" includes myogenic atrophy caused by muscle itself, neurogenic atrophy caused by motor neuron, disuse muscle atrophy cause by not using muscles for a long time, muscle atrophy caused by medicines such as steroid myopathy, and muscle atrophy caused by direct or indirect factors such as aging, cachexia, endocrine conditions, nutritional conditions, external injury and diseases. The term "cachexia" includes cancer and those caused by various chronic diseases such as cardiac failure, renal failure and respiratory illness. The term "treatment" includes not only removing symptoms but also retarding aggravation or alleviating symptoms. The numbers shown in the tables are rounded off to two decimal places.

TAZ (also referred to as WWTR1) is a known protein, and the base sequence of its gene corresponds to the arrangement of the 235 to 1437th of NCBI Accession No. BC014052.2. TAZ is a 14-3-3 binding protein that is composed of a N-terminal TEAD-binding domain, a WW domain, and a transcriptional activation domain. TAZ functions as a transcriptional co-activator.

Transcription factors that interact with TAZ include TEADs that promotes cell proliferation or epithelial-mesenchymal transition (EMT), Wbp2 that promotes cell proliferation or epithelial-mesenchymal transition (EMT), SMAD2/3 that promotes self-replication or regulates differentiation of tissue stem cells, Runx2 that promotes bone formation, PPARγ that suppresses adipogenesis, MyoD that promotes formation of muscle, TTF1 (NKK2.1) that promotes formation of lung or thyroid, PAX3 that promotes formation of muscle, PAX8 that promotes formation of thyroid, TBX5 that promotes formation of heart or upper extremity.

TAZ is known to be regulated by Hippo Pathway, junction protein, actin cytoskeleton, Wnt Pathway and the like, and regulation by Hippo Pathway is the best known among them.

Hippo Pathway is a signaling pathway formed of upstream regulatory molecules (membrane proteins and membrane lining proteins that are involved in cell adhesion and cell polarity), core kinase cascade (two kinds of Ser/Thr kinases, adaptor molecules, and kinase activating molecules), and downstream target molecule (transcription co-activators that are phosphorylated by kinase cascade, and transcription factors that are bound to the transcription co-activators). When the cell density is high, the function of Hippo Pathway becomes ON and TAZ is phosphorylated by LATS1/2 constituting the core kinase cascade. The phosphorylated TAZ is transferred from the cell nucleus to the cytoplasm, and is decomposed. As a result, transcription of genes that promotes cell proliferation or suppresses cell death is suppressed, and the number of cells is increased. When the cell density is low, the function of Hippo Pathway becomes OFF, and TAZ remains in the cell nucleus without being phosphorylated. TAZ is bound to a transcription factor and transcription of genes that promotes cell proliferation or suppresses cell death is promoted (i.e., TAZ is activated), and the number of cells is increased.

In the specification, the term "TAZ activator" refers to a substance having a function of forming a sphere in a system in which mammary epithelial cells (MCF10A cells) are used. When TAZ is activated, it remains in the cell nucleus without being phosphorylated, and is bound to a transcription factor. As a result, it is considered that cell proliferation is promoted and a sphere is formed. When TAZ is not activated, it is phosphorylated and transferred to the cytoplasm, and is decomposed.

The myogenesis promotor, the muscle atrophy inhibitor, the medical composition or the TAZ activator of the invention includes a compound represented by following Formula (1) (hereinafter, also referred to as a specific compound) as an active ingredient.

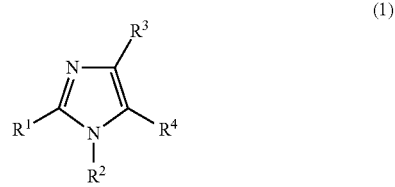

In Formula (1), $R^1$ represents a hydrogen atom or an alkyl group having 1 to 10 carbon atoms; $R^2$ represents an aryl group, a heterocyclic group, an alkyl group having 1 to 10 carbon atoms, an alkenyl group having 2 to 10 carbon atoms or an alkynyl group having 2 to 10 carbon atoms; $R^3$ represents $-NR^5R^6$ or $-N=C-R^7$; each of $R^5$ and $R^6$ independently represents a hydrogen atom, an alkyl group having 1 to 10 carbon atoms, an alkenyl group having 2 to 10 carbon atoms, an alkynyl group having 2 to 10 carbon atoms, $-C(=O)R^8$ or $-COOR^9$; $R^7$ represents $-NR^{10}R^{11}$, an aryl group or a heterocyclic group; $R^8$ represents a hydrogen atom, an alkyl group having 1 to 10 carbon atoms, an alkenyl group having 2 to 10 carbon atoms or an alkynyl group having 2 to 10 carbon atoms; $R^9$ represents a hydrogen atom, an alkyl group having 1 to 10 carbon atoms, an alkenyl group having 2 to 10 carbon atoms, or an alkynyl group having 2 to 10 carbon atoms; each of $R^{10}$ and $R^{11}$ independently represents a hydrogen atom, an alkyl group having 1 to 10 carbon atoms, an alkenyl group having 2 to 10 carbon atoms, or an alkynyl group having 2 to 10 carbon atoms; R4 represents a cyano group or $-C(=O)R^{12}$; and $R^{12}$ represent an aryl group, a heterocyclic group, an alkyl group having 1 to 10 carbon atoms, an alkenyl group having 2 to 10 carbon atoms, an alkynyl group having 2 to 10 carbon atoms, an alkoxy group having 1 to 10 carbon atoms, an adamanthyl group or a norbornyl group.

In Formula (1), the structure of the alkyl group, the alkenyl group or the alkynyl group, which is represented by any appropriate one of $R^1$ to $R^{12}$, is not specifically limited, and may be linear or may be branched or cylic, when possible. The alkyl group, the alkenyl group or the alkynyl group may have a substituent, when possible.

Specific examples of the alkyl group include a methyl group, an ethyl group, a propyl group, a butyl group, a pentyl group, a hexyl group, an octyl group, a nonyl group, a decyl group, a substituent having a structure in which any of these alkyl group is branched, and a substituent having a structure in which any of these alkyl groups is cyclic.

Specific examples of the alkenyl group include an etenyl group, a propenyl group, a butenyl group, a pentenyl group, a hexenyl group, an octenyl group, a nonenyl group, a decenyl group, a substituent having a structure in which any of these alkenyl group is branched, and a substituent having a structure in which any of these alkenyl groups is cyclic.

Specific examples of the alkynyl group include an ethynyl group, a propynyl group, a buthynyl group, a penthynyl group, a hexynyl group, a heptynyl group, an octynyl group, an nonynyl group, a decynyl group, a substituent having a structure in which any of these alkynyl group is branched, and a substituent having a structure in which any of these alkynyl groups is cyclic.

In Formula (1), the structure of the alkoxy group, which is represented by any appropriate one of $R^1$ to $R^{12}$, is not specifically limited, and may be linear or may be branched or cylic, when possible. The alkoxy group may have a substituent, when possible. Specific examples of the alkoxy group include combinations of an oxygen atom with any of the specific examples of the alkyl group, the alkenyl group or the alkynyl group as mentioned above.

In Formula (1), the structure of the aryl group, which is represented by any appropriate one of $R^1$ to $R^{12}$, is not specifically limited, and may be monocyclic or polycyclic. The aryl group may have a substituent, when possible. Specific examples of the aryl group include a phenyl group and a naphthyl group.

In Formula (1), the structure of the heterocyclic group, which is represented by any appropriate one of $R^1$ to $R^{12}$, is not specifically limited, and may be monocyclic or polycyclic. Specific examples of the heterocyclic group include a substituent derived from a heterocyclic compound including at least one hetero atom of one or more kinds selected from the group consisting of a nigrogen atom, an oxygen atom and a sulfur atom. The heterocyclic group may have a substituent, when possible.

Specific examples of the heterocyclic group include a substituent derived from a 6-member heterocyclic compound, such as a morpholinyl group, a piperidinyl group, a pyridinyl group, a pyrazinyl group, a pyrazinoyl group, a piperazinyl group, a pyrimidinyl group, a pyridazinyl group, a tetrahydropyranyl group, and a tetrahydrothiopyranyl group; and a substituent derived from a 5-member heterocyclic compound, such as a pyrrolidinyl group, a pyrrolyl group, an imidazolyl group, a pyrazolyl group, a thiazolyl group, an oxazolyl group, a furanyl group, an oxolanyl group, and a thiophenyl group.

Specific examples of the substituent for the alkyl group, an alkenyl group, an alkynyl group, an alkoxy group, an aryl group, a heterocyclic group, an adamanthyl group or a norbornyl group include the specific examples of the alkyl group, the alkenyl group, the alkynyl group and the alkoxy group as mentioned above, an alkylcarbonyl group having 1 to 10 carbon atoms, an alkoxycarbonyl group having 1 to 10 carbon atoms, an arylcarbonyl group having 1 to 10 carbon atoms, an alkylcarbonylamino group having 1 to 10 carbon atoms, an alkoxycarbonylamino group having 1 to 10 carbon atoms, an arylcarbonylamino group having 1 to 10 carbon atoms, halogen atoms such as a fluorine atom, a chlorine atom, an iodine atom and a bromine atom, a cyano group, a nitro group, and an amino group.

$R^1$ is preferably a hydrogen atom or an alkyl group having 1 to 6 carbon atoms, more preferably a hydrogen atom or an alkyl group having 1 to 3 carbon atoms, further preferably a hydrogen atom.

$R^2$ is preferably a group represented by following Formula (2) or Formula (3).

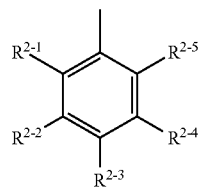

(2)

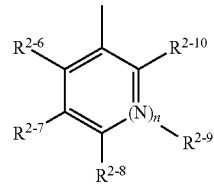

(3)

In Formula (2) and Formula (3), each of $R^{2-1}$ to $R^{2-10}$ independently represents a hydrogen atom, an alkyl group having 1 to 10 carbon atoms, an alkenyl group having 2 to 10 carbon atoms, an alkynyl group having 2 to 10 carbon atoms, an alkoxy group having 1 to 10 carbon atoms, a cyano group, a nitro group, an amino group or a halogen atom; n represents the number of nitrogen atoms in the hetero ring, and is an integer of from 1 to 6.

In Formula (2) and Formula (3), the structure of the alkyl group, the alkenyl group, the alkynyl group or the alkoxy group represented by any appropriate one of $R^{2-1}$ to $R^{2-10}$ is not specifically limited, and may be linear or may be branched or cyclic, when possible. The alkyl group, the alkenyl group, the alkynyl group or the alkoxy group may have a substituent, when possible. Specific example of the substituent for the alkyl group, the alkenyl group, the alkynyl group or the alkoxy group include the specific examples of the substituent for the alkyl group, the alkenyl group, the alkynyl group or the alkoxy group in Formula (1), the specific examples of the halogen atoms in Formula (1), and the specific examples of the alkyl group, the alkenyl group, the alkynyl group or the alkoxy group in Formula (1).

$R^2$ is preferably a group represented by Formula (2). Each of $R^{2-1}$ to $R^{2-10}$ is independently preferably a hydrogen atom, an unsubstituted alkyl group having 1 to 5 carbon atoms, an alkyl group having 1 to 5 carbon atoms and an amino group, a cyano group or an alkoxycarbonylamino group as a substituent, an unsubstituted alkoxy group having 1 to 5 carbon atoms, or a halogen atom. Each of $R^{2-1}$ to $R^{2-10}$ is independently more preferably a hydrogen atom, an unsubstituted methyl group, a methyl group having a cyano group as a substituent, an aminoethyl group, an unsubstituted pentyl group, an ethyl group having a t-butoxycarbonylamino group as a substituent, a methoxy group, a bromine atom, or a chlorine atom.

When $R^3$ represents $—NR^5R^6$, each of $R^5$ and $R^6$ is independently preferably a hydrogen atom, an alkyl group having 1 to 6 carbon atoms, $—C(=O)R^8$ in which $R^8$ is a hydrogen atom or an alkyl group having 1 to 3 carbon atoms, or $—COOR^9$ in which $R^9$ is an alkyl group having 1 to 3 carbon atoms. Each of $R^5$ and $R^6$ is independently more preferably a hydrogen atom, a methyl group, a formyl group, an acetyl group or an ethoxycarbonyl group.

When $R^3$ represents $—N=C—R^7$, $R^7$ is preferably a dialkylamino group, a phenyl group, a morpholinyl group or a piperidinyl group. $R^7$ is more preferably a dimethylamino group, an unsubstituted phenyl group, an unsubstituted morpholinyl group or an unsubstituted piperidinyl group.

$R^4$ is preferably a cyano group or $—C(=O)R^{12}$ in which $R^{12}$ is a phenyl group, an alkyl group having 1 to 6 carbon atoms, an alkoxy group having 1 to 6 carbon atoms, an adamanthyl group or a norbornyl group. $R^4$ is more preferably a cyano group or $—C(=O)R^{12}$ in which $R^{12}$ is a methyl group, an ethyl group, a phenyl group or an adamanthyl group. $R^4$ is further preferably a cyano group or —C(=O)$R^{12}$ in which $R^{12}$ is an unsubstituted methyl group, an unsubstituted ethyl group, an unsubstituted phenyl group, a phenyl group having a chlorine atom, a bromine atom, a fluorine atom, a nitro group or a methoxy group as a substituent, or an unsubstituted adamanthyl group.

<Method of producing Specific Compound>

The method of producing the specific compound and/or a pharmaceutically acceptable salt thereof is not specifically limited, and may be selected according to purposes. For example, a compound having a structure of Formula (1) in which $R^3$ is —$NH^3$ can be produced via a compound represented by following Formula (4), which is produced by a method described in Journal fuer Praktische Chemie, 1976, Vol. 318-2, 347-349, and a compound represented by following Formula (5), which is produced by a method described in Monatschefte fur Chemie, 1976, Vol. 107, 1413-1421 or Monatschefte fur Chemie, 1996, Vol. 127, 313-318. Further, the compound can be converted to a derivative of $R^3$ by an ordinary method for alkylation, acylation or a method described in Tetrahedron, 2000, Vol. 56, 8253-8262.

Specifically, a compound of Formula (5) can be obtained by reacting a compound of Formula (4) with a halogenated alkyl in the presence of a base such as potassium carbonate in a suitable solvent such as dimethyl formamide, acetone or tetrahydrofuran at room temperature or in a heated condition. The compound of Formula (4) is obtained from cyanamide and an amine of equivalent amounts and a trialkylorthoaliphatic ester of 1.5 to 2 equivalent amounts while heating at 130° C. to 140° C. By further reacting in a solvent such as methanol, ethanol or dimethyl formamide with a small amount of sodium alkoxide or sodium hydride, at room temperature for some minutes, a compound of Formula (1) in which $R^3$ is —$NH_2$ can be obtained. By reacting the compound with a formamide at room temperature in the presence of p-toluenesulfonyl chloride, a compound in which $R^3$ is —N=C—$R^7$ can be obtained.

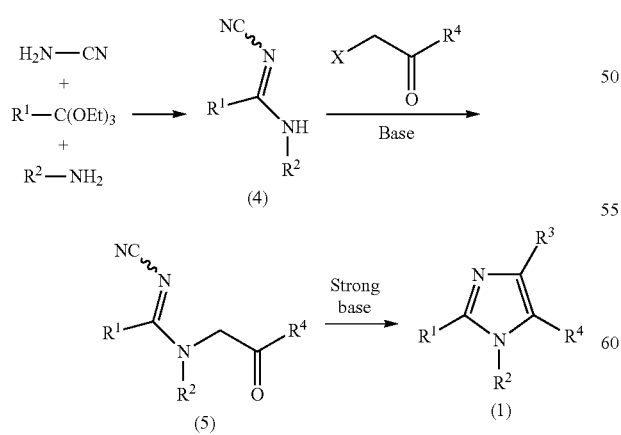

Examples of the specific compound includes following exemplary compounds 1 to 44.

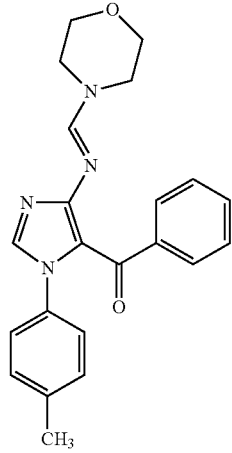

1

2

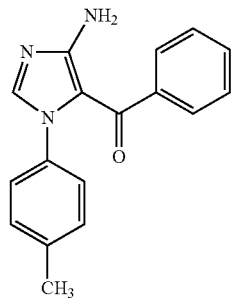

3

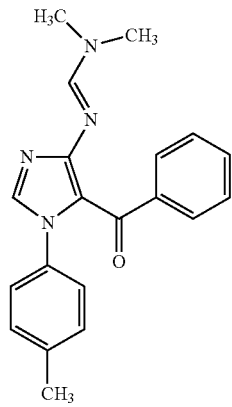

4

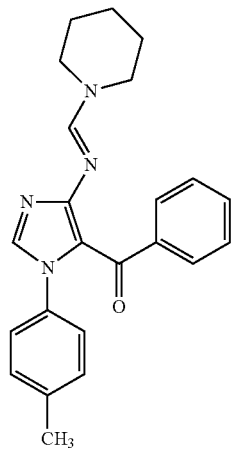

5
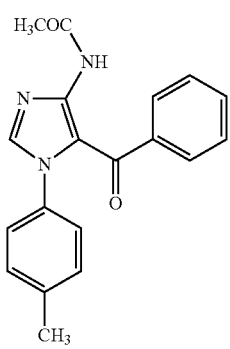
6
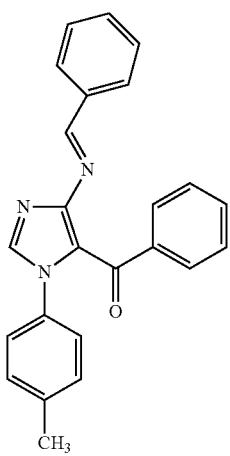
7
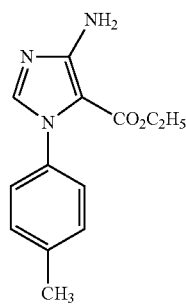
8
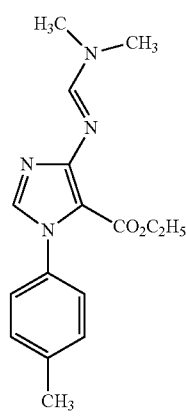
9
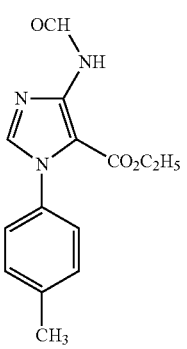
10
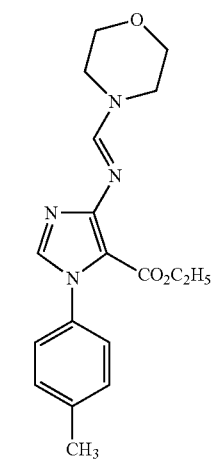
11
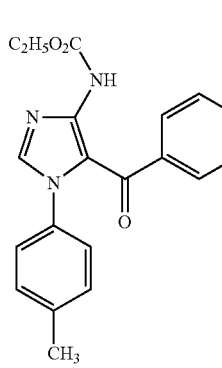
12
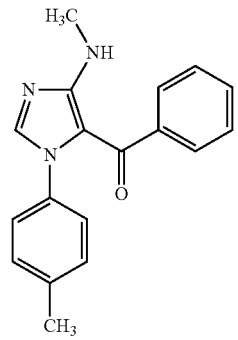

13
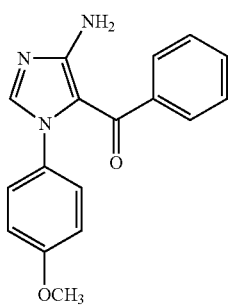
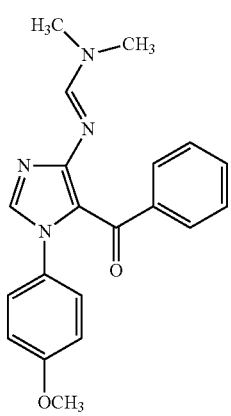
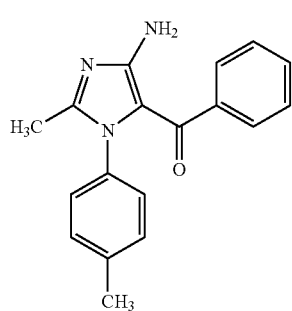
14
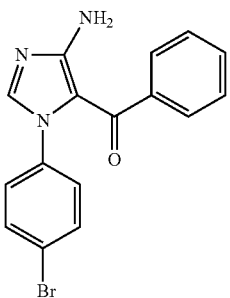
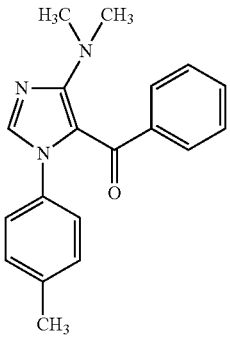
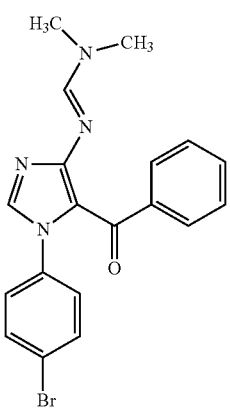
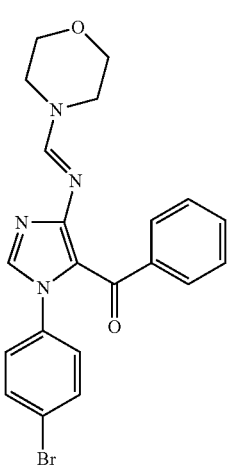

21
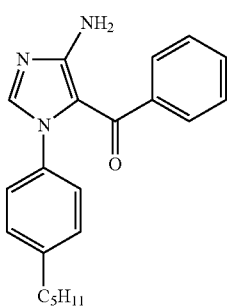
22
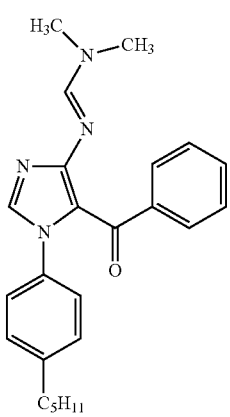
23
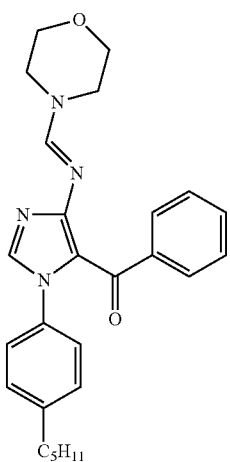
24
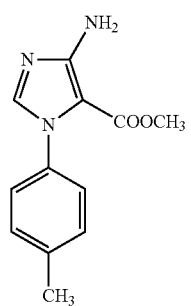
25
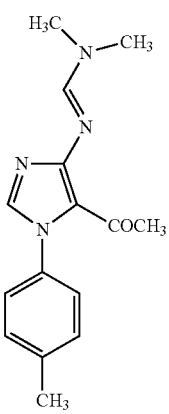
26
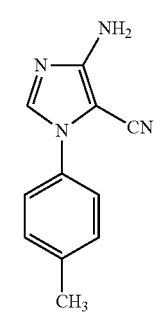
27
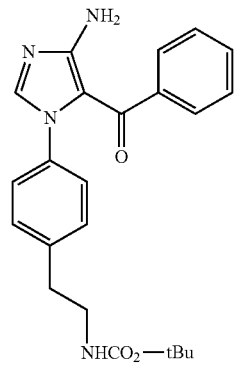
28
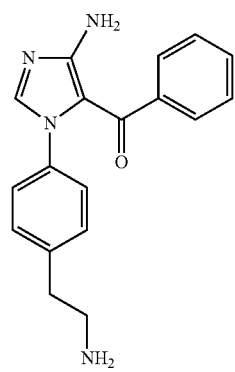

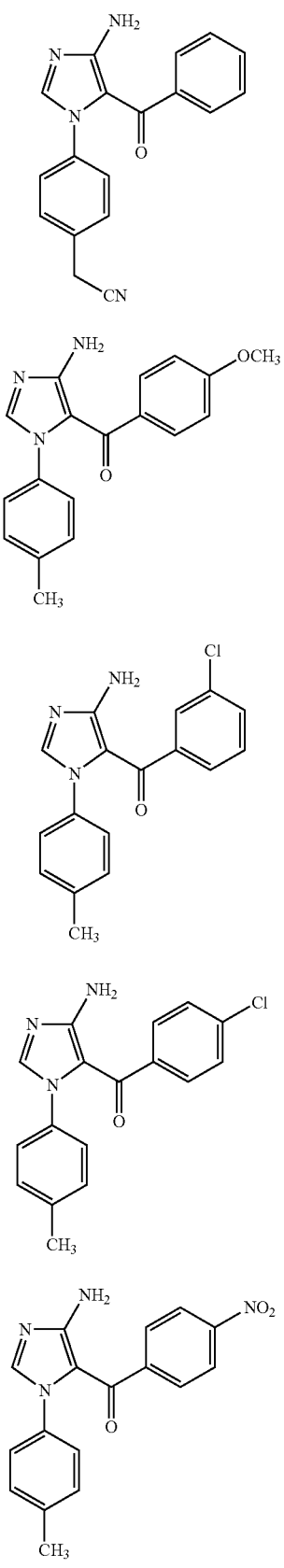
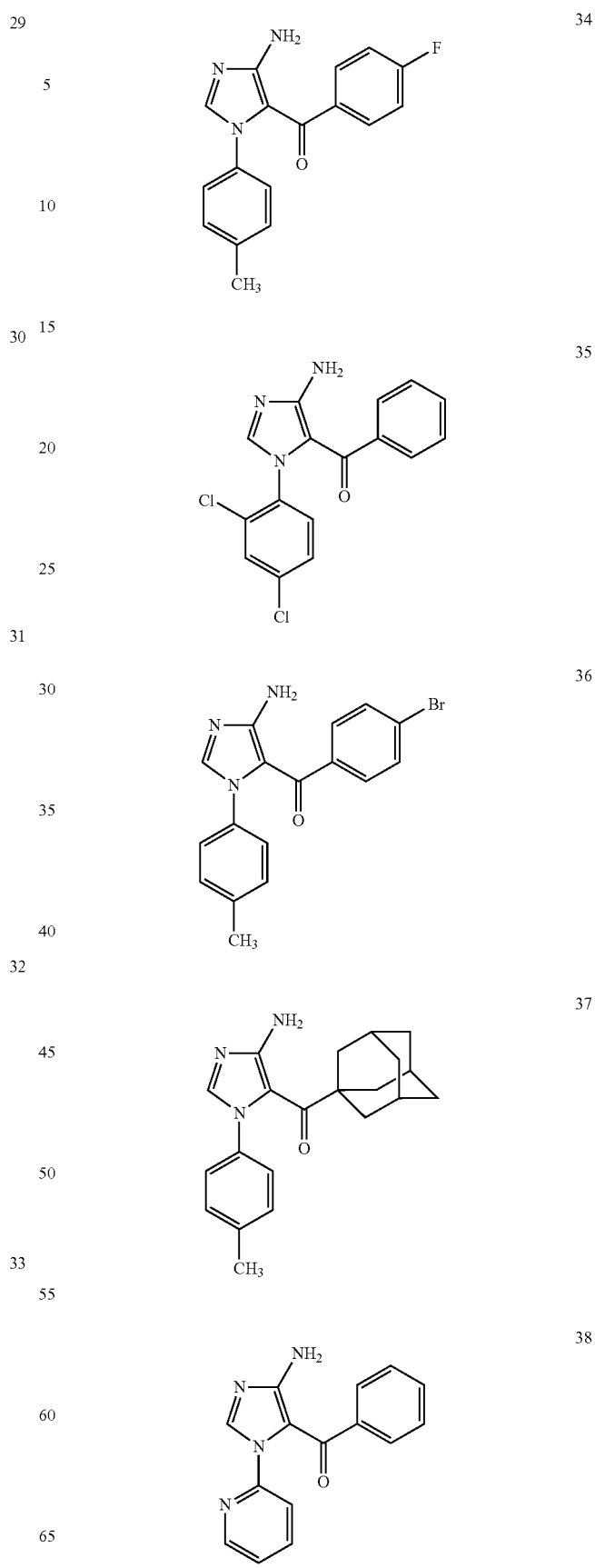

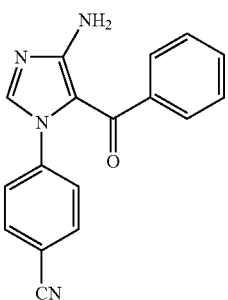
39

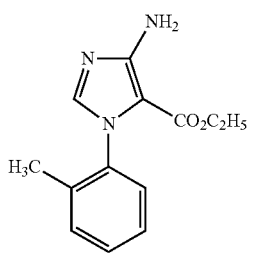
40

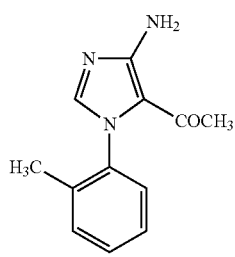
41

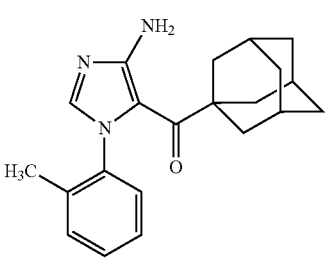
42

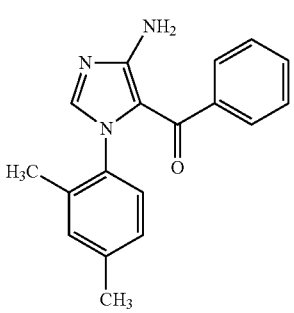
43

44

The inventors have found that when mammary epithelial cells (MCF10A cells) are cultured in the presence of the specific compound, formation of a sphere due to activation of TAZ is promoted (i.e., the specific compound has a function of activating TAZ), and that differentiation of myoblast cells is promoted (i.e., muscle formation is promoted and muscle atrophy is suppressed). These findings are not known with regard to a compound having a structure as mentioned above.

The myogenesis promotor, the muscle atrophy inhibitor and the medical composition of the invention are useful for therapeutic treatments for various diseases caused by muscle reduction or deficiency due to atrophy, reduction, inadequate development or the like of muscle fibers. Examples of the diseases to which the myogenesis promotor, the muscle atrophy inhibitor or the medical composition of the invention is applied include sarcopenia, steroid myopathy, muscular dystrophy, muscle atrophy due to motor nerve disorder, and muscle atrophy due to cachexia.

The TAZ activator of the invention is useful for various applications to which activation of TAZ can be applied, and examples thereof include treatment or prevention of osteoporosis and suppression of obesity.

The myogenesis promotor, the muscle atrophy inhibitor, the medical composition or the TAZ activator of the invention may include components other than the specific compound. Examples of the components include a solid medium such as gelatin and lactose, a liquid medium such as water, saline and glucose aqueous solution, a surfactant such as sugar, polyhydric alcohol and polyhydric alcohol ester, and a buffer such as sodium citrate and sodium phosphate.

The method of administration of the myogenesis promotor, the muscle atrophy inhibitor, the medical composition or the TAZ activator of the invention is not particularly limited. Examples of the method include oral administration such as intraoral administration and sublingual administration, and parenteral administration such as intravenous administration, intramuscular administration, subcutaneous administration, transdermal administration, intranasal administration and lung administration. Among these, intravenous administration, intramuscular administration and oral administration are preferred, and intramuscular administration is particularly preferred. From the viewpoint of low invasiveness, transdermal administration is preferred.

The individual as the subject for the administration of the myogenesis promotor, the muscle atrophy inhibitor, the medical composition or the TAZ activator of the invention is not limited to human being, and include livestock animals, pet animals and laboratory animals.

The myogenesis promotor, the muscle atrophy inhibitor, the medical composition or the TAZ activator of the invention may be used in vitro. For example, the myogenesis promotor, the muscle atrophy inhibitor, the medical composition or the TAZ activator of the invention may be allowed to contact with an organ, a tissue or a cell.

Embodiments of the use of the myogenesis promotor of the invention include injecting the myogenesis promotor into muscle as the subject, together with cells obtained from the myoblast cells of the subject or obtained by causing differentiation of versatile cells such as iPS cells obtained from the subject into myoblast cells; and transplanting muscle fibers that have been cultured together with the myogenesis promotor of the invention.

EXAMPLES

In the following, the invention is explained in detail by referring to the Examples. However, the invention is not limited to these Examples.

The following experiments were conducted to confirm that the specific compound has a function of activating TAZ (FIGS. 1A to 1D). The line in the figures is 200 µm.

(1) Mammary epithelial (MCF10A) cells, MCF10A cells expressing TAZ ((MCF10A-TAZ), and MCF10A cells expressing constitutively active TAZ, a TAZ S89A mutant with Serine 98 being substituted by alanine (MCF10A-TAZ SA) were cultured under sphere formation condition, respectively. As a result, only MCF10A-TAZ SA cells formed spheres (see FIG. 1A).

(2) MCF10A cells and MCF10A-TAZ cells, in which LATS1 and LATS 2 were knocked down by the knockdown construction as mentioned later, were cultured under sphere formation condition, respectively. As a result, MCF10A-TAZ cells formed spheres. MCF10A cells did not form spheres even with LATS1 and LATS 2 being knocked down (see FIG. 1B).

(3) MCF10A cells with TAZ knock down with knockdown construction as mentioned later, in addition to LATS1 and LATS 2 (si TAZ) were cultured under sphere formation condition. As a result, an ability of forming spheres was lost (see FIG. 1C). There results show that MCF10A cells form spheres when TAZ is activated.

Figure 1D:
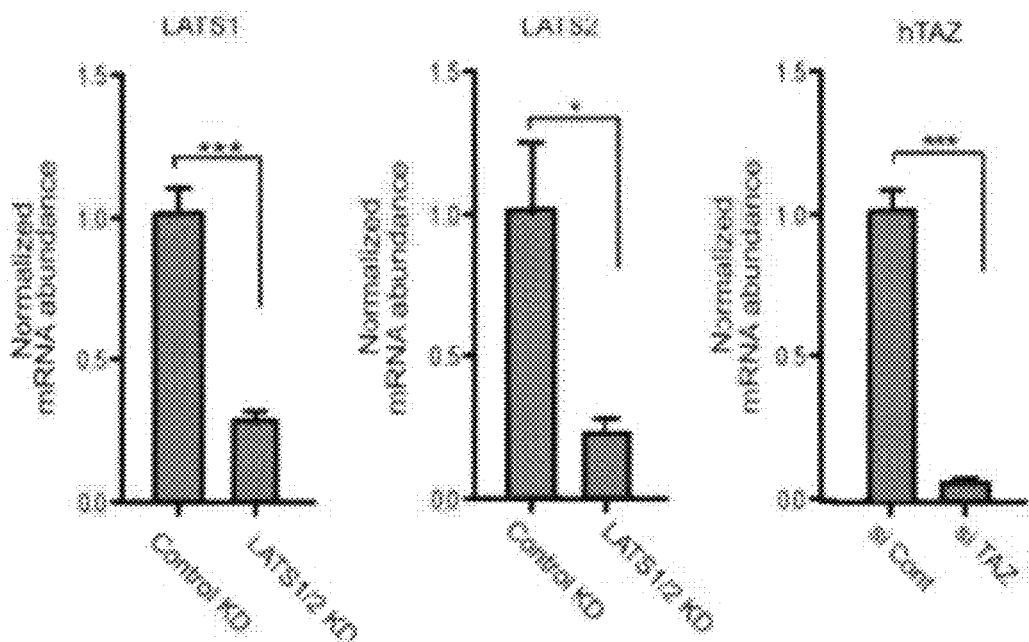
FIG. 1D is a drawing showing the result of sphere formation test of MCF10A cells.

(4) The results of the verification of LATS1, LATS 2 and TAZ knockdown are shown in Table 1 and FIG. 1D. The line and the bar in the Figure indicate the average value and the standard error, and *p<0.05, ***p<0.001.

Subsequently, MCF10A-TAZ cells were cultured under sphere formation condition, with exemplary compound 1 (following structure, InterBioScreen Ltd., also referred to as IBS008738) at 10 µM for 14 days. As a result, spheres (a cell aggregate with a longest diameter greater than 150 µm was defined as a sphere) were formed by MCF10A-TAZ cells. There results show that IBS008738 has a function of activating TAZ.

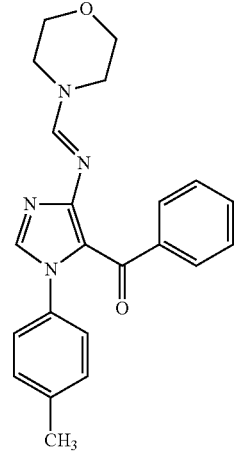

IBS008738

<Evaluation of Myogenesis of C2C12 Cells with Specific Compound>

Exemplary compounds 2 to 44 having the aforementioned structures were prepared as the specific compounds, and the state of myogenesis of C2C12 cells with exemplary compounds 1 to 44 were evaluated by the following method.

(1) C2C12 cells were grown to confluence under growth condition, and then in differentiation condition for 72 hours, in a culture medium added with DMSO, IBS008738 (exemplary compound 1) or exemplary compounds 2 to 44, at a concentration of 1 µM, 3 µM or 10 µM, respectively. Thereafter, the degree of myogenesis was evaluated by a fusion index (a value obtained by dividing the number of nuclei detected in multinucleated myosin heavy chain (MHC)-positive cells by the total number of the nuclei). Specifically, exemplary compounds were divided into five groups, and DMSO and IBS008738 were evaluated in each group as controls. The evaluation was conducted three times, and the average value and the standard deviation of the fusion index was relativized with the measured value of DMSO as 1. As shown in Table 2, the relative fusion index (FI) of the cases with IBS0008738 (exemplary compound 1) and exemplary compounds 2 to 44 were greater than that of DMSO.

TABLE 1

| | Normarized mRNA abundance | | | | | | | | | | |
|---|---|---|---|---|---|---|---|---|---|---|---|
| | LATS1 | | | | LATS2 | | | | hTAZ | | |
| conKD | 0.91 | 1.04 | 1.05 | conKD | 1.42 | 0.84 | 0.75 | siCont | 1.13 | 0.98 | 0.90 |
| LATS1/2 KD | 0.38 | 0.40 | 0.39 | LATS1/2 KD | 0.37 | 0.38 | 0.26 | siTAZ | 0.05 | 0.07 | 0.06 |

TABLE 2

| | Group 1 | | | Group 2 | | | Group 3 | | | Group 4 | | | Group 5 | | |
|---|---|---|---|---|---|---|---|---|---|---|---|---|---|---|---|
| | No. | FI | SD | No. | FI | SD | No. | FI | SD | No. | FI | SD | No. | FI | SD |
| DMSO | | 1.00 | 0.02 | | 1.00 | 0.05 | | 1.00 | 0.07 | | 1.00 | 0.06 | | 1.00 | 0.05 |
| 10 μM | 1 | 2.00 | 0.17 | 1 | 2.03 | 0.17 | 1 | 1.76 | 0.22 | 1 | 1.68 | 0.08 | 1 | 1.33 | 0.05 |
| 3 μM | | 1.89 | 0.11 | | 1.80 | 0.06 | | 1.67 | 0.14 | | 1.53 | 0.10 | | 1.18 | 0.05 |
| 1 μM | | 1.47 | 0.10 | | 1.33 | 0.12 | | 1.28 | 0.09 | | 1.13 | 0.09 | | 1.10 | 0.04 |
| 10 μM | 2 | 2.41 | 0.23 | 11 | 1.47 | 0.14 | 18 | 1.85 | 0.20 | 27 | 1.98 | 0.15 | 38 | 1.15 | 0.10 |
| 3 μM | | 2.26 | 0.23 | | 1.56 | 0.09 | | 1.52 | 0.20 | | 1.67 | 0.19 | | 1.12 | 0.07 |
| 1 μM | | 1.62 | 0.17 | | 1.07 | 0.09 | | 1.34 | 0.17 | | 0.97 | 0.15 | | 1.08 | 0.08 |
| 10 μM | 3 | 1.43 | 0.09 | 12 | 1.36 | 0.22 | 19 | 1.63 | 0.26 | 28 | 1.64 | 0.15 | 39 | 1.09 | 0.08 |
| 3 μM | | 1.52 | 0.11 | | 1.43 | 0.12 | | 1.57 | 0.27 | | 1.42 | 0.22 | | 1.10 | 0.10 |
| 1 μM | | 1.30 | 0.20 | | 1.24 | 0.12 | | 1.25 | 0.07 | | 1.21 | 0.02 | | 1.04 | 0.08 |
| 10 μM | 4 | 1.51 | 0.12 | 13 | 1.53 | 0.13 | 20 | 1.60 | 0.09 | 29 | 1.61 | 0.14 | 40 | 1.10 | 0.05 |
| 3 μM | | 1.54 | 0.28 | | 1.32 | 0.07 | | 1.41 | 0.06 | | 1.49 | 0.33 | | 1.15 | 0.06 |
| 1 μM | | 1.02 | 0.12 | | 1.22 | 0.04 | | 1.26 | 0.14 | | 1.25 | 0.25 | | 1.12 | 0.07 |
| 10 μM | 5 | 1.57 | 0.21 | 14 | 1.72 | 0.15 | 21 | 2.07 | 0.23 | 30 | 1.54 | 0.13 | 41 | 1.11 | 0.07 |
| 3 μM | | 1.50 | 0.31 | | 1.63 | 0.06 | | 1.91 | 0.37 | | 1.52 | 0.05 | | 1.06 | 0.08 |
| 1 μM | | 0.85 | 0.14 | | 1.18 | 0.07 | | 1.47 | 0.21 | | 1.27 | 0.06 | | 1.14 | 0.09 |
| 10 μM | 6 | 1.42 | 0.13 | 15 | 1.58 | 0.25 | 22 | 1.65 | 0.30 | 31 | 1.40 | 0.24 | 42 | 1.10 | 0.07 |
| 3 μM | | 1.78 | 0.35 | | 1.58 | 0.09 | | 1.56 | 0.07 | | 1.15 | 0.05 | | 1.03 | 0.07 |
| 1 μM | | 0.96 | 0.10 | | 1.20 | 0.05 | | 1.13 | 0.29 | | 1.12 | 0.06 | | 1.08 | 0.09 |
| 10 μM | 7 | 1.44 | 0.24 | 16 | 1.60 | 0.13 | 23 | 1.52 | 0.25 | 32 | 1.60 | 0.05 | 43 | 1.12 | 0.06 |
| 3 μM | | 1.55 | 0.13 | | 1.18 | 0.19 | | 1.51 | 0.27 | | 1.47 | 0.17 | | 1.11 | 0.06 |
| 1 μM | | 1.09 | 0.22 | | 1.06 | 0.09 | | 1.25 | 0.07 | | 1.16 | 0.08 | | 1.07 | 0.05 |
| 10 μM | 8 | 1.05 | 0.11 | 17 | 2.07 | 0.28 | 24 | 1.36 | 0.09 | 33 | 1.23 | 0.11 | 44 | 1.07 | 0.06 |
| 3 μM | | 1.53 | 0.32 | | 2.14 | 0.05 | | 1.18 | 0.15 | | 1.20 | 0.12 | | 1.08 | 0.04 |
| 1 μM | | 0.93 | 0.20 | | 1.51 | 0.06 | | 0.86 | 0.06 | | 0.91 | 0.22 | | 1.11 | 0.06 |
| 10 μM | 9 | 1.17 | 0.20 | | | | 25 | 1.44 | 0.05 | 34 | 1.49 | 0.08 | | | |
| 3 μM | | 1.39 | 0.23 | | | | | 1.22 | 0.22 | | 1.33 | 0.03 | | | |
| 1 μM | | 0.97 | 0.15 | | | | | 0.96 | 0.08 | | 1.38 | 0.28 | | | |
| 10 μM | 10 | 0.85 | 0.14 | | | | 26 | 1.44 | 0.26 | 35 | 1.55 | 0.02 | | | |
| 3 μM | | 1.31 | 0.11 | | | | | 1.09 | 0.05 | | 1.60 | 0.05 | | | |
| 1 μM | | 0.80 | 0.13 | | | | | 1.01 | 0.08 | | 1.27 | 0.08 | | | |
| 10 μM | | | | | | | | | | 36 | 1.59 | 0.19 | | | |
| 3 μM | | | | | | | | | | | 1.57 | 0.15 | | | |
| 1 μM | | | | | | | | | | | 1.12 | 0.08 | | | |
| 10 μM | | | | | | | | | | 37 | 1.77 | 0.31 | | | |
| 3 μM | | | | | | | | | | | 1.47 | 0.21 | | | |
| 1 μM | | | | | | | | | | | 1.39 | 0.20 | | | |

Figure 2A:
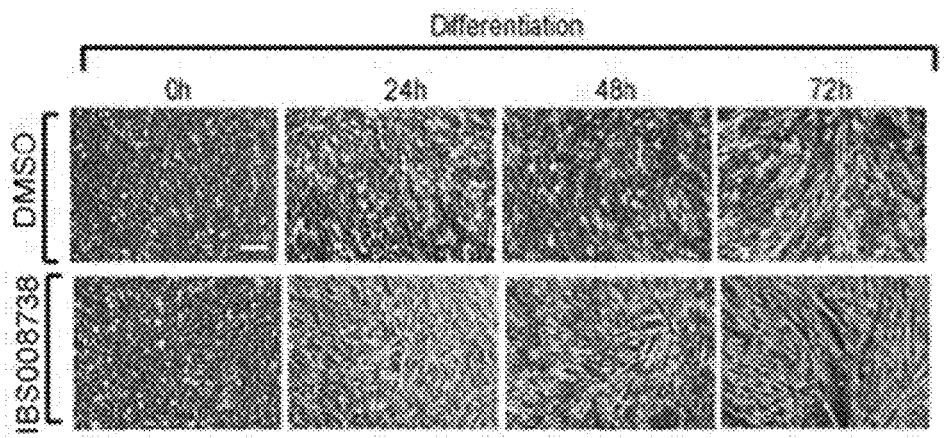
FIG. 2A is a drawing showing the result of evaluation of myogenesis of C2C12 cells.
Figure 2B:
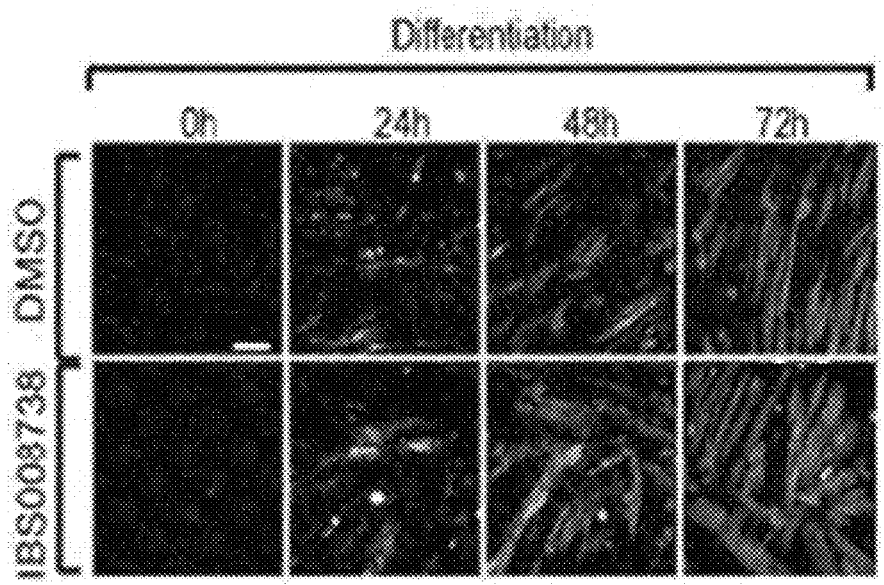
FIG. 2B is a drawing showing the result of evaluation of myogenesis of C2C12 cells.

(2) To a culture medium in which C2C12 cells were grown to confluence under growth condition, IBS008738 or DMSO was added. The C2C12 cells were fixed immediately after the addition of IBS008738 or DMSO, and at 24 hours, 48 hours or 72 hours after the addition of IBS008738 or DMSO under differentiation condition. The fixed C2C12 cells were immunostained with anti-MHC antibody. The cell nuclei were visualized with Hoechst 33342. The results show that cell differentiation and MHC expression were more significant in the case with IBS008738 than in the case with DMSO (see FIGS. 2A and 2B).

Figure 2C:
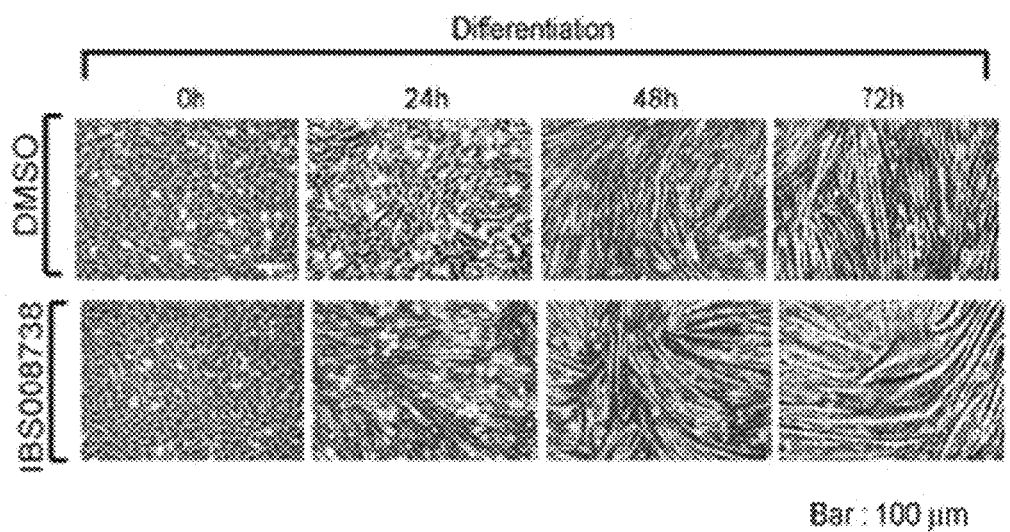
FIG. 2C is a drawing showing the result of evaluation of myogenesis of C2C12 cells.

(3) C2C12 cells were grown under growth condition for 24 hours in a culture medium with IBS008738 or DMSO at a concentration of 10 μM, respectively, and switched to differentiation condition to continue the cultivation. The C2C12 cells were fixed immediately after the completion of cultivation under growth condition, and at 24 hours, 48 hours and 72 hours after the switching to differentiation condition, respectively. As a result, cell differentiation was more developed in the case with IBS008738 than the case with DMSO (see FIG. 2C).

These results show that the specific compound promotes myogenesis of C2C12 cells.

<Melting Point and $^1$H NMR Spectrum of Exemplary Compounds 2 to 44>

Exemplary Compound 2

The compound was obtained as a pale yellow granular crystal by recrystallization from methanol. The melting point was from 165° C. to 165.5° C.

$^1$H NMR (CDCl$_3$): δ 2.24 (3H, s), 5.56 (2H, br), 6.90 (2H, d), 6.94 (2H, d), 7.10 (2H, d), 7.22 (1H, t), 7.32 (2H, q), 7.38 (1H, s)

Exemplary Compound 3

The compound was obtained as a pale yellow granular crystal by recrystallization from hydrous methanol. The melting point was from 141° C. to 142° C.

$^1$H NMR (CDCl$_3$): δ 2.38 (3H, s), 2.57 (3H, s), 2.91 (3H, s), 7.19 (2H, d), 7.20 (2H, c), 7.37 (2H, m), 7.46 (1H, t), 7.53 (1H,$), 7.88 (2H, d), 8.17 (1H, s)

Exemplary Compound 4

The compound was obtained as a yellow granular crystal by recrystallization from methanol. The melting point was from 131.5° C. to 132° C.

$^1$H NMR (CDCl$_3$): δ 2.38 (3H, s), 3.13 (2H, t), 3.22 (2H, t), 7.18 (2H, d), 7.21 (2H, d), 7.36 (2H, t), 7.44 (1H, t), 7.52 (1H, s), 7.86 (2H, d), 8.13 (1H, s)

Exemplary Compound 5

The compound was obtained as a colorless needle-like crystal by recrystallization from methanol. The melting point was from 187° C. to 188° C.

$^1$H NMR (CDCl$_3$): δ 2.22 (3H, s), 2.26 (3H, s), 7.17 (2H, t), 7.30 (1H, t), 7.41 (1H, d), 9.14 (1H, s), 7.61 (1H, s)

Exemplary Compound 6

The compound was obtained as a colorless needle-like crystal by recrystallization from diethyl ether/hexane. The melting point was from 120° C. to 120.5° C.

$^1$H NMR (CDCl$_3$): δ 2.41 (3H, s), 7.23 (2H, d), 7.26 (2H, d), 7.31 (2H, t), 7.40 (1H, t), 7.46 (2H, t), 7.49 (2H, d), 7.60 (1H, t), 7.10 (1H, s), 7.96 (1H, d), 9.13 (1H, s)

Exemplary Compound 7

The compound was obtained as a colorless plate-like crystal by recrystallization from methanol. The melting point was from 124.5° C. to 125° C.

$^1$H NMR (CDCl$_3$): δ 1.13 (3H, t), 2.40 (3H, s), 4.15 (2H, quartet), 4.96 (2H, br), 7.17 (2H, d), 7.23 (2H, d), 7.27 (1H, s)

Exemplary Compound 8

The compound was obtained as a colorless needle-like crystal by recrystallization from methanol. The melting point was from 142.5° C. to 143° C.

$^1$H NMR (CDCl$_3$): δ 1.27 (3H, t), 2.40 (3H, s), 3.09 (3H, s), 3.13 (3H, s), 4.18 (2H, quartet), 7.16 (2H, d), 7.23 (2H, d), 7.36 (1H, s), 8.42 ((1H, s)

Exemplary Compound 9

The compound was obtained as a colorless needle-like crystal by recrystallization from methanol. The melting point was from 167° C. to 168° C.

$^1$H NMR (CDCl$_3$): δ 1.50 (3H, t), 2.43 (3H, s), 4.20 (2H, quartet), 7.18 (2H, d), 7.27 (2H, d), 7.40 (1H, s), 8.68 (1H, d), 9.32 (1H, d)

Exemplary Compound 10

The compound was obtained as a colorless needle-like crystal by recrystallization from methanol. The melting point was from 95° C. to 96° C.

$^1$H NMR (CDCl$_3$): δ 1.19 (3H, t), 2.41 (3H, s), 3.46 (2H, brs), 3.76 (2H, t), 3.83 (2H, brs), 4.16 (2H, q), 7.16 (2H, d), 7.24 (2H, d), 8.46 (1H, s)

Exemplary Compound 11

The compound was obtained as a colorless granular crystal by recrystallization from ethyl acetate. The melting point was from 204° C. to 205° C.

$^1$H NMR (CDCl$_3$): δ 1.22 (3H, t), 2.27 (3H, s), 4.15 (2H, q), 6.99 (2H, d), 7.01 (2H, d), 7.18 (2H, t), 7.32 (2H, t), 7.45 (2H, d), 7.84 (1H, s), 8.84 (1H, s)

Exemplary Compound 12

The compound was obtained as a yellow granular crystal by recrystallization from ethyl acetate. The melting point was from 178° C. to 178.5° C.

$^1$H NMR (CDCl$_3$): δ 2.21 (3H, s), 3.19 (3H, d), 6.83 (2H, d), 6.87 (2H, d), 7.01 (2H, t), 7.14 ((2H, d), 7.19 (2H, d), 7.40 (1H, s)

Exemplary Compound 13

The compound was obtained as a yellow needle-like crystal by recrystallization from methanol. The melting point was from 153° C. to 154° C.

$^1$H NMR (CDCl$_3$): δ 3.72 (3H, s), 5.58 (2H, br), 6.65 (2H, d), 6.94 (2H, d), 7.10 (2H, t), 7.22 (1H, t), 7.30 (2H, d), 7.35 (3H, s)

Exemplary Compound 14

The compound was obtained as a yellow powder by recrystallization from hydrous methanol. The melting point was from 139.5° C. to 140° C.

$^1$H NMR (CDCl$_3$): δ 2.57 (3H, s), 2.92 (3H, s), 3.83 (3H, s), 6.93 (2H, d), 7.24 (2H, d), 7.37 (2H, t), 7.46 (1H, t), 7.50 (1H, s), 7.87 (2H, d), 8.17 (1H, s)

Exemplary Compound 15

The compound was obtained as a yellow granular crystal by recrystallization from ethanol. The melting point was from 137° C. to 138° C.

$^1$H NMR (CDCl$_3$): δ 3.19 (2H, br), 3.29 (2H, br), 3.48 (2H, br), 3.62 (2H, br), 3.83 (3H, s), 6.23 (2H, d), 7.24 (2H, d), 7.36 (2H, t), 7.46 (1H, t), 7.82 (2H, d), 8.16 (3H, s)

Exemplary Compound 16

The compound was obtained as a yellow plate-like crystal by recrystallization from methanol. The melting point was from 197° C. to 197.5° C.

$^1$H NMR (CDCl$_3$): δ 2.30 (3H, s), 2.38 (3H, s), 6.01 (2H, br), 6.94 (2H, d), 7.06 (2H, d), 7.17 (2H, t), 7.29 (1H, t), 7.30 (2H, d)

Exemplary Compound 17

The compound was obtained as a milky-white needle-like crystal by recrystallization from methanol. The melting point was from 224° C. to 226° C.

$^1$H NMR (CDCl$_3$): δ 6.57 (2H, br), 6.91 (2H, d), 7.16 (2H, t), 7.28 (2H, d), 7.29 (1H, t), 7.34 (2H, d), 7.39 (1H, s)

Exemplary Compound 18

The compound was obtained as a yellow granular crystal by recrystallization from diethyl ether/hexane. The melting point was from 170° C. to 171° C.

$^1$H NMR (CDCl$_3$): δ 2.31 (3H, s), 2.80 (3H, s), 2.81 (3H, s), 7.05 (2H, d), 7.16 (2H, d), 7.33 (2H, t), 7.40 (1H, t), 7.16 (2H, d), 7.90 (1H, s)

Exemplary Compound 19

The compound was obtained as a yellow rod-like crystal by recrystallization from ethanol/hexane. The melting point was from 154° C. to 154.5° C.

$^1$H NMR (CDCl$_3$): δ 2.57 (3H, s), 2.94 (3H, s), 7.19 (2H, d), 7.38 (2H, t), 7.49 (1H, t), 7.54 (2H, d), 7.89 (2H, d), 8.20 (1H, s)

Exemplary Compound 20

The compound was obtained as a yellow rod-like crystal by recrystallization from ethanol. The melting point was from 170° C. to 171° C.

$^1$H NMR (CDCl$_3$): δ 3.19 (1H, t), 3.31 (1H, t), 3.48 (1H, t), 3.63 (1H, t), 7.19 (2H, d), 7.38 (2H, t), 7.49 (1H, t), 7.54 (1H, s), 7.55 (2H, d), 7.84 (2H, d), 8.19 (1H, s)

Exemplary Compound 21

The compound was obtained as a yellow granular crystal by recrystallization from methanol. The melting point was from 145.5° C. to 146° C.

$^1$H NMR (CDCl$_3$): δ 0.90 (3H, t), 1.21 (2H, m), 1.31 (2H, m), 1.49 (2H, quint), 2.48 (2H, t), 5.63 (2H, br), 6.90 (4H, d), 7.06 (2H, t), 7.17 (1H, t), 7.29 (2H, d), 7.39 (1H, s)

Exemplary Compound 22

The compound was obtained as a yellow needle-like crystal by recrystallization from methanol. The melting point was from 95.5° C. to 96.5° C.

$^1$H NMR (CDCl$_3$): δ 0.90 (3H, t), 1.33 (4H, m), 1.61 (2H, quint), 2.57 (3H, s), 2.62 (2H, t), 3.18 (2H, brs), 2.92 (2H, s), 7.21 (4H, s), 7.37 (2H, t), 7.46 (1H, t), 7.54 (1H, s), 7.88 (2H, d), 8.18 (1H, s)

Exemplary Compound 23

The compound was obtained as a yellow granular crystal by recrystallization from diethyl ether. The melting point was from 101° C. to 101.5° C.

$^1$H NMR (CDCl$_3$): δ 0.89 (3H, t), 1.33 (4H, m), 1.62 (2H, quint), 2.62 (2H, t), 3.18 (2H, brs), 3.29 (2H, brs), 3.48 (2H, brs), 3.62 (2H, brs), 7.20 (2H, d), 7.22 (2H, d), 7.36 (2H, t), 7.46 (1H, t), 7.55 (3H, s), 7.84 (2H, d), 8.17 (1H, s)

Exemplary Compound 24

The compound was obtained as a milky-white rhombic crystal by recrystallization from methanol. The melting point was from 193° C. to 196° C.

$^1$H NMR (CDCl$_3$): δ 1.79 (3H, s), 2.44 (3H, s), 5.73 (2H, br), 7.21 (1H, s), 7.23 (2H, d), 7.30 (2H, d)

Exemplary Compound 25

The compound was obtained as a pale yellow needle-like crystal by recrystallization from methanol. The melting point was from 150° C. to 151.5° C.

$^1$H NMR (CDCl$_3$): δ 2.40 (3H, s), 2.65 (3H, s), 3.10 (3H, s), 3.12 (3H, s), 7.13 (2H, d), 7.21 (2H, d), 7.35 (1H, s), 8.49 (1H, s)

Exemplary Compound 26

The compound was obtained as a milky-white powder by recrystallization from methanol. The melting point was from 184° C. to 185° C.

$^1$H NMR (CDCl$_3$): δ 2.34 (3H, s), 6.13 (2H, br), 7.34 (2H, d), 7.38 (2H, d), 7.81 (1H, s)

Exemplary Compound 27

The compound was obtained as a yellow powder by recrystallization from methanol. The melting point was from 149° C. to 150.5° C.

$^1$H NMR (CDCl$_3$): δ 1.47 (9H, s), 2.68 (2H, t), 3.26 (2H, m), 4.33 (1H, br), 5.67 (2H, br), 6.94 (4H, s), 7.08 (2H, t), 7.22 (1H, t), 7.28 (2H, d), 7.39 (1H, s)

Exemplary Compound 28

The compound was obtained as a pale yellow needle-like crystal by recrystallization from ethanol/hexane. The melting point was from 151° C. to 153.5° C.

$^1$H NMR (CDCl$_3$): δ 2.36 (2H, t), 2.85 (2H, t), 5.56 (2H, br), 6.95 (4H, s), 7.08 (2H, t), 7.19 (1H, t), 7.29 (2H, d), 7.40 (1H, s)

Exemplary Compound 29

The compound was obtained as a yellow granular crystal by recrystallization from ethyl acetate. The melting point was from 174° C. to 175° C.

$^1$H NMR (CDCl$_3$): δ 3.66 (2H, s), 5.53 (2H, br), 7.06 (2H, d), 7.13 (2H, d), 7.10 (2H, d), 7.14 (2H, t), 7.27 (1H, t), 7.34 (2H, d), 7.1 (1H, s)

Exemplary Compound 30

The compound was obtained as a colorless rod-like crystal by recrystallization from methanol. The melting point was from 141.5° C. to 142° C.

$^1$H NMR (CDCl$_3$): δ 2.27 (3H, s), 3.75 (3H, s), 5.36 (2H, br), 6.64 (2H, d), 6.95 (2H, d), 6.99 (2H, d), 7.32 (2H, d), 7.39 (1H, s)

Exemplary Compound 31

The compound was obtained as a yellow rhombic crystal by recrystallization from methanol. The melting point was from 180° C. to 181.5° C.

$^1$H NMR (CDCl$_3$): δ 2.25 (3H, s), 5.76 (2H, br), 6.89 (2H, d), 6.96 (2H, d), 7.03 (1H, t), 7.15 (2H, d), 7.16 (1H, s), 7.20 (2H, d), 7.38 (1H, s)

Exemplary Compound 32

The compound was obtained as a colorless rod-like crystal by recrystallization from methanol. The melting point was from 210° C. to 212° C.

$^1$H NMR (CDCl$_3$): δ 2.28 (3H, s), 5.67 (2H, br), 6.87 (2H, d), 6.96 (2H, d), 7.04 (2H, d), 7.21 (2H, d), 7.37 (1H, s)

Exemplary Compound 33

The compound was obtained as a yellow granular crystal by recrystallization from methanol. The melting point was from 276° C. to 278° C.

$^1$H NMR (CDCl$_3$): δ DMSO 2.13 (3H, s), 6.84 (2H, br), 6.92 (2H, d), 6.96 (2H, d), 7.42 (2H, d), 7.79 (1H, s), 7.88 (2H, d)

Exemplary Compound 34

The compound was obtained as a colorless plate-like crystal by recrystallization from methanol. The melting point was from 198.5° C. to 199° C.

$^1$H NMR (CDCl$_3$): δ 2.27 (3H, s), 5.63 (2H, br), 6.76 (2H, t), 6.89 (2H, d), 6.96 (2H, d), 7.32 (2H, q), 7.38 (1H, s)

Exemplary Compound 35

The compound was obtained as a pale yellow granular crystal by recrystallization from methanol. The melting point was from 226° C. to 228° C.

$^1$H NMR (CDCl$_3$): δ 2.24 (3H, s), 5.56 (2H, br), 6.90 (2H, d), 6.94 (2H, d), 7.10 (2H, d), 7.22 (1H, t), 7.32 (2H, q), 7.38 (1H, s)

Exemplary Compound 36

The compound was obtained as a yellow granular crystal by recrystallization from methanol. The melting point was from 216° C. to 218° C.

$^1$H NMR (CDCl$_3$): δ 2.29 (3H, s), 5.69 (2H, br), 6.86 (2H, d), 6.96 (2H, d), 7.14 (2H, d), 7.20 (2H, d), 7.38 (1H, s)

Exemplary Compound 37

The compound was obtained as a pale yellow plate-like crystal by recrystallization from methanol. The melting point was from 154° C. to 155.5° C.

$^1$H NMR (CDCl$_3$): δ 1.50 (3H, br), 1.64 (3H, br), 1.76 (6H, br), 1.91 (3H, br), 2.45 (3H, s), 5.08 (2H, br), 7.20 (2H, d), 7.30 (2H, d), 7.31 (1H, s)

Exemplary Compound 38

The compound was obtained as a milky-white prism-like crystal by recrystallization from methanol. The melting point was from 155° C. to 156° C.

$^1$H NMR (CDCl$_3$): δ 5.75 (2H, brs), 6.72 (2H, dd), 7.03 (1H, ddd), 7.14 (2H, t), 7.24 (1H, t), 7.34 (1H, ddd), 7.42 (2H, d), 7.85 (1H, s), 8.32 (1H, dd)

Exemplary Compound 39

The compound was obtained as a pale yellow prism-like crystal by recrystallization from methanol. The melting point was from 234.5° C. to 235.5° C.

$^1$H NMR (CDCl$_3$): δ 5.54 (2H, brs), 7.16 (2H, d), 7.18 (2H, t), 7.32 (1H, t), 7.38 (2H, d), 7.47 (1H, s), 7.48 (2H, d)

Exemplary Compound 40

The compound was obtained as a colorless prism-like crystal by recrystallization from methanol. The melting point was from 103° C. to 104° C.

$^1$H NMR (CDCl$_3$): δ 1.02 (3H, t), 2.10 (3H, s), 4.08 (2H, m), 4.96 (2H, brs), 7.17 (2H, d), 7.19 (1H, s), 7.25 (1H, t), 7.28 (1H, d), 7.35 (1H, t)

Exemplary Compound 41

The compound was obtained as a colorless prism-like crystal by recrystallization from ethyl acetate. The melting point was from 161° C. to 163° C.

$^1$H NMR (CDCl$_3$): δ 2.14 (3H, s), 5.75 (2H, brs), 7.15 (1H, s), 7.28 (1H, dd), 7.34 (1H, ddd), 7.36 (1H, dd), 7.43 (1H, ddd)

Exemplary Compound 42

The compound was obtained as a milky-white granular crystal by recrystallization from diethyl ether/hexane. The melting point was from 75° C. to 76° C.

$^1$H NMR (CDCl$_3$): δ 1.46 (3H, br), 1.60 (3H, br), 1.71 (6H, br), 1.88 (3H, br), 2.10 (3H, s), 5.19 (2H, brs), 7.2-7.35 (4H, m)

Exemplary Compound 43

The compound was obtained as a yellow granular crystal by recrystallization from methanol. The melting point was from 145° C. to 147° C.

$^1$H NMR (CDCl$_3$): δ 2.00 (3H, s), 2.22 (3H, s), 5.45 (2H, brs), 6.79 (1H, s), 6.85 (1H, dd), 6.92 (1H, dd), 7.10 (2H, t), 7.22 (1H, t), 7.24 (1H, s), 7.28 (2H, d)

Exemplary Compound 44

The compound was obtained as a yellow granular crystal by recrystallization from methanol. The melting point was from 190° C. to 191° C.

$^1$H NMR (CDCl$_3$): δ 1.99 (6H, s), 2.20 (3H, s), 5.36 (2H, brs), 6.71 (2H, s), 7.13 (2H, t), 7.15 (1H, s), 7.24 (1H, t), 7.26 (2H, d)

<Evaluation of Muscle Differentiation by Immunoblotting and Immunostaining>

(1) C2C12 cells were cultured for 24 hours under growth condition in a culture medium added with IBS008738 or DMSO at a concentration of 10 μM, and switched to differentiation condition and the cultivation was continued.

Figure 3A:
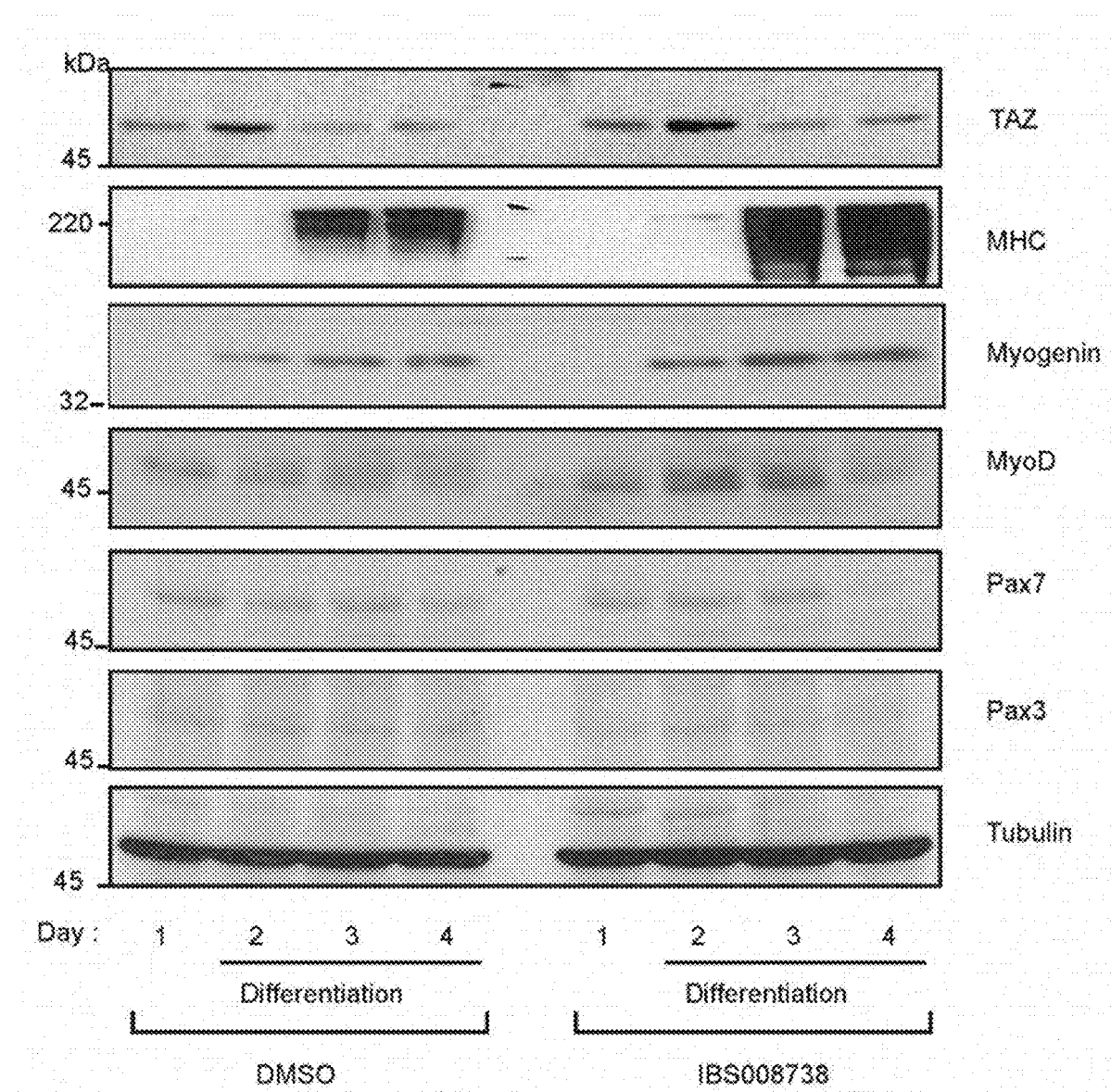
FIG. 3A is a drawing showing the result of evaluation of muscle differentiation by immunoblotting.

The expression of markers indicating muscle differentiation was determined with a predetermined antibody, on the C2C12 cells immediately after the completion of cultivation under growth condition (0 h), 24 hours after switching to differentiation condition (24 h), 48 hours after switching to differentiation condition (48 h) and 72 hours after switching to differentiation condition (72 h), respectively. Tubulin was used as a loading control (FIG. 3A).

The expression of MyoD on day 1 after the addition of IBS008738 was slightly higher than the case in which DMSO was added, suggesting the possibility that IBS008738 contributes to the expression of MyoD. The expression of MyoD became significant on days 2 and 3, and declined on day 4. The expression of myogenin was observed from day 2 in both cases with IBS008738 and DMSO, and became stronger after day 2 in the case with IBS008738. The expression of MHC started to be visible on day 2 and became significant on days 3 and 4 as compared to the case with DMSO. The expression of TAZ in the case with IBS008738 became most significant on day 2. It was faster to decrease in the expression of Pax7 in IBS008738 than DMSO, but not in Pax3.

Figure 3B:
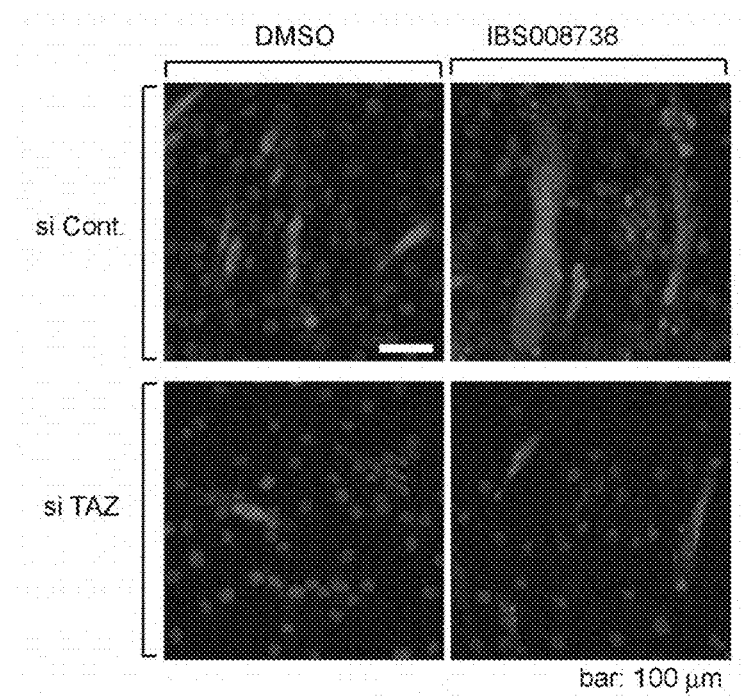
FIG. 3B is a drawing showing the result of evaluation of muscle differentiation by immunoblotting.
Figure 3C:
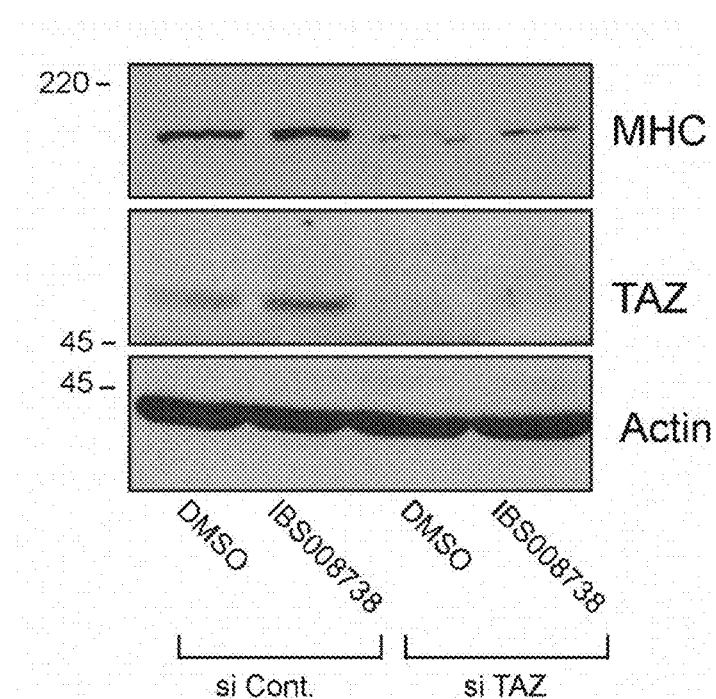
FIG. 3C is a drawing showing the result of evaluation of muscle differentiation by immunoblotting.
Figure 4:
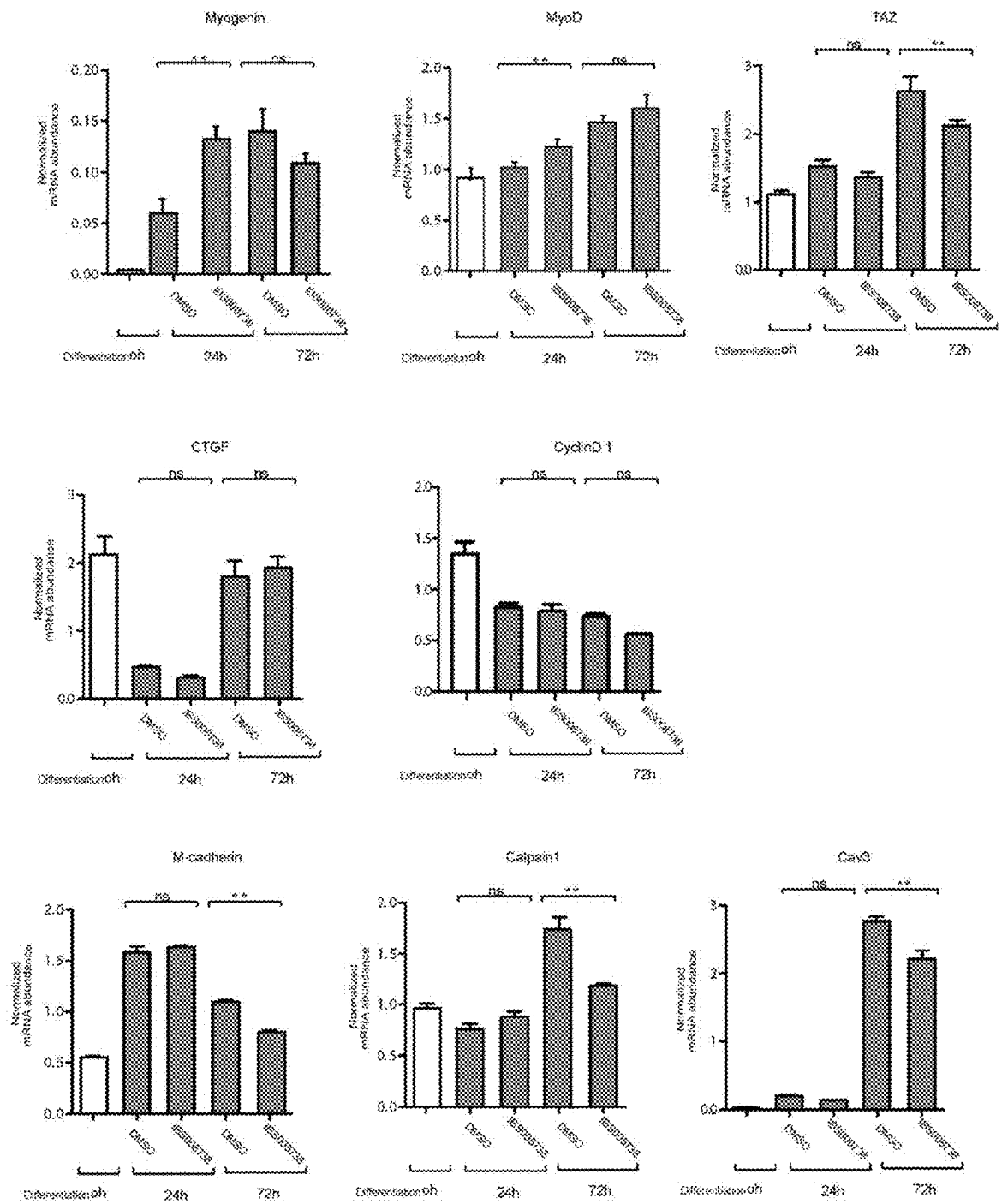
FIG. 4 is a drawing showing the result of evaluation of muscle differentiation by quantitative real-time PCR.

(2) C2C12 cells with TAZ knocked down by a method described in Sci Signal 2:ra59 (si TAZ) and C2C12 cells with TAZ not knocked down (si Cont) were cultured for 72 hours in a culture medium added with IBS008738 or DMSO at a concentration of 10 μM, respectively, and were immunostained with an anti-MHC antibody (the white portion in FIG. 3B, the bar is 100 μm). Further, immunoblotting was performed with an anti-MHC antibody and an anti-TAZ antibody (see FIG. 3C). The loss of expression of TAZ indicates that TAZ is effectively knocked down. Further, the expression of MHC was lost by the knockdown of TAZ. In the C2C12 cells in which TAZ was not knocked down (si Cont), IBS008738 promoted muscle formation, whereas not in the C2C12 cells in which TAZ was knocked down (si TAZ).

<Evaluation of Muscle Formation and Muscle Fusion Markers by Quantitative Real-Time PCR>

(1) Quantitative real-time PCR was performed with C2C12 cells immediately before the induction of muscle formation (0 h), and after culturing under differentiation condition in a culture medium added with IBS008738 or DMSO at a concentration of 10 μM for 24 hours (24 h) and 72 hours (72 h), respectively. The evaluation was performed three times, and the results are shown in Tables 3 and 4. The results show that the degree of gene transcription of myogenin and MyoD was higher in the case with IBS008738 than the case with DMSO, but no significant difference between the cases after 72 hours. On the other hand, expression of TAZ did not change. The line and error bar indicate the average value and the standard error, **$p<0.05$, and ns refers to not significant.

(2) Evaluation was also performed under the same condition on the connective tissue growth factor (CTGF) and cyclin D1, as TAZ targets in epidermal cells. As a result, there was no significant difference between the case with IBS008738 and the case with DMSO.

Evaluation was also performed under the same condition on M-cadherin, calpain 1 and caveolin 3, which are myofusion markers. As a result, there was no increase in the degree of gene transcription in the case with IBS008738.

TABLE 3

| | | Normalized mRNA abundance | | | | |
|---|---|---|---|---|---|---|
| | | 0 h | 24 h-DMSO | 24 h-IBS008738 | 72 h-DMSO | 72 h-IBS008738 |
| myogenin | 1 | 0.00 | 0.08 | 0.14 | 0.18 | 0.10 |
| | 2 | 0.00 | 0.04 | 0.11 | 0.10 | 0.10 |
| | 3 | 0.01 | 0.06 | 0.15 | 0.14 | 0.13 |
| myoD | 1 | 0.98 | 1.03 | 1.22 | 1.49 | 1.72 |
| | 2 | 0.93 | 1.05 | 1.27 | 1.45 | 1.55 |
| | 3 | 0.78 | 0.96 | 1.29 | 1.39 | 1.49 |
| TAZ | 1 | 0.70 | 0.95 | 0.88 | 1.67 | 1.44 |
| | 2 | 0.73 | 1.05 | 0.88 | 1.90 | 1.36 |
| | 3 | 0.76 | 1.02 | 0.94 | 1.65 | 1.41 |
| CTGF | 1 | 1.98 | 0.45 | 0.32 | 1.94 | 1.76 |
| | 2 | 2.43 | 0.44 | 0.30 | 1.89 | 2.01 |
| | 3 | 2.05 | 0.43 | 0.25 | 1.54 | 2.04 |
| CyclinD1 | 1 | 1.56 | 0.93 | 0.95 | 0.79 | 0.62 |
| | 2 | 1.35 | 0.89 | 0.83 | 0.80 | 0.60 |
| | 3 | 1.44 | 0.87 | 0.78 | 0.79 | 0.61 |
| M-cadherin | 1 | 0.58 | 1.46 | 1.66 | 1.11 | 0.82 |
| | 2 | 0.52 | 1.64 | 1.61 | 1.11 | 0.87 |
| | 3 | 0.55 | 1.64 | 1.64 | 1.06 | 0.80 |
| Calpain1 | 1 | 1.04 | 0.64 | 0.84 | 1.85 | 1.15 |
| | 2 | 0.88 | 0.77 | 0.81 | 1.72 | 1.18 |
| | 3 | 0.96 | 0.82 | 0.98 | 1.59 | 1.22 |
| Caveolin3 | 1 | 0.01 | 0.20 | 0.14 | 2.65 | 2.08 |
| | 2 | 0.04 | 0.18 | 0.13 | 2.89 | 2.47 |
| | 3 | 0.02 | 0.22 | 0.14 | 2.78 | 2.09 |

The quantitative real-time PCR was performed with SYBER Green (Roche) and ABI7500 Realtime PCR system (Applied Biosystems). The gene sequence of the primers used for the PCR are shown in Table 4.

TABLE 4

| Target Gene | No. | Sense | No. | Antisense |
|---|---|---|---|---|
| Human LATS1 | 1 | 5'-gtccttc gtgtgggcta cat-3' | 2 | 5'-cgaggat cttcggttga cat-3' |
| Human LATS2 | 3 | 5'-ttcatcc accgagacat caa-3' | 4 | 5'-ctccatg ctgtcctgtc tga-3' |
| Human TAZ | | | | |
| Mouse TAZ | 5 | 5'-ccatggc agtgtcccag ccg-3' | 6 | 5'-ggcaggc gtgttgacag ggg-3' |
| Mouse Cav3 | 7 | 5'-cgcgacc ccaagaacat caat-3' | 8 | 5'-caccgtc gaagctgtag gt-3' |
| Mouse Calpain1 | 9 | 5'-ggtgaag tggagtggaa agg-3' | 10 | 5'-tgccctc gtaaaatgtg gta-3' |
| Mouse M-cadherin | 11 | 5'-cccaact aaggggctct ctc-3' | 12 | 5'-attctcc caccactcct gact-3' |
| Mouse CTGF | 13 | 5'-tgacctg caggaaaaca ttaaga-3' | 14 | 5'-agccctg tatgtcttca cactg-3' |
| Mouse CyclinD1 | 15 | 5'-agacctg tgcgccctcc gta-3' | 16 | 5'-tttgcag cagctcctcg ggc-3' |
| Mouse MyoD | 17 | 5'-actttct ggagccctcc tggca-3' | 18 | 5'-tttgttg cactacacag catg-3' |

TABLE 4-continued

| Target Gene | No. | Sense | No. | Antisense |
|---|---|---|---|---|
| Mouse Myogenin | 19 | 5'-tacaggc cttgctcagc tc-3' | 20 | 5'-tgtggga gttgcattca ctg-3' |
| Mouse GAPDH | 21 | 5'-aactttg gcattgtgga agg-3' | 22 | 5'-acacatt gggggtagga aca-3' |
| Mouse CTGF ChIP | 23 | 5'-cttcttg gtgttgtgct gga-3' | 24 | 5'-gattgat cctgacccct tga-3' |
| Mouse Myf5 ChIP | 25 | 5'-aggcatg actaattgca tggtaactc g-3' | 26 | 5'-ctcataa tgatatggct tttaagccc c-3' |
| Mouse Myogenin ChIP | 27 | 5'-aaggaga gggaaggga atca-3' | 28 | 5'-tagccaa cgccacagaa acc-3' |

<Evaluation of Activity of Transcription Factors by Reporter Assay>

Figure 5:
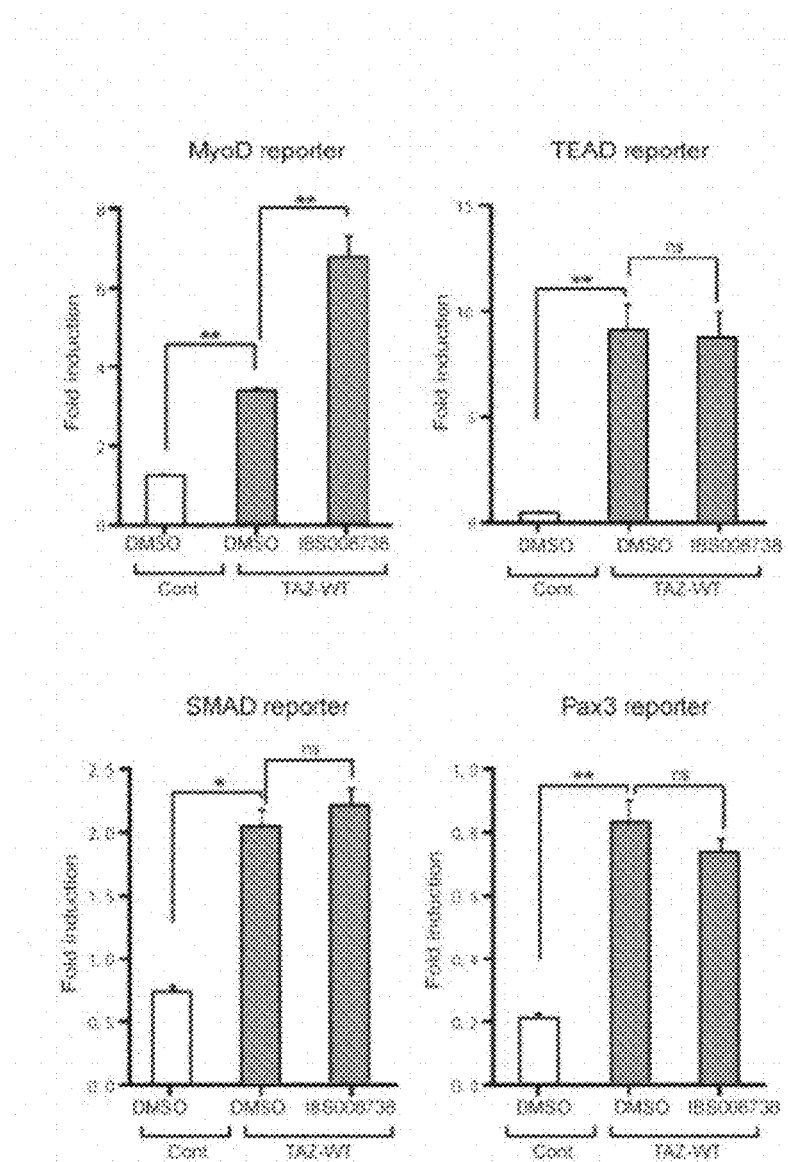
FIG. 5 is a drawing showing the result of evaluation by reporter assay.

The effect and its degree on the activity of a reporter, derived from a transcription factor that interacts with TAZ in C2C12 cells, were evaluated. Specifically, C2C12 cells expressing luciferase reporters corresponding to MyoD, TEAD, SMAD and Pax3 and C2C12 cells expressing these luciferase reporters and TAZ were cultured in a culture medium added with IBS008738 or DMSO at a concentration of 10 µM, respectively. The assay was performed three times, and the results are shown in FIG. 5 and Table 5. The results show a tendency that overexpression of TAZ enhances the activity of reporters of MyoD, TEAD, SMAD and Pax3. In the case with IBS008738, the activity of the reporter of MyoD showed a significant increase. However, the activity of the reporters of TEAD, SMAD and Pax3 did not show a significant difference from the case with DMSO. The line and the error bar indicate the average value and the standard error, $*p<0.05$, $**p<0.01$, ns refers to not significant.

TABLE 5

| | | Fold induction | | |
|---|---|---|---|---|
| | | Control | TAZ WT-DMSO | TAZ WT-IBS008738 |
| MyoD reporter | 1 | 1.25 | 3.50 | 6.92 |
| | 2 | | 3.39 | 7.63 |
| | 3 | | 3.35 | 5.87 |
| TEAD reporter | 1 | 0.42 | 7.45 | 6.84 |
| | 2 | | 8.08 | 10.82 |
| | 3 | | 11.38 | 8.41 |
| Pax3 reporter | 1 | 0.20 | 0.96 | 0.80 |
| | 2 | | 0.79 | 0.65 |
| | 3 | | 0.72 | 0.74 |
| SMAD reporter | 1 | 0.72 | 2.12 | 2.09 |
| | 2 | | 2.17 | 2.01 |
| | 3 | | 1.83 | 2.47 |

Transfection of the luciferase reporters was performed to the C2C12 cells after being plated at 12-well plates ($1 \times 10^5$ cells/well) and cultured overnight. As the luciferase reporters, pGL3 Myo-184- (MyoD-), 8×GT-IIC-δ51LucII- (TEAD-), 9×CAGA-MLP-(SMAD-), and p(PRS-1/-4)3- (Pax3-) were transfected to the cells alone or with TAZ. These reporter vectors were from Keiji Miyazawa (Yamanashi University), Hiroshi Sasaki (Kumamoto University) and Hiroki Kurihara (The University of Tokyo).

Immediately after the transfection, DMSO or IBS008738 was added at a concentration of 10 µM, respectively. After growing the cells to confluence, the cells were transferred to a differentiation medium with DMSO or IBS008738, and cultured for 24 hours before the luciferase assay.

<Chromatin Immunoprecipitation Analysis>

Figure 6:
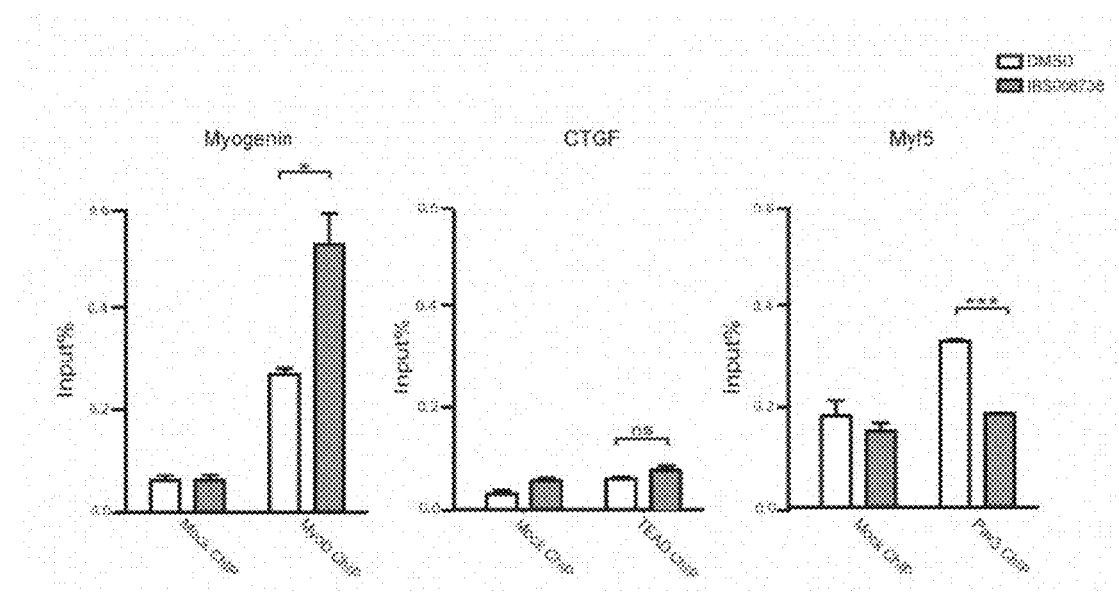
FIG. 6 is a drawing showing the result of evaluation by chromatin immunoprecipitation.

(1) Chromatin immunoprecipitation of MyoD, TEAD and Pax3 was performed on C2C12 cells that were cultured under differentiation condition for 24 hours in a culture medium added with IBS008738 or DMSO at a concentration of 10 µM. Myogenin, connective tissue growth factor (CTGF) and Myf5 were detected by PCR, respectively. The immunoprecipitation with protein G sepharose was used as a control (Mock ChIP). The test was performed three times, and the results are shown in Table 6 and FIG. 6. The results show that binding of MyoD to myogenin promoter became significant by IBS008738, but the effects on association of TEAD with CTGF was little, and the binding of Pax3 to Myf5 promoter was lower than the case with DMSO. The line and the error bar in the figure indicate the average value and the standard error, $*p<0.05$, $***p<0.001$, ns refers to not significant.

TABLE 6

| | | Input % | | | | | |
|---|---|---|---|---|---|---|---|
| | | DMSO | | | IBS008738 | | |
| | | 1 | 2 | 3 | 1 | 2 | 3 |
| myogenin-p | Mock ChIP | 0.04 | 0.07 | 0.08 | 0.05 | 0.05 | 0.08 |
| | myoD ChIP | 0.29 | 0.28 | 0.25 | 0.53 | 0.59 | 0.47 |
| CTGF-p | Mock ChIP | 0.02 | 0.04 | 0.02 | 0.06 | 0.06 | 0.04 |
| | TEAD ChIP | 0.06 | 0.05 | 0.06 | 0.06 | 0.08 | 0.09 |
| Myf5-p | Mock ChIP | 0.21 | 0.15 | 0.17 | 0.14 | 0.13 | 0.16 |
| | PAX3 ChIP | 0.32 | 0.32 | 0.33 | 0.19 | 0.18 | 0.18 |

Figure 7A:
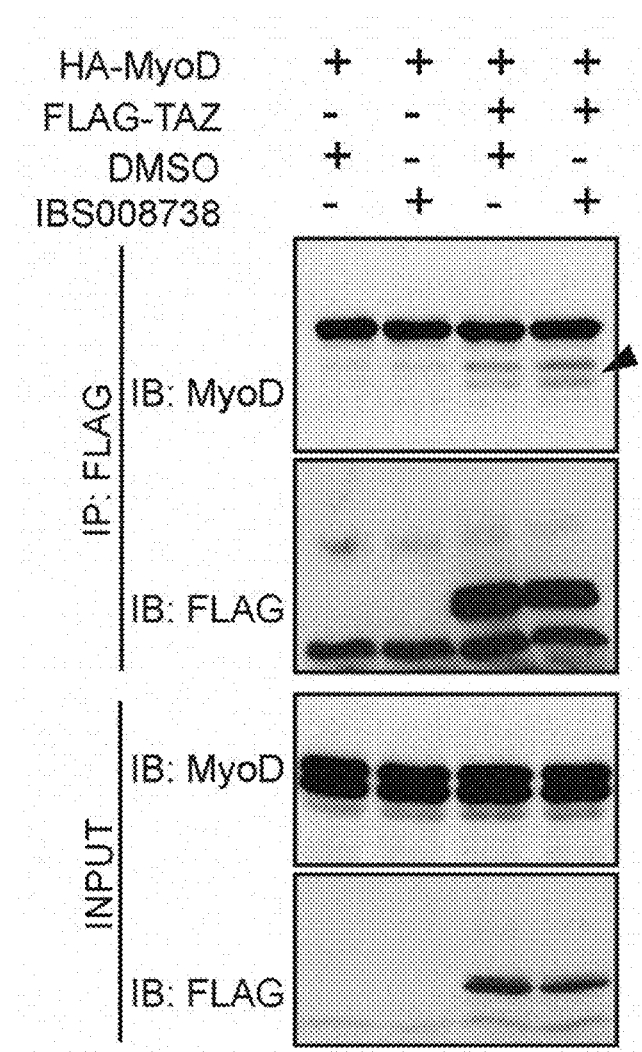
FIG. 7A is a drawing showing the result of evaluation by immunoprecipitation method.

(2) For analyzing the effects of IBS008738 on the interaction of TAZ and MyoD, immunoprecipitation was performed on human embryonic kidney cells (HEK 293) expressing FLAG-TAZ and HA-MyoD, with anti-FLAF M2 beads. As a result, interaction of TAZ and MyoD was slightly promoted in the case treated with IBS008738, as compared with the case treated with DMSO (see the arrow in FIG. 7A).

The Chromatin immunoprecipitation was performed according to the following process. C2C12 cells were cultured to confluence, and then treated with IBS008738 or DMSO at a concentration of 10 µM in a differentiation medium for 24 hours. The cells were crosslinked in 1.42% (v/v) formaldehyde for 15 minutes, and the reaction was quenched by treating with 125 mM glycine for 5 minutes. The crosslinked cells were lysed in a buffer (50 mM Tris-HCl pH7.5, 150 mM NaCl, 5 mM EDTA, 0.5% (v/v) Nonidet P-40, and 1% (v/v) Triton X-100) and chromatin was sheared in a sonicator bath (Bioruptor, Diagenode) for 25 consecutive rounds at the maximum output and 30 sec on/60 sec off cycles. Shearing was analyzed by agarose gel electrophoresis. Chromatin obtained from about $2 \times 10^6$ cells was incubated for 3 hours at 4° C. with 2 µg antibodies. Then, immunoprecipitation was performed with 20 µl protein G sepharose beads. Protein G sepharose without antibody was used as a control (Mock ChIP). The immunoprecipitated DNA fragments were isolated using Chelex-100 resin and diluted by 1:2.5 for quantitative PCR analysis. Input normalized relative abundance was determined.

<Evaluation by Immunofluorescence Method>

Figure 7B:
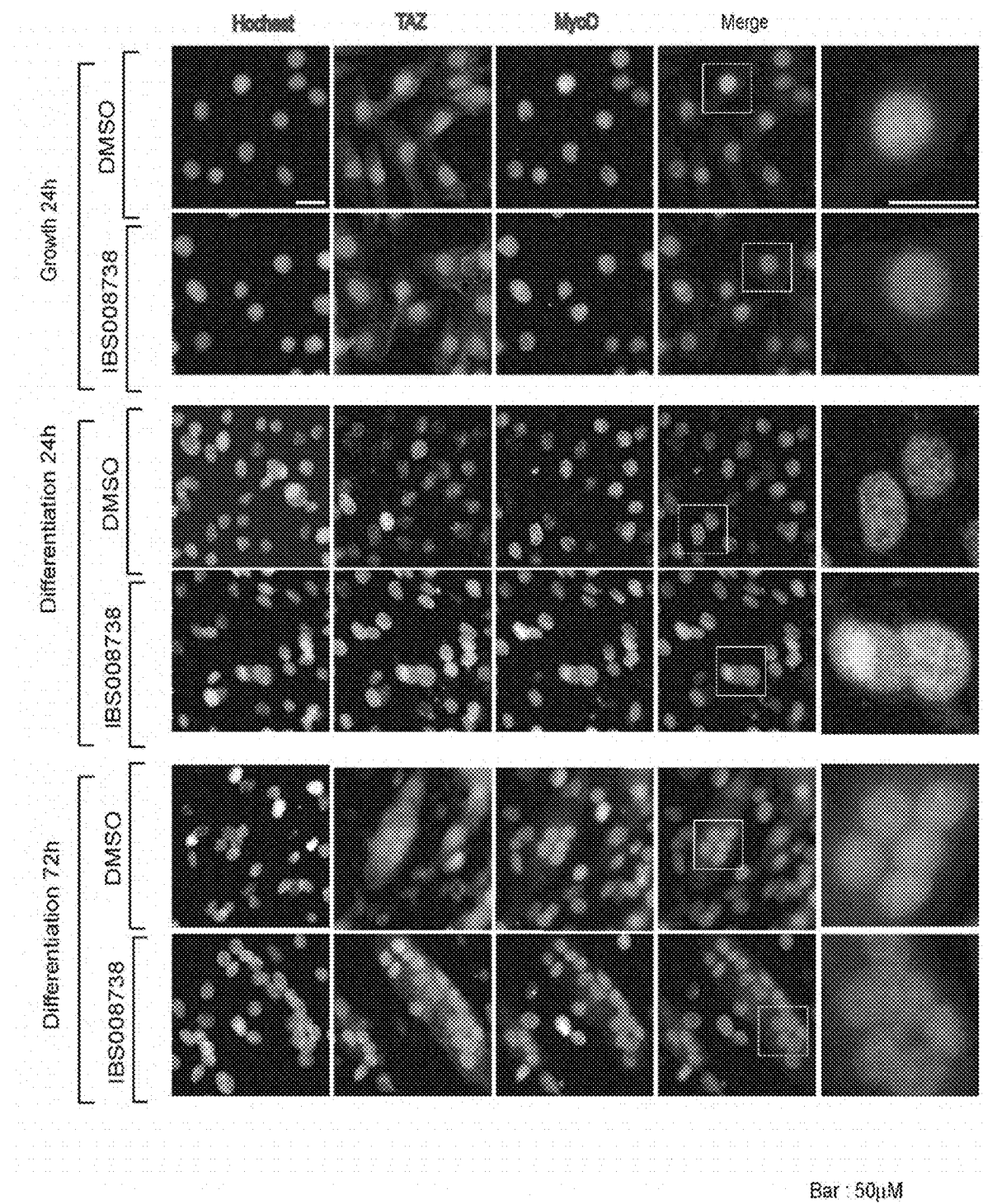
FIG. 7B is a drawing showing the result of evaluation by immunofluorescent method.

Immunostaining of endogenous MyoD and TAZ in C2C12 cells was performed at three stages, i.e., after being cultured in a medium added with IBS008738 or DMSO at a concentration of 10 µM under growth condition for 24 hours, after being cultured under differentiation condition for 24 hours, and after being cultured under differentiation condition for 72 hours (see FIG. 7B). Both MyoD and TAZ existed at each of the three stages. After being cultured under growth condition for 24 hours, MyoD and TAZ were diffusely distributed in the nuclei (top), but formed dots under differentiation condition. After being cultured under differentiation condition for 24 hours, some cells strongly expressed TAZ, whereas other cells expressed more MyoD (middle). After being cultured under differentiation condition for 72 hours, in the single-nuclear cells, TAZ expression decreased while MyoD was still expressed. In the multi-nuclear cells, both TAZ and MyoD were expressed and colocalized in the nuclei (bottom). In the case with IBS008738, no significant difference from the case with DMSO was not observed in the growth condition. However, at 24 hours under differentiation condition, colocalization of TAZ and MyoD in the single-nuclear cells and generation of cells with two or three nuclei were promoted in the case with IBS008738 as compared with the case with DMSO (middle). At 72 hours under differentiation condition, multinuclear cells were remarkably increased in the case with IBS008738 as compared with the case with DMSO (bottom). The immunostaining and the immunofluorescence analysis were performed by the method described in Exp Cell Res 313:1484-1495. The line in the figures is 50 µm.

<Antagonistic Action on Myostatin>

Figure 8A:
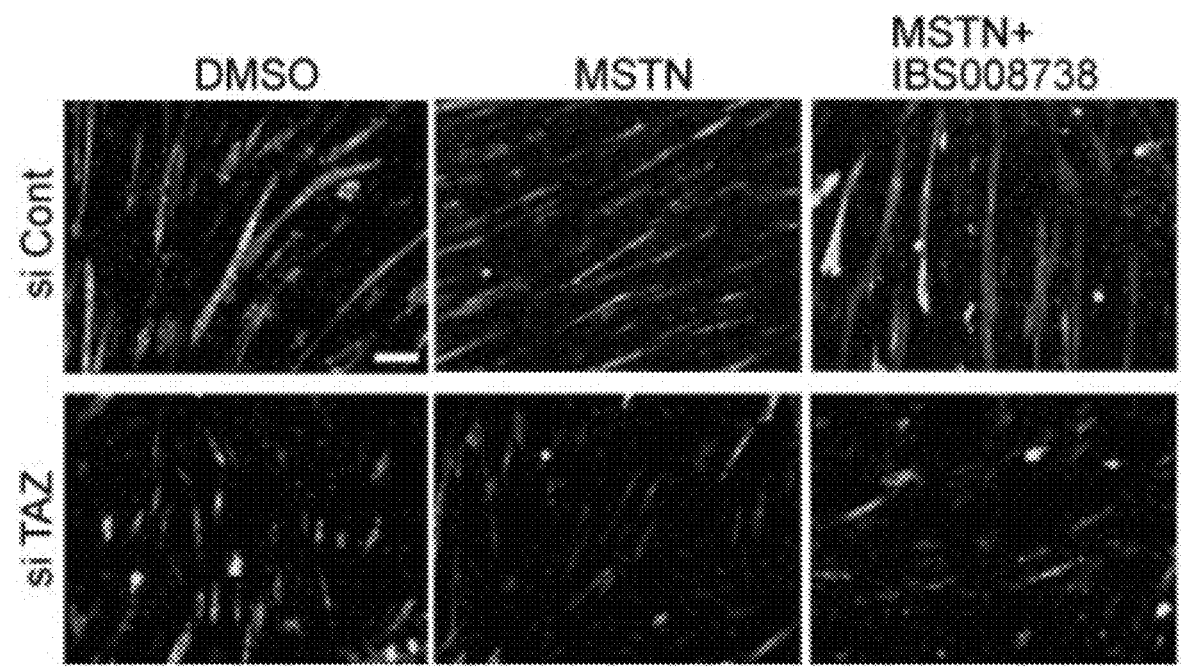
FIG. 8A is a drawing showing the result of evaluation of antagonistic action on myostatin.
Figure 8B:
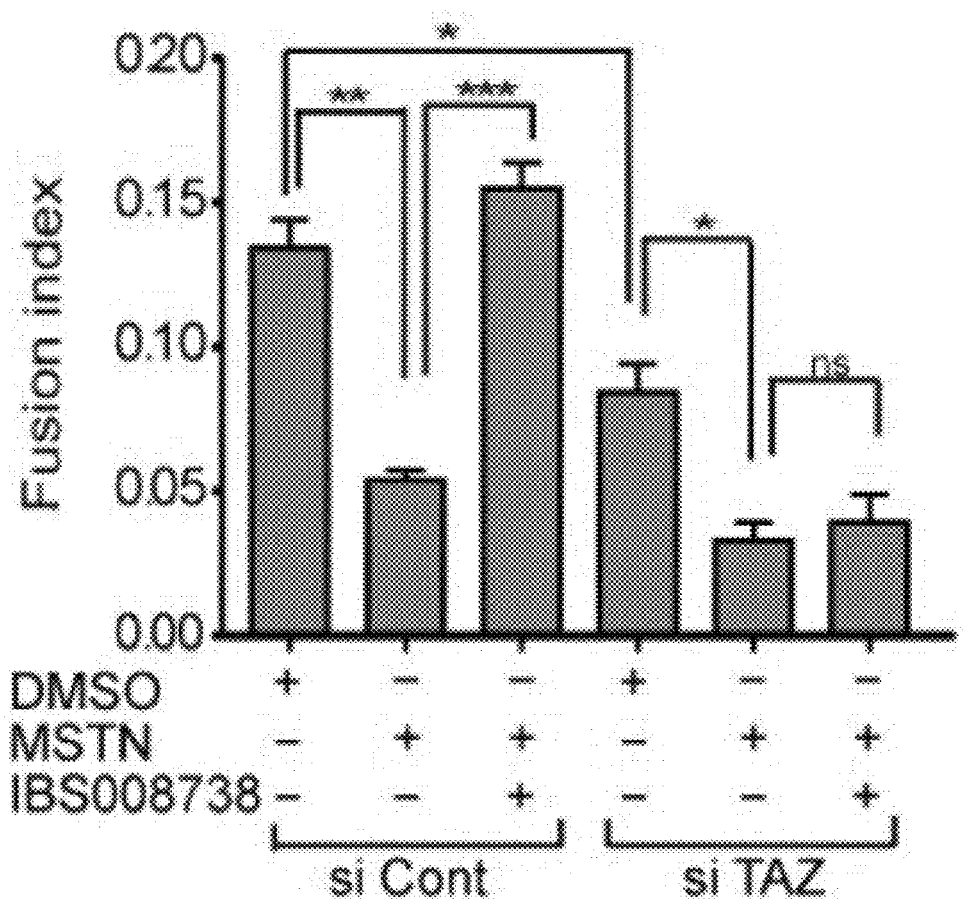
FIG. 8B is a drawing showing the result of evaluation of antagonistic action on myostatin.
Figure 8C:
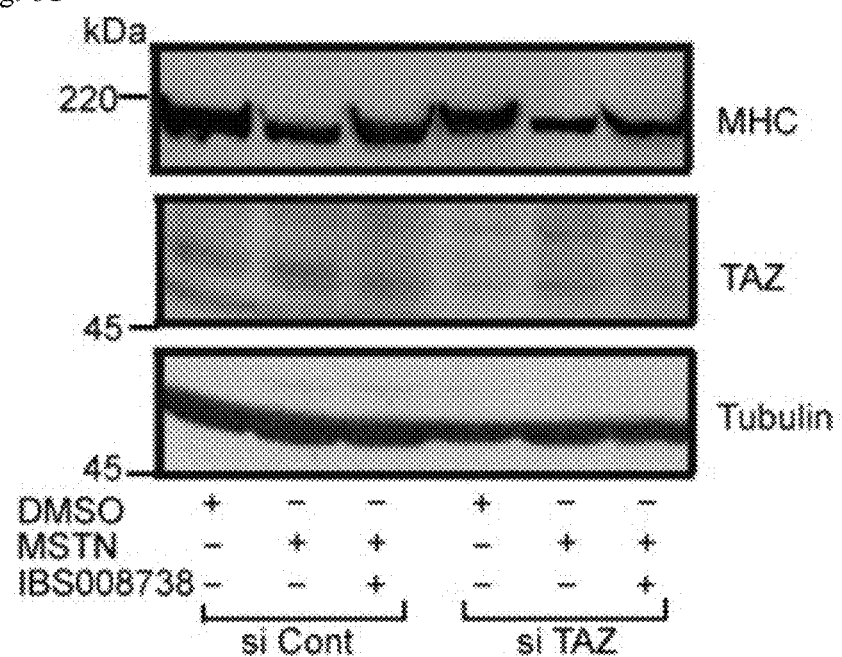
FIG. 8C is a drawing showing the result of evaluation of antagonistic action on myostatin.
Figure 9A:
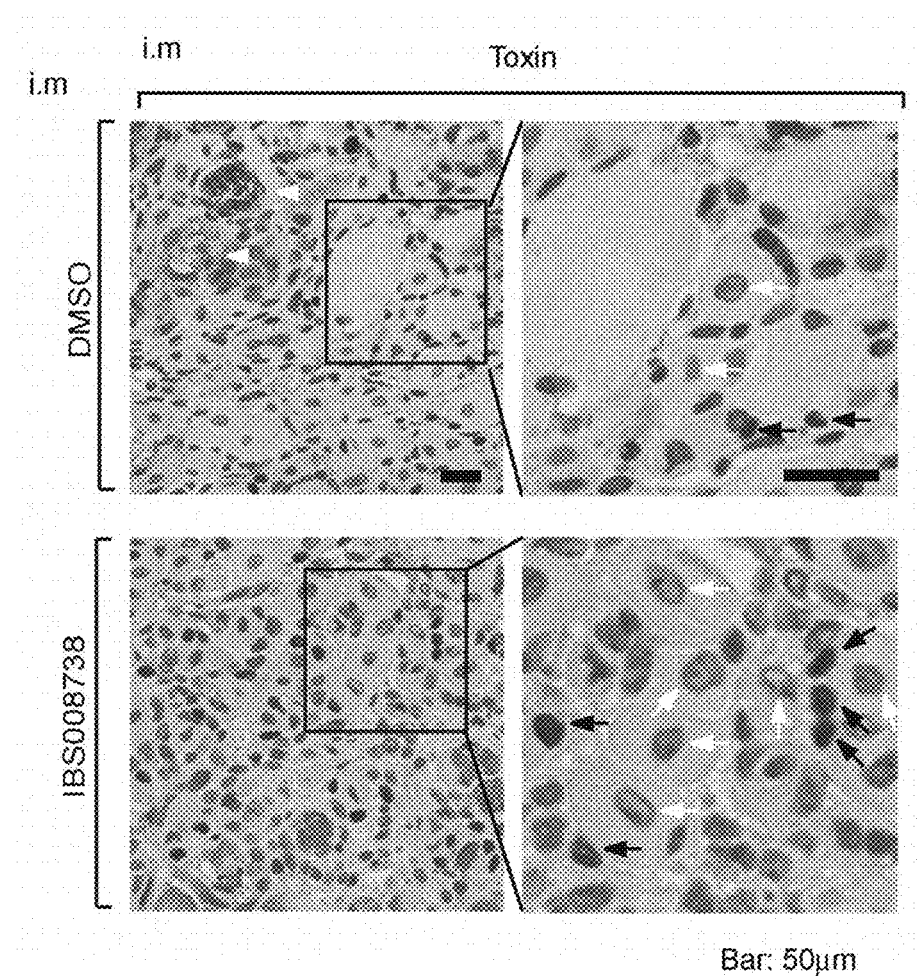
FIG. 9A is a drawing showing the result of evaluation of regeneration of damaged or atrophied muscles.
Figure 9B:
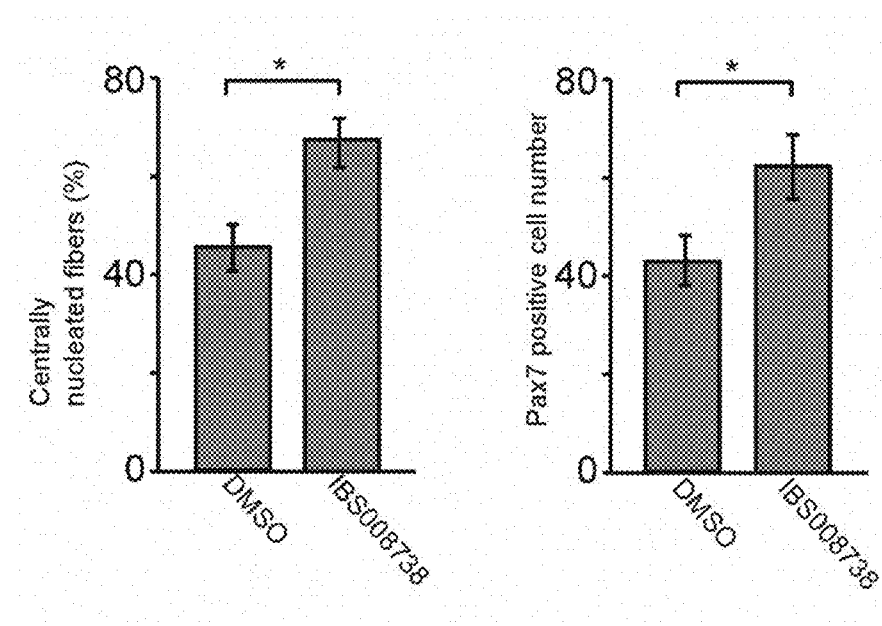
FIG. 9B is a drawing showing the result of evaluation of regeneration of damaged or atrophied muscles.
Figure 9C:
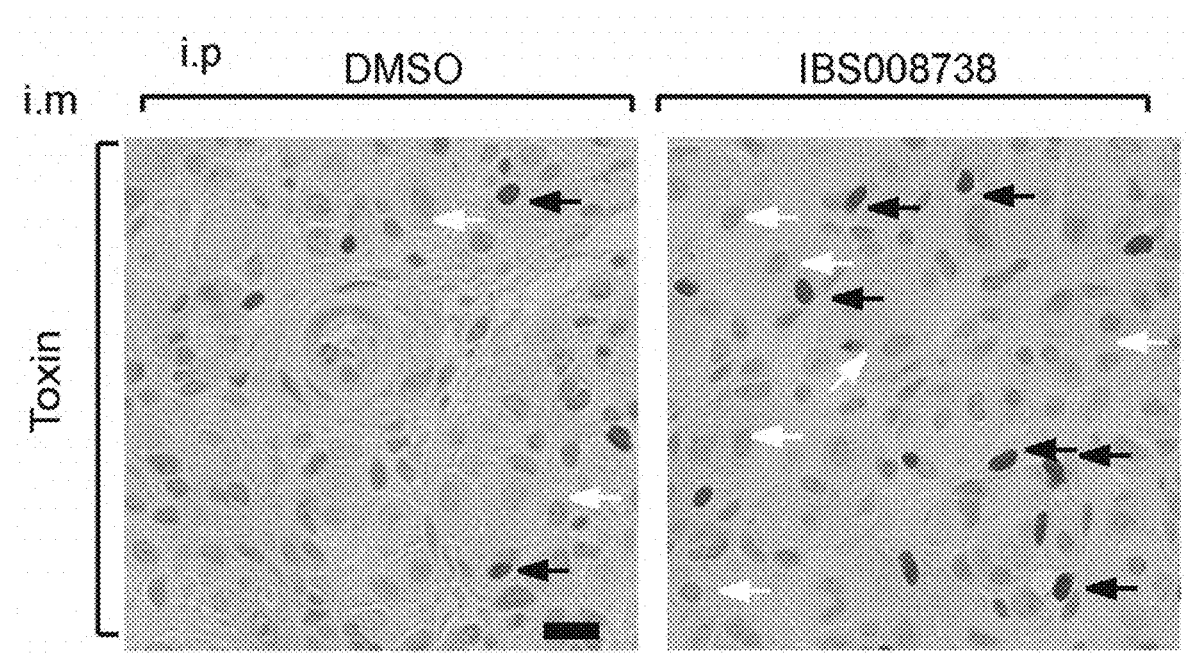
FIG. 9C is a drawing showing the result of evaluation of regeneration of damaged or atrophied muscles.
Figure 9D:
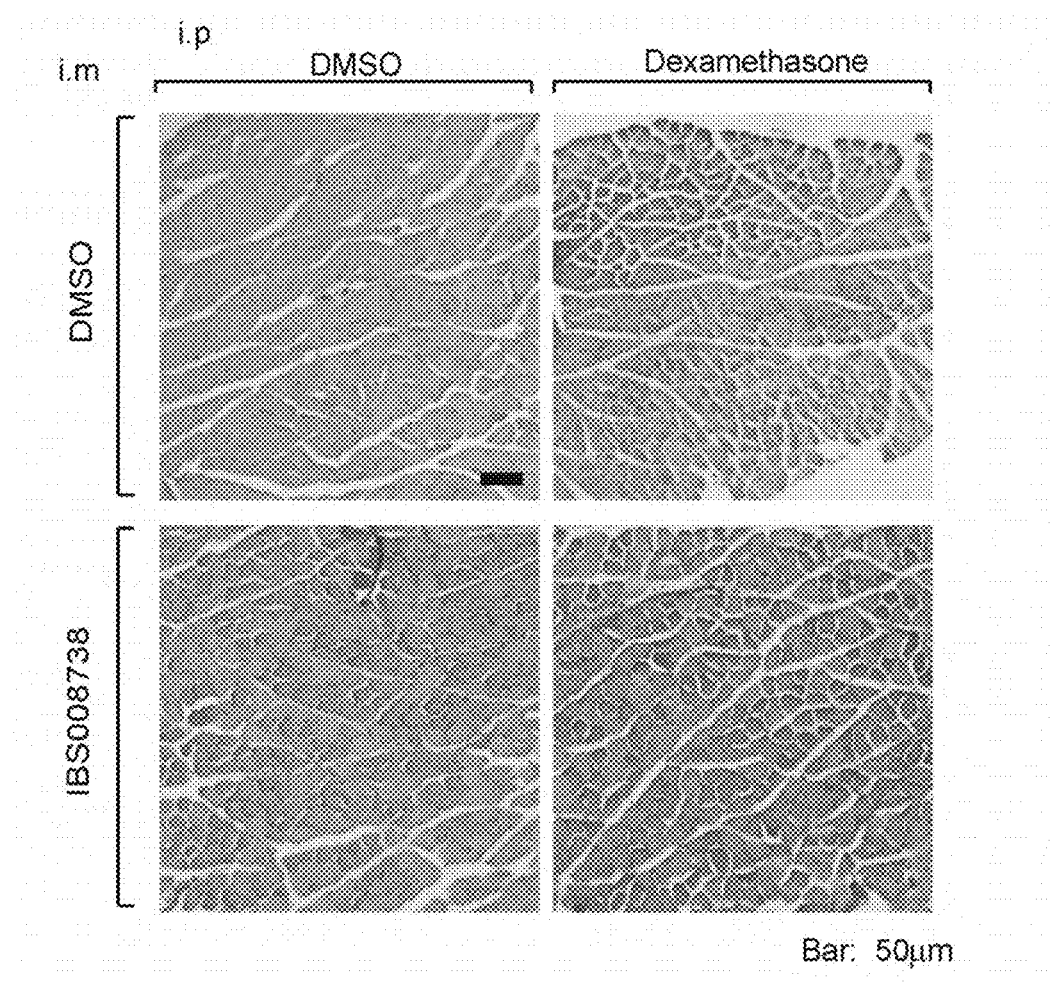
FIG. 9D is a drawing showing the result of evaluation of regeneration of damaged or atrophied muscles.
Figure 9E:
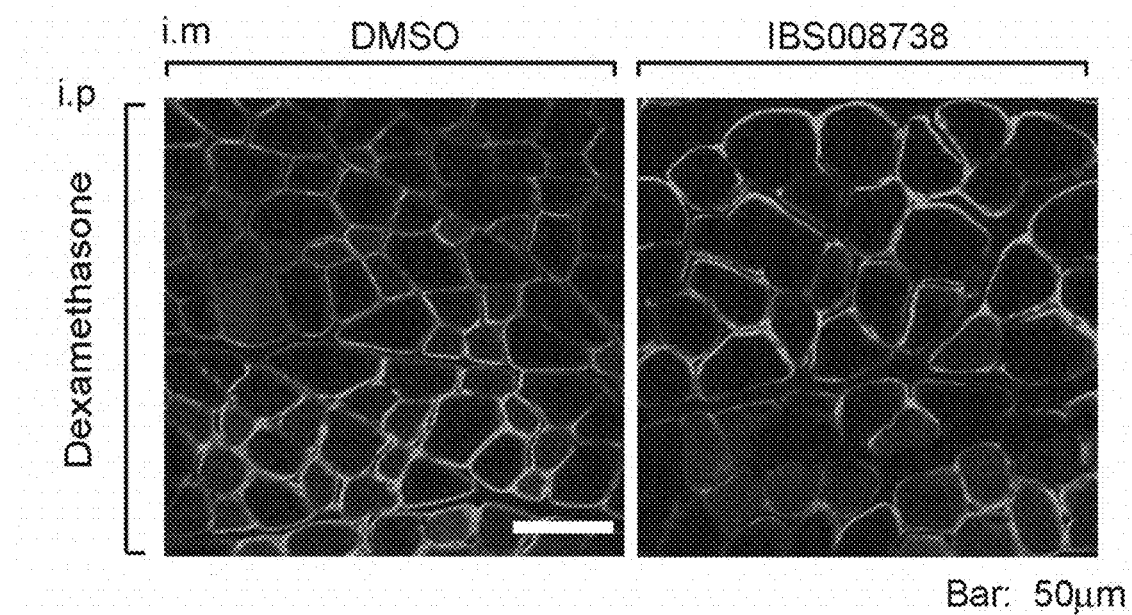
FIG. 9E is a drawing showing the result of evaluation of regeneration of damaged or atrophied muscles.
Figure 9F:
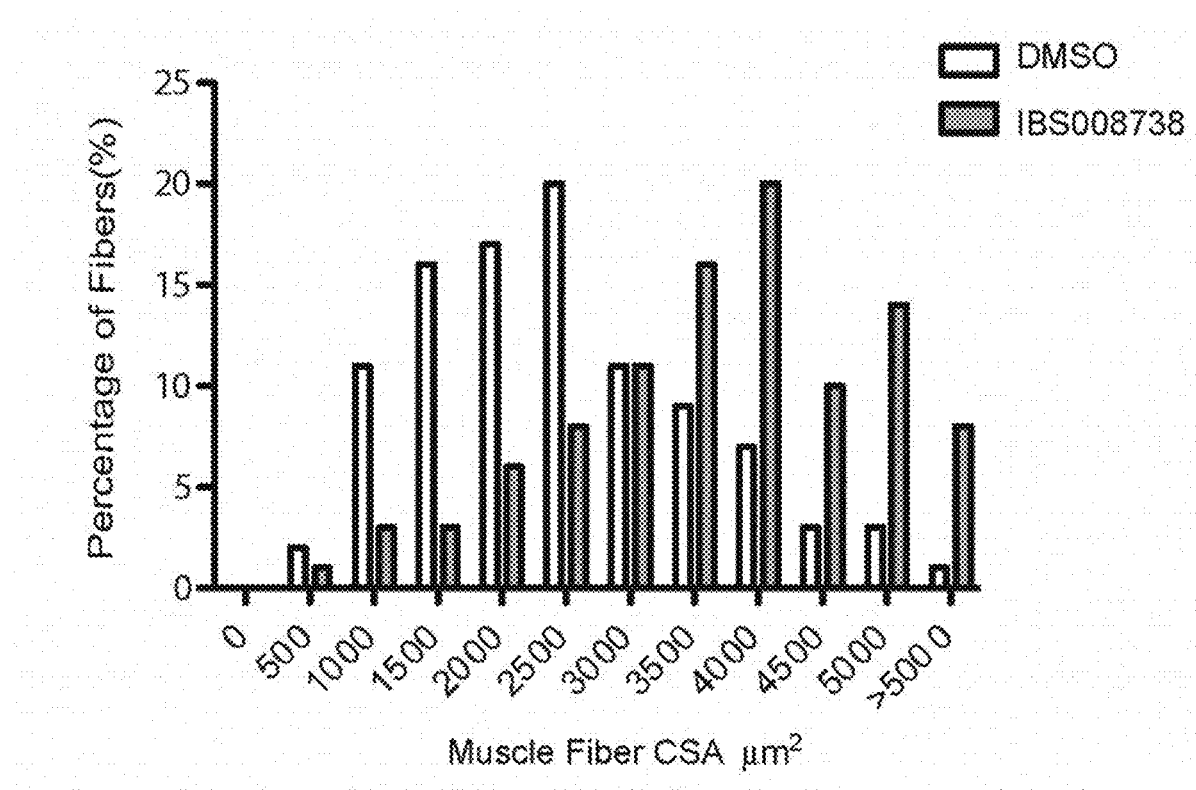
FIG. 9F is a drawing showing the result of evaluation of regeneration of damaged or atrophied muscles.

Myostatin is a protein and a member of a transforming growth factor 13 superfamily, and inhibits muscle growth and differentiation. Myostatin binds activin type IIB receptor and triggers SMAD2/3-dependent signaling. Since TAZ interacts with SMAD2/3, effects of IBS008738 on the signaling of myostatin was examined (FIGS. 8A to 8C). The line in the figures is 100 µm. The line and the error bar indicate the average value and the standard error, *$p<0.05$, *$p<0.01$, *$p<0.001$, ns refers to not significant.

(1) C2C12 cells in which TAZ was knocked down (si TAZ) and C2C12 cells in which TAZ was not knocked down (si Cont) were grown to confluence, respectively, A stock solution of 100 µg/mL myostatin in 4 mM Cl with 0.1% (w/v) BSA and a stock solution of 10 mM IBS008738 in DMSO were prepared. The cells were cultured at differentiation condition for 72 hours in a 1 mL medium with 1 µL DMSO, a 1 mL medium with 1 µL myostatin stock solution, and a 1 mL medium with 1 µL IBS008738 stock solution. As a result, muscle formation of the C2C12 cells was inhibited in the case with only myostatin, but muscle formation of the C2C12 cells was recovered in the case with myostatin and IBS008738. Muscle formation of the C2C12 cells in which TAZ was knocked down did not recover even with the addition of IBS008738 (see FIG. 8A).

(2) The fusion index of C2C12 cells in which TAZ was knocked down (si TAZ) and C2C12 cells in which TAZ was not knocked down (si Cont), after being cultured under differentiation condition for 72 hours, was analyzed. The test was performed three times, and the results are shown in Table 7 and FIG. 8B. The results show that the fusion index of C2C12 cells in which TAZ was not knocked down was significantly increased with the addition of myostatin and IBS008738, as compared with the case in which only myostatin was added. On the other hand, the fusion index of the C2C12 cells in which TAZ was not significantly different between the case with myostatin and IBS008738 and the case with myostatin alone.

TABLE 7

|  |  |  | Fusion index | | |
|---|---|---|---|---|---|
| siCont | DMSO | 1 | 0.13 | 0.12 | 0.15 |
|  | MSTN | 2 | 0.06 | 0.06 | 0.05 |
|  | MSTN + IBS008738 | 3 | 0.16 | 0.14 | 0.16 |
| siTAZ | DMSO | 1 | 0.10 | 0.07 | 0.08 |
|  | MSTN | 2 | 0.02 | 0.03 | 0.04 |
|  | MSTN + IBS008738 | 3 | 0.03 | 0.03 | 0.06 |

Expression of MHC of C2C12 cells in which TAZ was knocked down (si TAZ) and C2C12 cells in which TAZ was not knocked down (si Cont), after being cultured under differentiation condition for 72 hours, was analyzed by immunoblotting. As a result, expression of MHC decreased in the case with only myostatin, whereas it recovered in the case with myostatin and IBS008738 (see FIG. 8C).

<Recovery of Cardiotoxin-Induced Muscle Damage>

Experiments were conducted with mice according to procedures approved by the Institutional Animal Case and Use Committee (see FIG. 9A to 9F). For the experiments, Balb/c ByJ mice (6 weeks, female) were used. The bar in the figures is 50 µm. The line and the error bar indicate the average value and the standard error, *$p<0.05$, i.e refers to intramuscular injection, and i.p refers to intraperitoneal injection.

(1) Cardiotoxin was diluted to 10 µM with phosphate buffered saline (PBS). The cardiotoxin solution (100 µl) was added with 0.3 µL of DMSO, or 0.3 µL of 10 mM IBS008738 stock solution in DMSO, respectively, and the solution was injected to the anterior tibial muscles on the right and the left, respectively. Three mice were used for one experiment, and the experiment was performed twice. The mice were sacrificed at day 5.

(2) On day 1, a PBS solution with 10 µM cardiotoxin (100 µl) and a vehicle (100 µl PBS) were injected in anterior tibial muscles on the right and the left of six mice, respectively. A 100 mM IBS008738 stock solution in DMSO was prepared. On days 2, 4 and 6, three of the mice were intraperitoneally injected with 25 µM of DMSO, and three of the mice were intraperitoneally injected with the IBS008738 stock solution. The mice were sacrificed at day 7.

(3) Observation of muscle tissues was performed by fixing the anterior tibial muscle with 4% formalin and embedding the same in paraffin or O.C.T. compound, and staining muscle sections of 5 µm with haematoxylin and eosin. Further, Pax 7 was detected with anti-Pax 7 antibody and visualized with 3,3'-diaminobenzidine. As a result, the number of Pax7-positive cells, which indicate muscle recovery (shown by black arrows in FIG. 9A), and the number of centrally nucleated muscle fibers (shown by white arrows in FIG. 9A) were both greater than the case in which DMSO was injected. Further, the number of Pax7-positive cells and the number of centrally nucleated muscle fibers, at arbitrarily selected 9 portions of the muscle tissue, were greater in the case in which IBS008738 was injected than the case in which DMSO was injected. The number of the Pax7-positive cells and the number of the centrally nucleated muscle fibers were counted at 6 fields at 20-fold magnification. The results are shown in Table 8 and FIG. 9B.

TABLE 8

|  |  | average | sd |
|---|---|---|---|
| Pax7 positive cells (number) | DMSO | 40.56 | 5.09 |
|  | IBS008738 | 59.00 | 5.82 |
| Central nucleated fibers (%) | DMSO | 45.33 | 4.73 |
|  | IBS008738 | 67.00 | 4.58 |

(4) The muscle tissues of the individual to which IBS 008738 or DMSO was intraperitoneally injected were also observed. As a result, the number of the Pax7-positive cells (shown by black arrows in FIG. 9C) and the number of the centrally nucleated muscle fibers (shown by white arrows in FIG. 9C) were greater in the case with IBS008738, as compared to the case with DMSO.

(5) The immunoblotting of Pax7 was performed with Mouse-on-Mouse immunodetection (MOM) kit (Vector Laboratories), an anti-Pax7 antibody, and a secondary biotinylated antibody. Staining with 3,3'-diaminobenzidine (DAB) was performed by washing the section with PBS, incubating with ABC reagent (Vector Laboratories) for 30 minutes, again washing with PBS, and incubating with DAB. The cell nuclei were conterstained with hematoxylin.

<Suppression of Dexamethasone-Induced Muscle Atrophy>

(1) A 25 mg/mL dexamethasone stock solution in DMSO was prepared. Three Balb/c ByJ mice (6 week, female) were intraperitoneally injected with 20 μL of the dexamethasone stock solution, each day for a week. As a control group, three other individuals were injected with 20 μL of DMSO. On day 9, 11 and 13, each group of the mice was injected with a solution prepared by dissolving 0.3 μL of 10 mM IBS008738 stock solution in 100 μL PBS, on one hindlimb muscle, and with 100 μL PBS on the other hindlimb muscle. The mice were sacrificed at day 14, and the muscle tissues were fixed and stained with hematoxylin and eosin (see FIG. 8D). It was observed that the muscle fibers of the mice administered with dexamethasone were shrinked. No significant effect of injecting IBS008738 was observed in the mice intraperitoneally injected with DMSO, but the muscle fibers of the mice intraperitoneally injected with dexamethasone was partly suppressed by the injection of IBS008738.

(2) The cross section of the muscle fibers of the individual intraperitoneally injected with dexamethasone was stained with an anti-laminin antibody and observed. As a result, shrinkage of muscle fibers of the individual injected with IBS008738 at the hindlimb muscle was more suppressed than the individual injected with DMSO at the hindlimb muscle (see FIG. 9E). The cross-section area of muscle fibers (500 per individual) of the three mice was measured. As a result, the area of the individual injected with IBS008738 was greater than the area of the individual injected with DMSO (see FIG. 9F). The cross-section area of muscle fibers was analyzed with Image J software.

<Evaluation of Effect on Localization of TAZ in the Cell>

Figure 10:
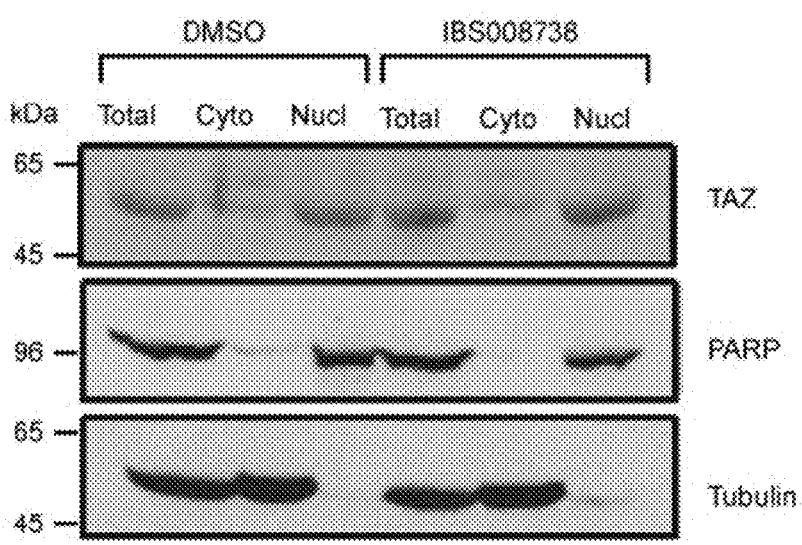
FIG. 10 is a drawing showing the result of evaluation of effects on the localization of TAZ in the cell.

Phosphorylation of TAZ and its localization in the cell are important factors in controlling the activity of TAZ. The localization of TAZ in the cell was examined by performing cell fraction of C2C12 cells after being cultured for 24 hours under differentiation condition in a medium added with IBS008738 or DMSO. As a result, TAZ was localized mainly at the cell nucleus, indicating that IBS008738 has no effect on the localization of TAZ in the cell (see FIG. 10).

<Evaluation of Effect on the Proliferation of Cells>

Figure 11:
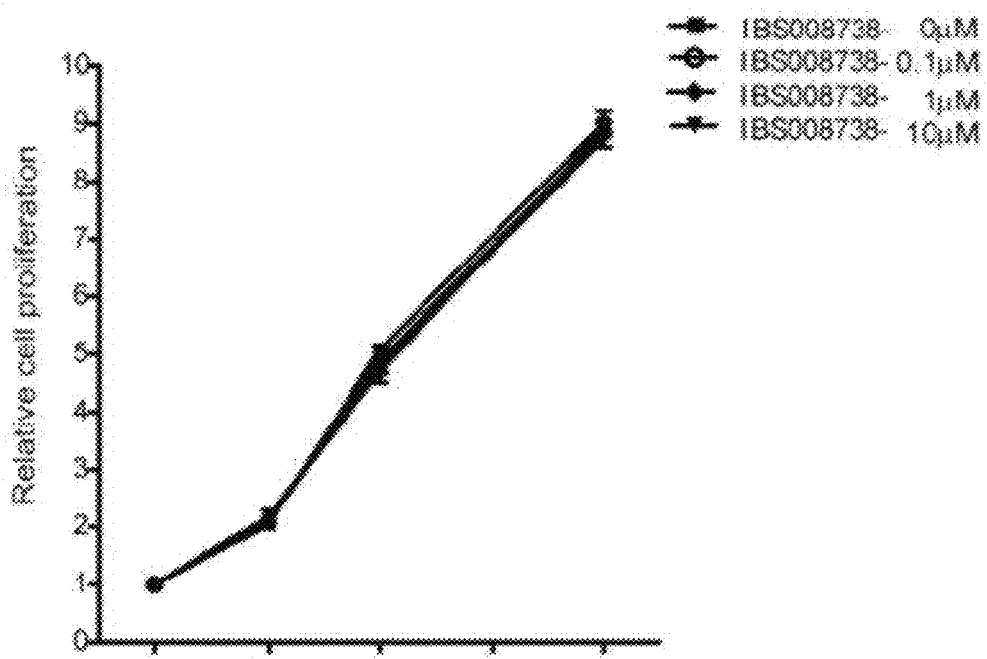
FIG. 11 is a drawing showing the result of evaluation of effects on proliferation of cells.

In order to examine whether IBS008738 as an effect on the proliferation of cells, C2C12 cells were cultured under growth condition for 5 days in a medium added with IBS008738 at 0 μM (not added), 0.1 μM, 1 μM and 10 μM, respectively, and the number of the cells was counted each day by MTT (3-(4, 5-dimethylthiazol-2-yl)-2, 5-diphenyl tetrazolium bromide) method. The counting was performed three times, and the obtained numbers were relativized with the number of day 1 as 1. The results are shown in Table 9 and FIG. 11. The results show that IBS008738 does not have an effect on the proliferation of C2C12 cells.

TABLE 9

|  |  | Relative cell proliferation | | | |
|---|---|---|---|---|---|
|  |  | 24 h | 48 h | 72 h | 120 h |
| 0 μM | 1 | 1.00 | 1.85 | 5.18 | 9.90 |
|  | 2 | 1.00 | 1.94 | 5.14 | 9.65 |
|  | 3 | 1.00 | 1.86 | 4.85 | 9.35 |
| 10 μM | 1 | 1.00 | 2.09 | 4.90 | 8.99 |
|  | 2 | 1.00 | 2.07 | 4.92 | 8.56 |
|  | 3 | 1.00 | 2.09 | 4.70 | 8.63 |
| 1 μM | 1 | 1.00 | 2.41 | 5.11 | 9.13 |
|  | 2 | 1.00 | 2.05 | 4.54 | 8.80 |
|  | 3 | 1.00 | 2.07 | 4.46 | 8.79 |
| 0.1 μM | 1 | 1.00 | 2.09 | 5.37 | 9.01 |
|  | 2 | 1.00 | 2.06 | 4.74 | 8.76 |
|  | 3 | 1.00 | 2.18 | 4.59 | 8.78 |

<Evaluation of Effect on Tumor Formation>

Figure 12A:
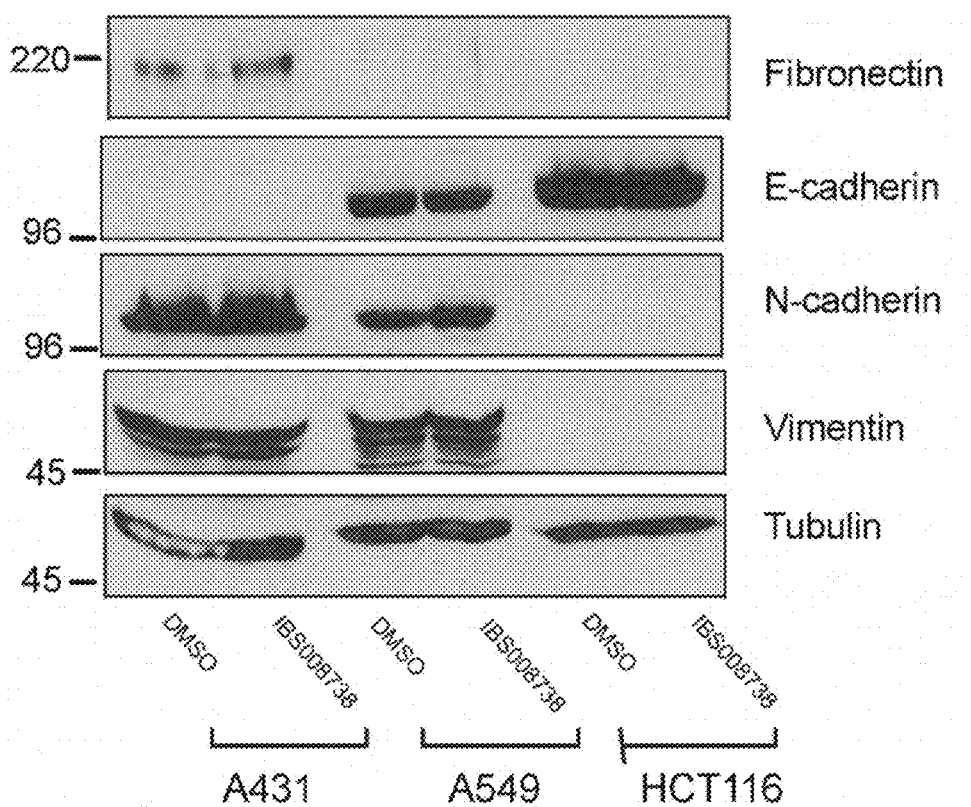
FIG. 12A is a drawing showing the result of evaluation of effects on tumor formation.
Figure 12B:
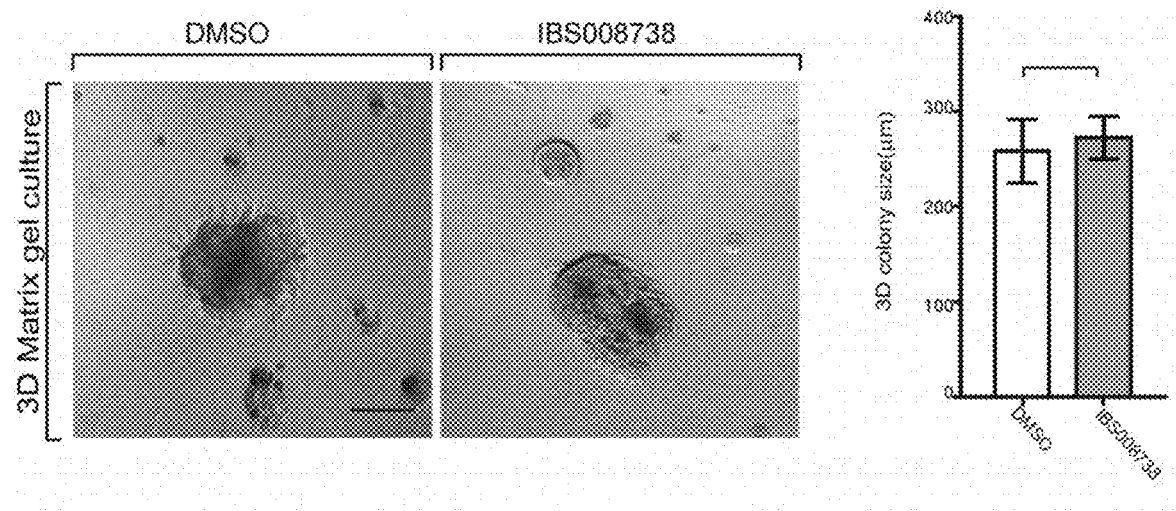
FIG. 12B is a drawing showing the result of evaluation of effects on tumor formation.
Figure 12C:
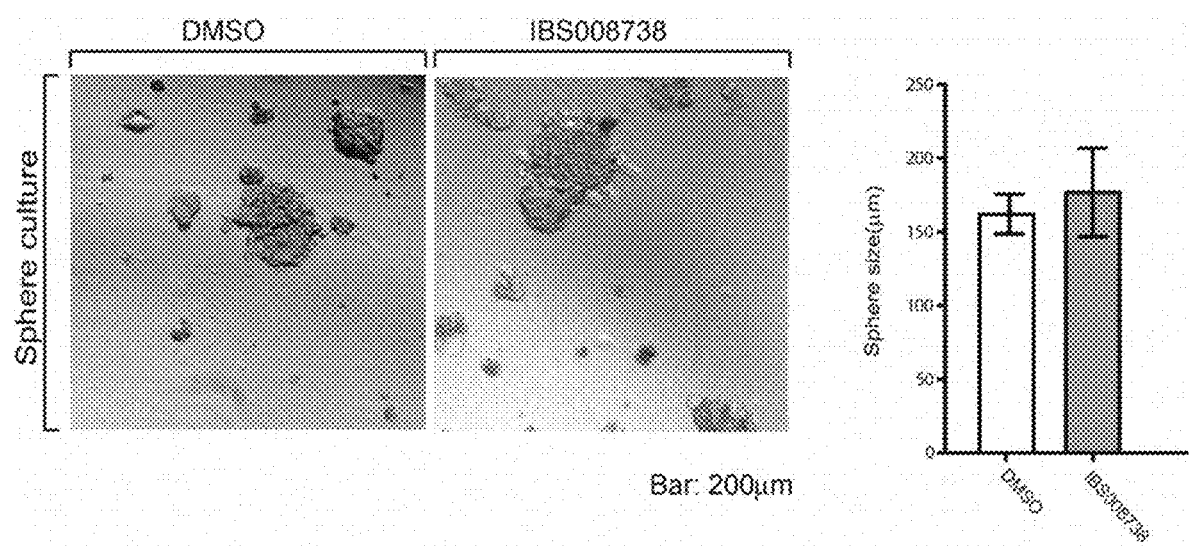
FIG. 12C is a drawing showing the result of evaluation of effects on tumor formation.

TAZ is known also as a carcinogenic gene, and hyperactivity of TAZ is considered to induce epithelial mesenchymal transition (EMT) of cancer cells. Therefore, relationship between IBS008738 and cancer was examined (see FIG. 12A to 12C).

(1) A431 cells, (epidermoid carcinoma), A549 cells (adenocarcinomic human alveolar basal epithelial cell) and HCT116 cells (human colon cancer) were treated with IBS008738 or DMSO, respectively, and evaluated by immunoblotting. As a result, no significant difference was observed between the case treated with IBS08738 and the case treated with DMSO, in any of the markers as an indicator for EMT (fibronectin, E-cadherin, N-cadherin and vimentin) (see FIG. 12A).

(2) Each well of a 96-well plate was pre-coated with 30 μL BD Matrigel (trade name, Becton, Dickinson and Company). A431 cells were suspended in the 2% BD Matrigel at a concentration of $2.1 \times 10^6$ cells/mL. This cell solution (140 μL) was added with 0.17 μL of 10 mM IBS008739 stock solution in DMSO or 0.17 μL of DMSO, and used to layer the pre-coated wells, and proliferation in the 3D matrigel was observed (see FIG. 12B). 300 of A431 cells were placed in each well of Ultra Low Attachment 96-well plate, and cultured in a serum-free DMEM-F-12 medium containing 10 ng/mL FGF, 5 μg/mL insulin and 0.1% (w/v) BSA. Formation of tumor spheres was observed under the condition with 10 mM IBS008739 stock solution dissolved in DMSO so that the final concentration was 10 μM, or the condition with DMSO of the same volume (see FIG. 12C). The maximum diameter of 30 cell aggregates of 150 μm or more observed in the 3D matrigel or sphere formation condition) are measured as the size of 3D colony or sphere. The results are shown in Table 10 and FIGS. 12B and 12C. The line in the figure is 200 μm. The line and the error bar indicate the average value and the standard error, and ns refers to not significant.

TABLE 10

|  |  | average size (μm) | sd |
|---|---|---|---|
| 3D colony size | DMSO | 258.00 | 33.67 |
|  | IBS008738 | 272.30 | 22.77 |
| Sphere size | DMSO | 161.88 | 13.39 |
|  | IBS008738 | 176.63 | 29.99 |

Observation of the spheres and the 3D matrigel cultivation were performed by the following processes. A431, A549 and HCT116 cells were cultured in Ultra Low Attachment 96-well plate (Corning) for 10 days, with a serum-free DMEM/F-12 containing 10 ng/ml basic fibroblast growth factor, 20 ng/ml epidermal growth factor receptor, 5 μg/ml insulin and 0.4% (w/v) BSA (Invitrogen) (300 cells/well). A cell aggregate having a diameter of 150 μm or more was defined as a sphere. For 3D materigel cultivation, a 96-well plate was pre-coated with 30 μl of BD Matrigel per well. In a medium containing 2% BD Matrigel, cells were suspended ($2.1 \times 10^6$ cells/I). Each well was supplied with 140 μL of a suspension containing 300 cells and added with 10 μM DMSO or IBS008738, respectively, and cultured for 10 days.

<DNA Constructions and Virus Productions>

As vectors, pLenti-EF-ires-blast, pClneoFH and pClneoHA, described in J Biochem 150:199-208, Sci Signal 2:ra59, Oncogene 27:4281-4292, were used as vectors.

A TAZ S89A mutant, in which Serine 89 was replaced with alanine, was prepared by PCR using H-2339, 5'-cgctcg-catgcgtcgcccgcgtccctgca-3' and H-2340, 5'-cgggcgacgcatgc-gagcggacatgctggg-3'.

pLenti-EF-FH-TAZ and TAZ SA-ires-blast were prepared by subcloning NheI/SalI fragment from pClneoFH-TAZ and pClneoFH-TAZ SA to pLenti-EF-ires-blast vector.

For the preparation of knockout constructs for human LATS1 and human LATS2, BLOCK-iT (trade name) Pol II miR RNAi Expression Vector Kit (Invitrogen) was used. The target sequence were 1074 bp site of AF104413.1 (LATS1) and 1598 bp site of AF207547.1 (LATS2).

The annealing oligos were ligated into pcDNA 6.2-GW/miR vector according to the manufacturer's protocol to generate pcDNA 6.2 LATS1 KD and pcDNA 6.2 LATS2 KD. BamHI/XhoI fragment was isolated from pcDNA 6.2 LATS2 KD and ligated into BglII/XhoI sites of pcDNA 6.2 LATS1 KD to generate pcDNA 6.2 LATS1/2 KD.

PCR was performed on pBudCE with the primers (H1674, 5'-atcgatgtcgagctagcttcgtgag-3' and H1675, 5'-act-agtctcgagaccacgtgttcacgacacc-3') to amplify elongation factor (EF) promoter. The PCR product was digested with ClaI and SpeI and ligated into the same sites of pLenti4/TO/V5-DEST to replace pCMV/VO promoter with EF promoter and to generate pLenti4-EF/V5-DEST.

pLenti-EmGFP LATS1/2 KD vector was generated by using ViraPower™ T-Rex™ Lentiviral Expression System from pcDNA 6.2 LATS1/2 KD and pLenti4-EF/V5-DEST.

NheI/NotI fragment from pBuCE4.1 was ligated into XbaI/NotI sites of pQCXIP (Clontech) to generate pQCXIP EF.

The linker (H3142, 5'-ggccgctcgagtttaaacaattggatcc-3' and H-3143, 5'-aattggatccaattgtttaaactcgagc-3') was subcloned into NotI/EcoRI sites to generate pQCXIP EF H3142/H3143.

BglII/NotI fragment from pClneomCherry was ligated into BglII/NotI sites of pQCXIP EF H3142/H3143 to generate pQCXIP mCherry, which was digested by BamHI/EcoRV, filled in, and religated to remove IRES-puromycin. The resulting vector was named pQCXI mCherry.

pLenti-siRNA-GFP (Applied Biological Materials Inc.) was digested with SpeI/MluI. The isolated GFP-2A-puro fragment was subcloned into NheI/MluI sites of pClneo (Promega) to generate pClneo GFP-2A-puro, which was subsequently digested with BglI/MluI. The isolated fragment was ligated into BglII/MluI of pQCXI mCherry to generate pQCXI GFP2A-puromycin.

WWTR1 mouse pRFP-RS shRNA (TF505533, 561750) was purchased from OriGene. PCR was performed using the primers (H3163, 5'-caattgaattccccagtggaaagacgcgca-3' and H3164, 5'-acgcgtctcgagcctggggactttcacac-3') to amplify U6 promoter and the target sequence. The PCR product was subcloned into TAKN2 vector (BioDynamics Laboratory Inc.) and digested with MluI/NotI. The isolated fragment was ligated into MluI/NotI sites of pQCXI GFP2A-puromycin. The vector was co-transfected with pCL10A-1 retrovirus packaging vector into HEK293 cells to generate retrovirus for mouse TAZ knockdown. Lentivirus was generated as described previously (Genes Cells 14:1369-1381).

Human TAZ and mouse TAZ were knocked down in MCF10A cells and C2C12 cells as described previously (Ikeda M et al., Sci Signal 2:ra59). The double strand (ds) RNAs used are human TAZ (Ambion s24789) and mouse TAZ (Dharmacon siRNA D-041057).

<Antibodies and Reagents>

The following commercial products were used as the antibodies and the reagents.

Mouse anti-TAZ antibody (560235), mouse anti-MyoD antibody (554130), mouse anti-PARP antibody (51-6639GR), mouse anti-fibronectin antibody (610077), mouse anti-E-cadherin antibody (610181), mouse anti-N-cadherin antibody (610921) and Matrigel (BD Pharmingen)

Rabbit anti-myogenin antibody (sc-576), rabbit anti-MyoD antibody (sc-760) and mouse anti-vimentin antibody (sc-6260) (Santa Cruz)

Mouse anti-MHC antibody (MF20), mouse anti-Pax7 antibody, and mouse anti-Pax3 antibody (Developmental Studies Hybridoma Bank, University of Iowa)

Rabbit anti-laminin antibody (L9293), mouse anti-tubulin antibody (T9026), mouse anti-FLAG M2 antibody (F3165), Hoechst 33342, cardiotoxin from Naja mossambica, dexamethasone (C9759), epidermal growth factor (E9644) and insulin (15500) (Sigma-Aldrich)

Basic fibroblast growth factor (064-04541) (Wako Pure Chemical Industries, Ltd.)

Mouse anti-myogenin antibody (ab1835) (Abcam)

Mouse anti-HA antibody (Roche)

Mouse anti-actin antibody (clone 4) (Millipore)

Rabbit anti-TEAD4 antibody (APR38726_P050) (Aviva)

Goat anti-Pax3 antibody (GWB-3AE0a5) (Genway Biotech Inc.)

Recombinant myostatin (788-G8-010) (R&D systems)

HEK293, A431, A549, HCT116, MCF7 and SW480 cells were cultured in Dulbecco's Modified Eagle Medium (DMEM) containing 10% fetal bovine serum (FBS), 10 mM HEPES-NaOH at pH 7.4, 100 U/ml penicillin and 100 mg/l streptomycin under 5% $CO_2$ at 37° C.

MCF10A cells were cultured in DMEM/F12 supplemented with 5% horse serum (Invitrogen), 20 ng/ml EGF, 0.5 μg/ml hydrocortisone, 10 μg/ml insulin, 100 U/ml penicillin and 100 mg/l streptomycin.

MCF10A-TAZ and MCF10A-TAZ SA cells were prepared using lentivirus vectors (pLenti-EF-FH TAZ-ires-blast and pLenti-EF-FH-TAZ SA-ires-blast) with blastcidin selection.

C2C12 cells were passaged in a growth medium (DMEM containing 10% FBS) and differentiated in a differentiation medium (DMEM containing 2% horse serum (Invitrogen)).

C2C12 cells, in which TAZ was stably knocked down, were prepared using pQCXI-GFP-2A-sh mouse TAZ retrovirus.

In order to achieve stable knock down of LATS1 and LATS2 in MCF10A-TAZ cells, the cells were infected with pLenti-EmGFP-LATS1/2 KD lentivirus and GFP positive cells were collected by FACS.

<Statistical Analysis>

Statistical analyses were performed with student's t test for the comparison between two samples, and analysis of variance (ANOVA) with Dunnett's test for the multiple comparison using the Graph Pad Prism 5.0 (GraphPad Software).

The disclosure of Japanese Patent Application No. 2014-022287 is herein incorporated in this specification by reference in its entirety. All publications, patent applications, and technical standards mentioned in this specification are herein incorporated by reference to the same extent as if each individual publication, patent application, or technical standard was specifically and individually indicated to be incorporated by reference.

The invention claimed is:

1. A myogenesis promotor, comprising a compound selected from the following as an active ingredient:

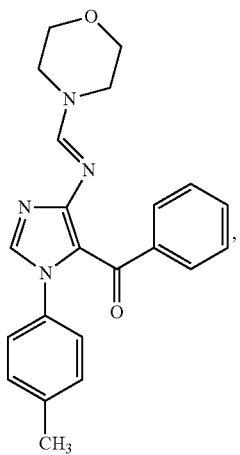

1

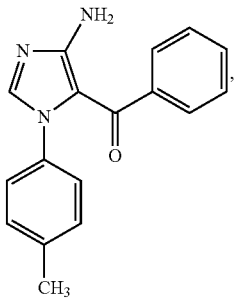

2

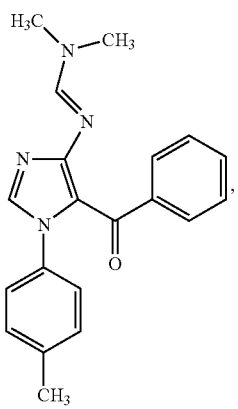

3

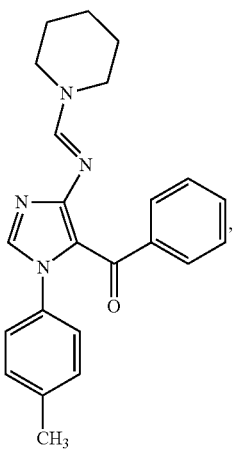
4
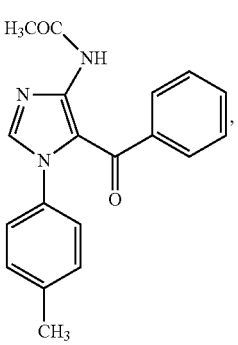
5
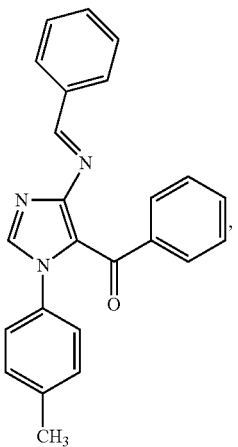
6
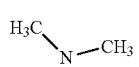
8
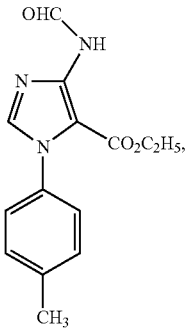
9
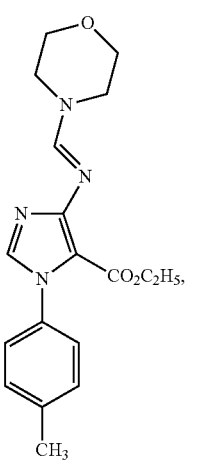
10
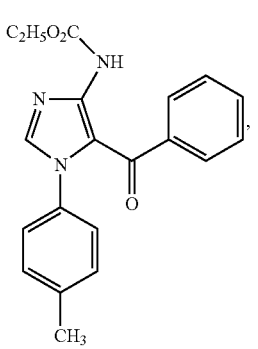
11
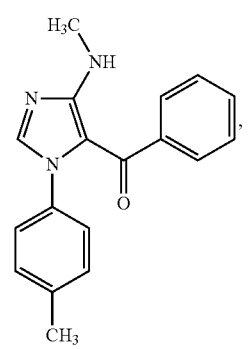
12

14
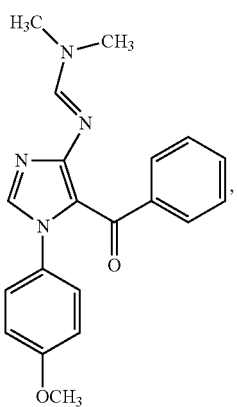
15
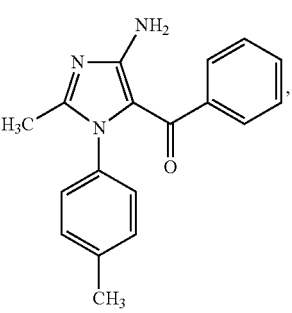
16
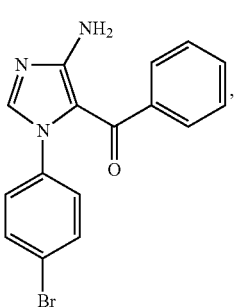
17
18
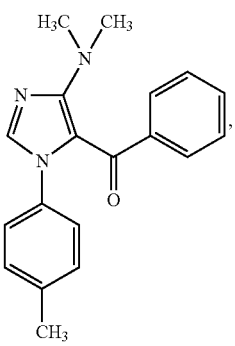
19
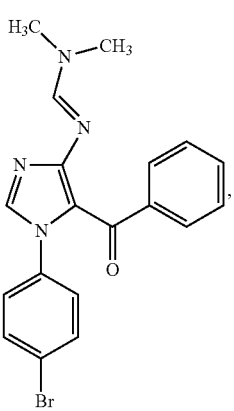
20
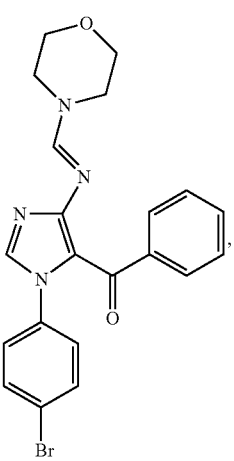
21
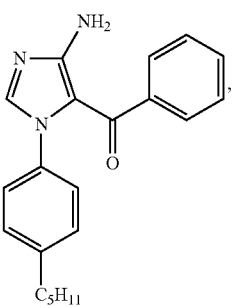

22
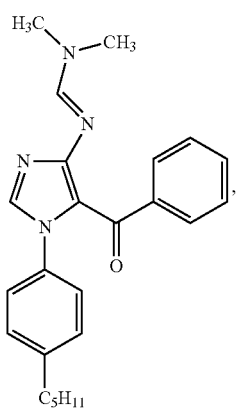
23
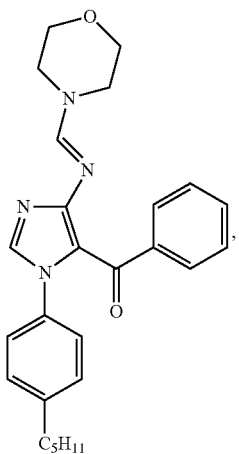
24
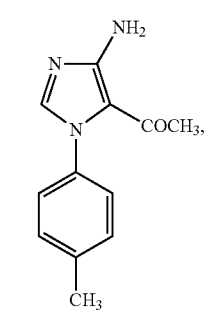
25
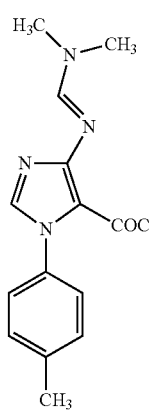
26
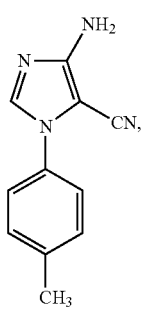
27
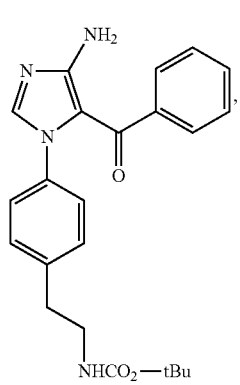
28
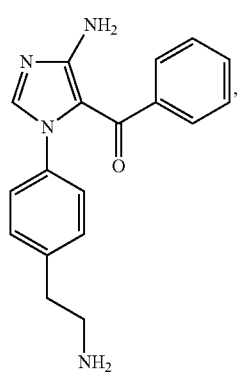
29
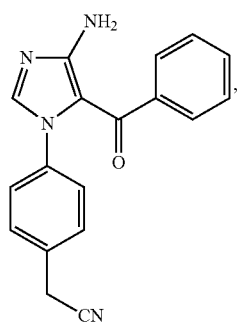

30 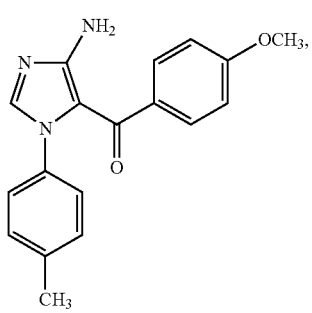
31 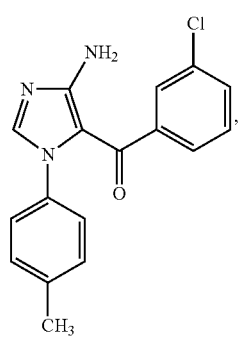
32 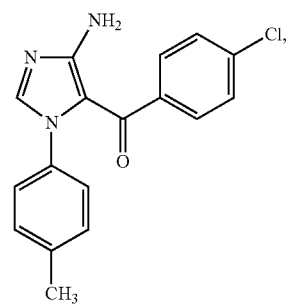
33 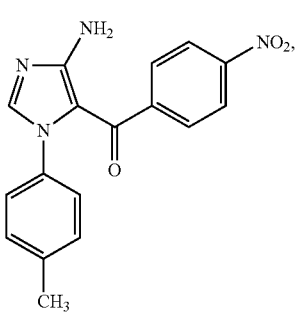
34 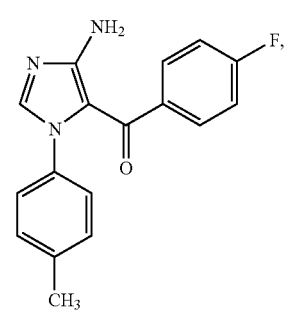
35 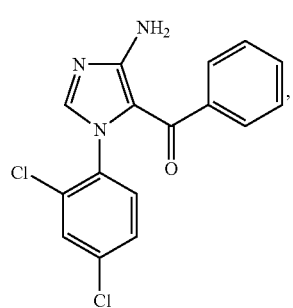
36 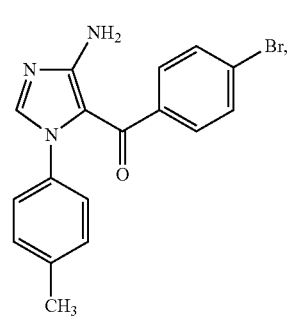
37 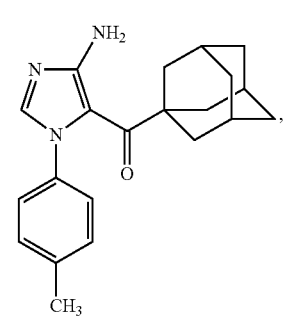
38 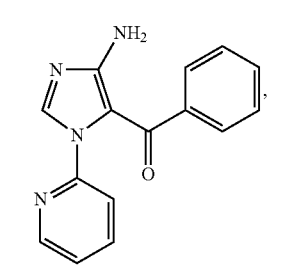
39 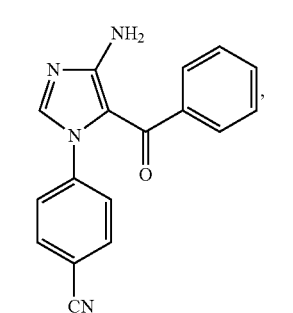

-continued
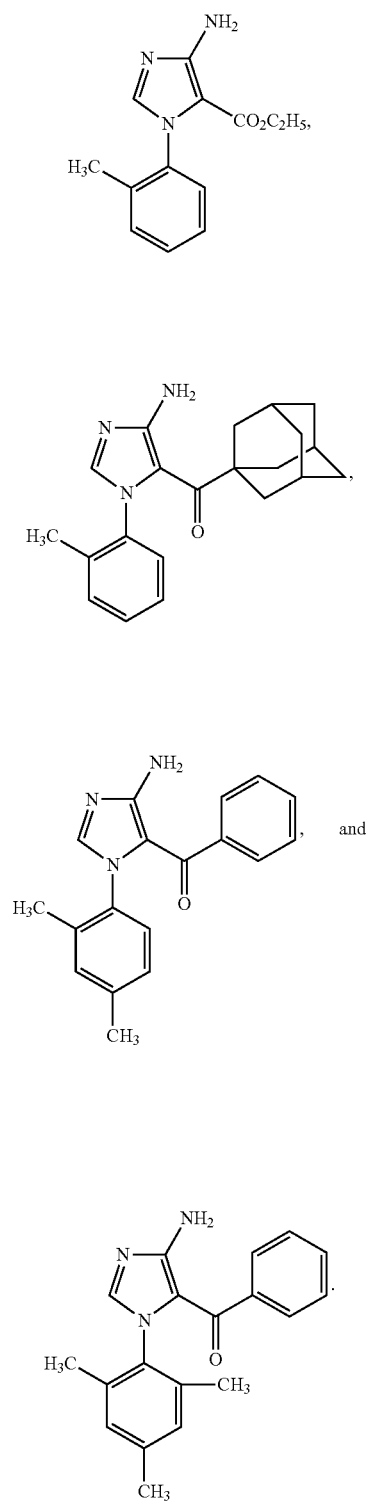
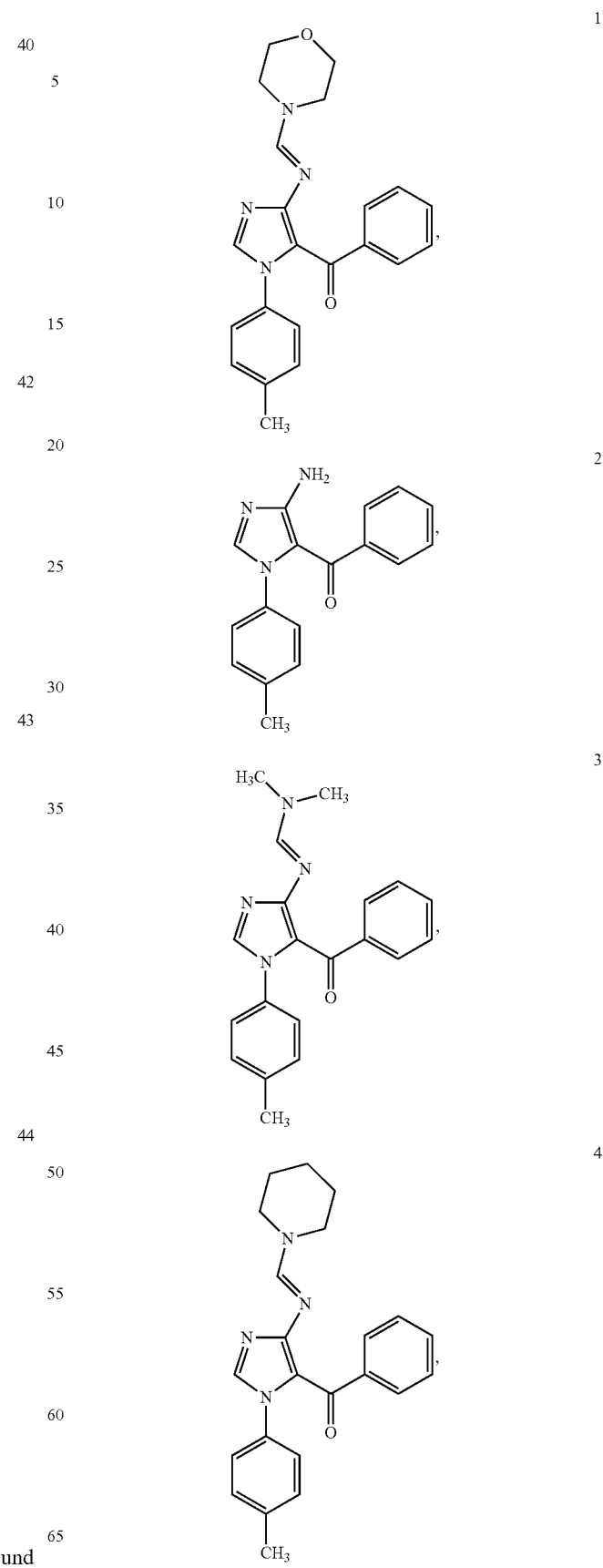
2. A muscle atrophy inhibitor, comprising a compound selected from the following as an active ingredient:

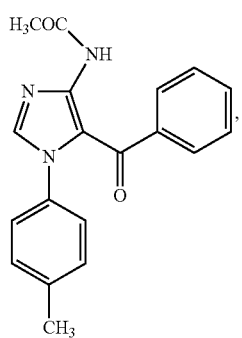
5
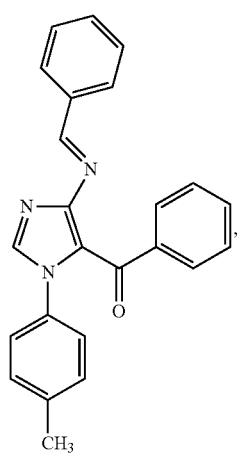
6
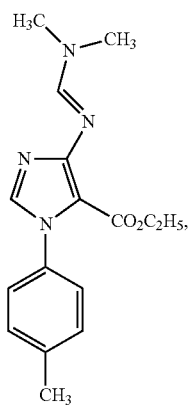
8
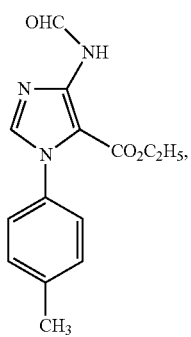
9
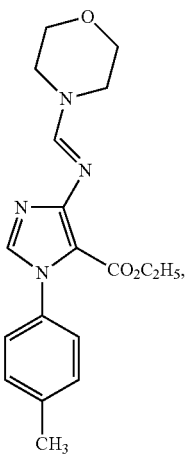
10
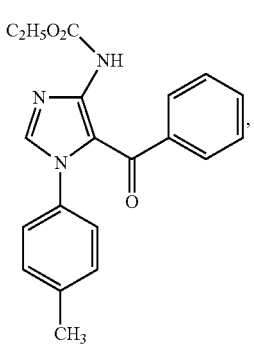
11
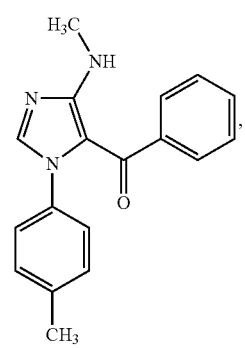
12
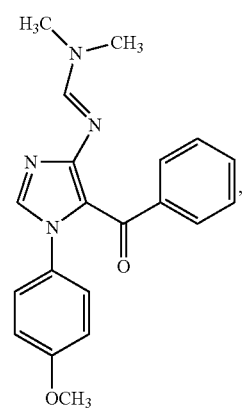
14

-continued
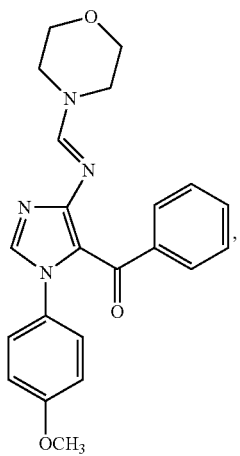
15
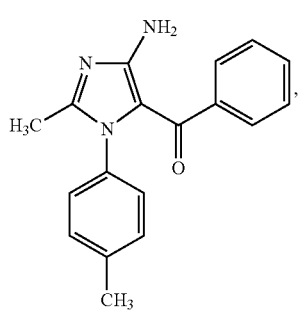
16
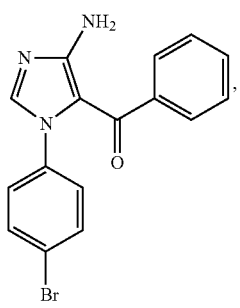
17
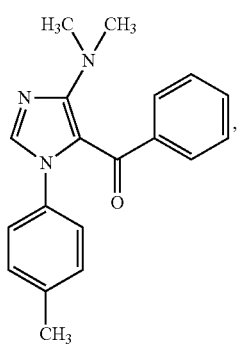
18
-continued
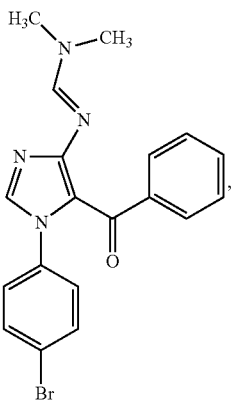
19
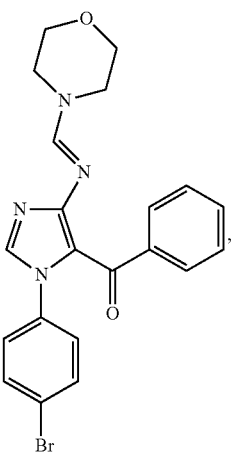
20
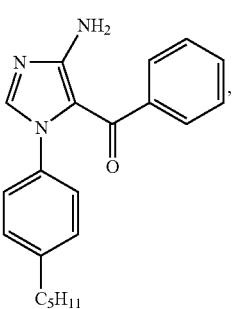
21
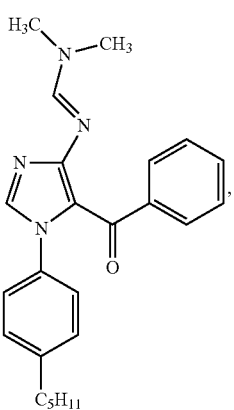
22

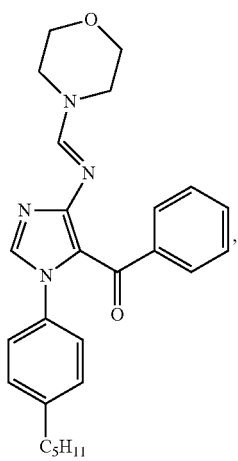
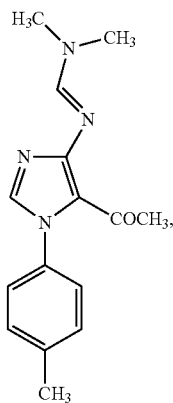
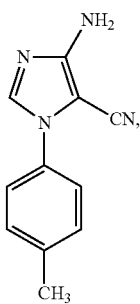
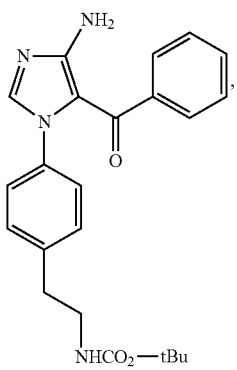
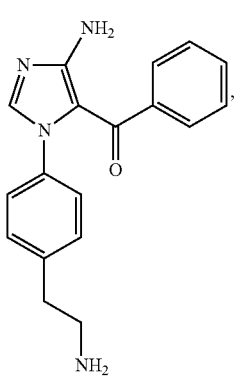
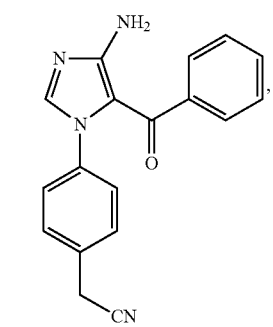
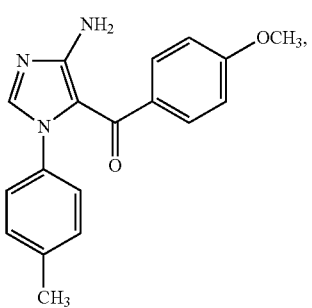

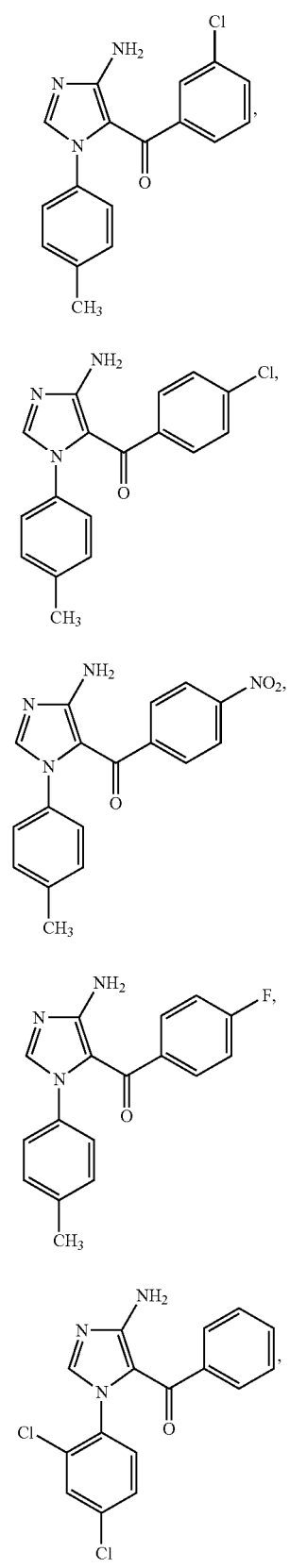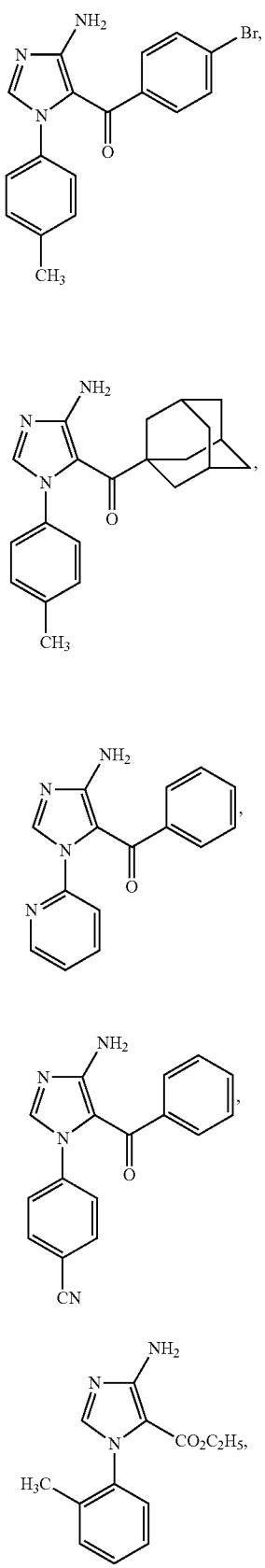

3. A medical composition, comprising a compound selected from the following as an active ingredient:

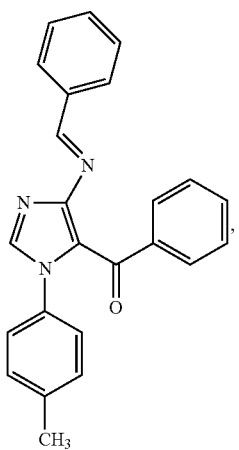
6
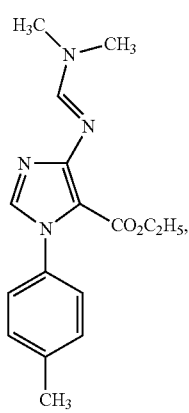
8
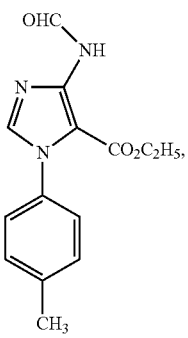
9
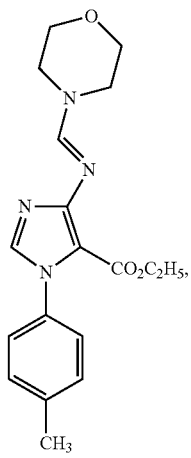
10
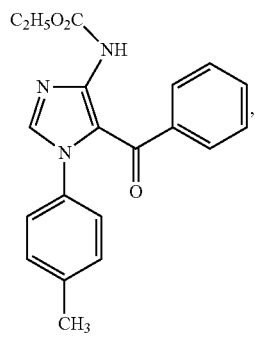
11
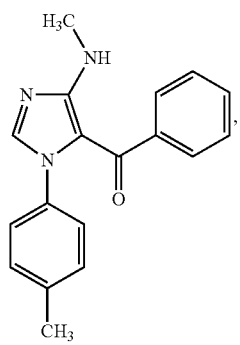
12
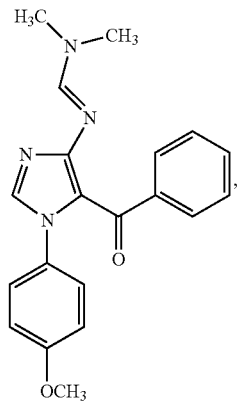
14
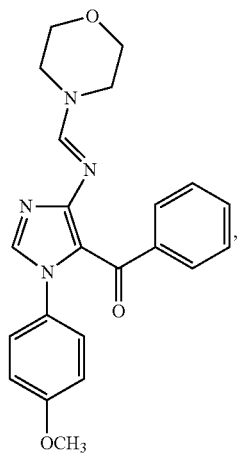
15

16
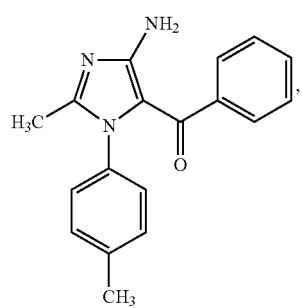
17
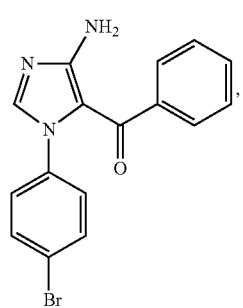
18
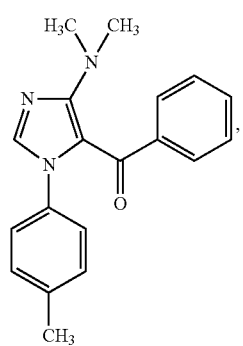
19
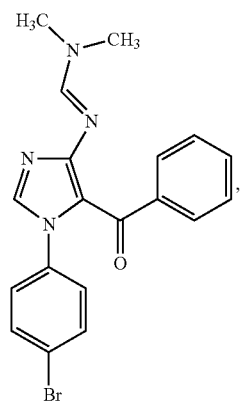
20
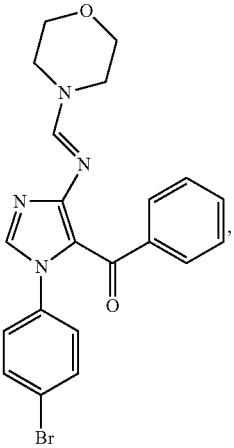
21
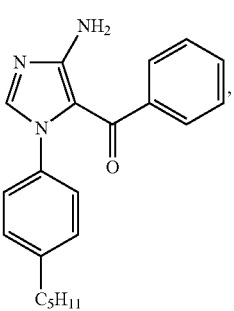
22
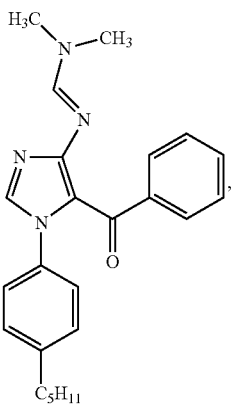
23
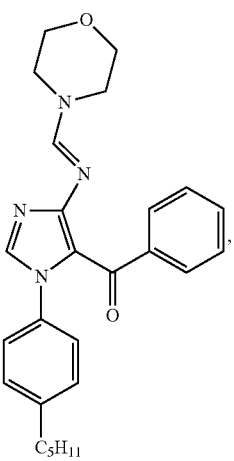

24
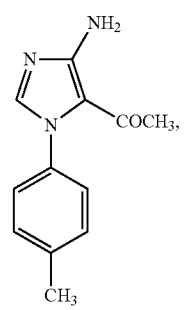
25
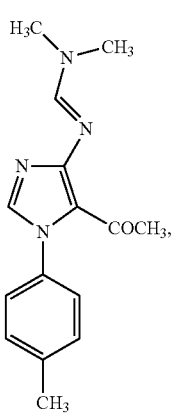
26
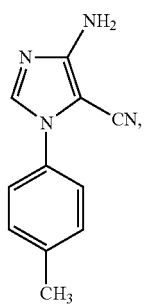
27
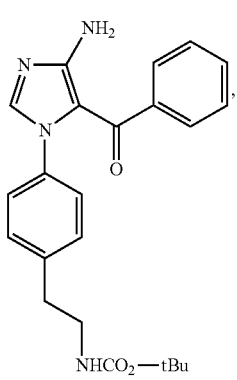
28
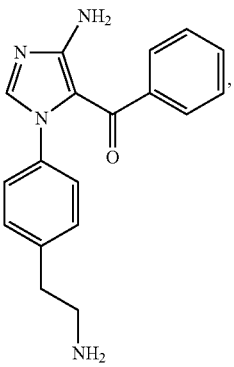
29
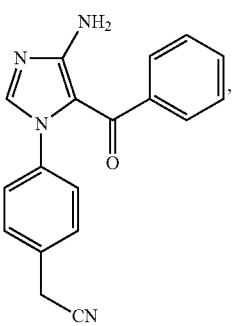
30
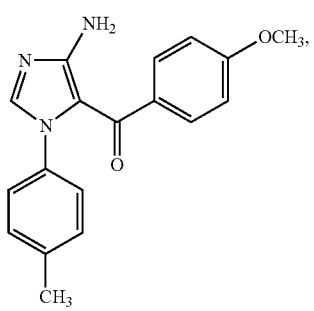
31
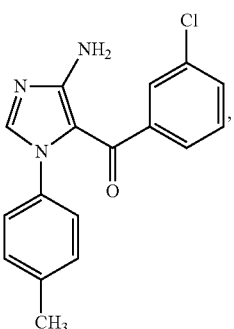
32
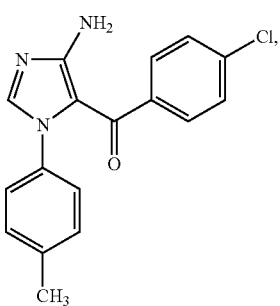

33
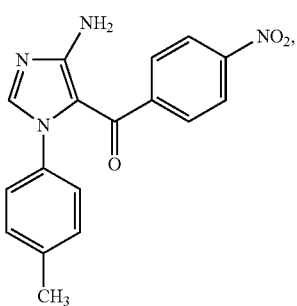
34
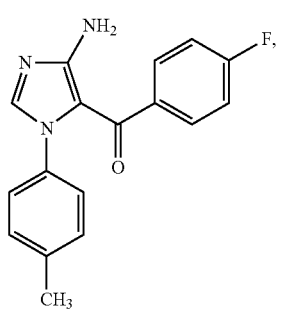
35
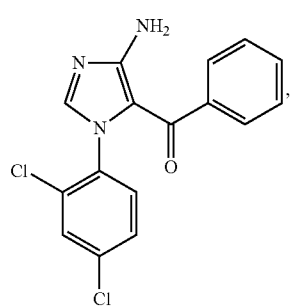
36
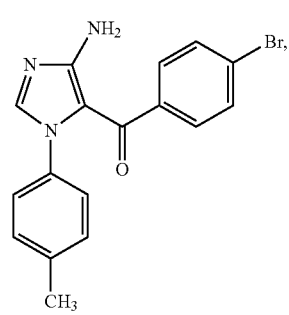
37
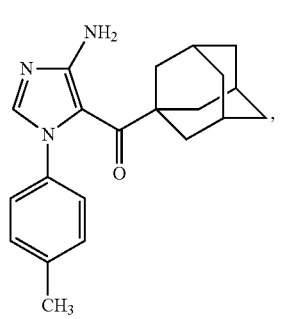
38
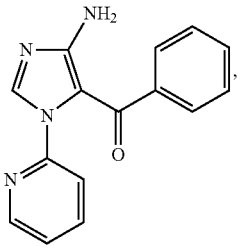
39
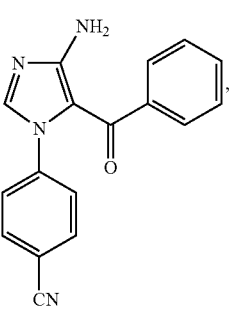
40
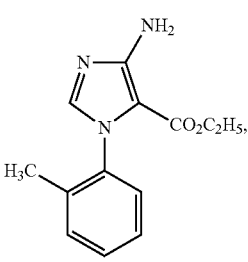
42
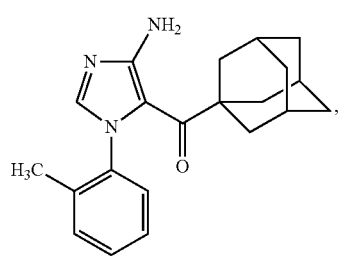
43
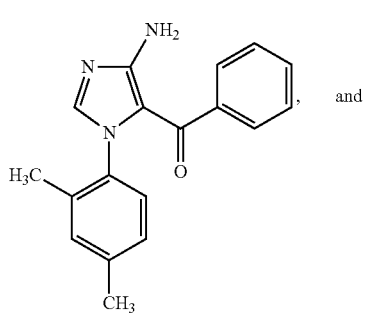
and

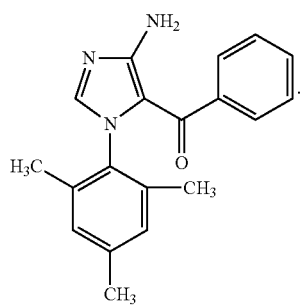
4. A TAZ activator, comprising a compound selected from the following as an active ingredient:
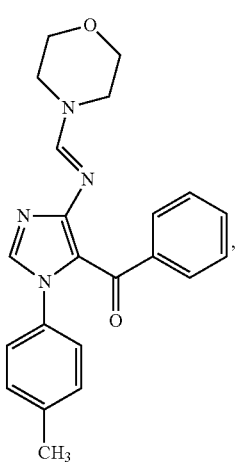
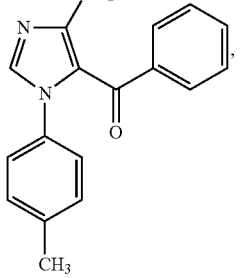
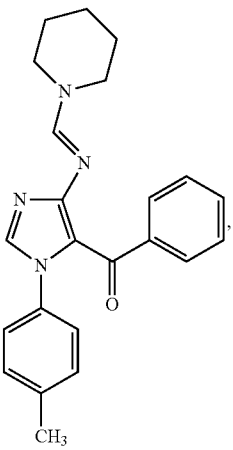
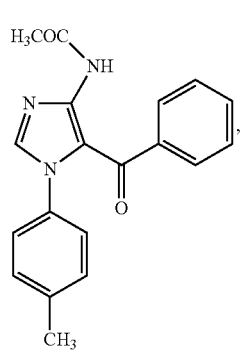
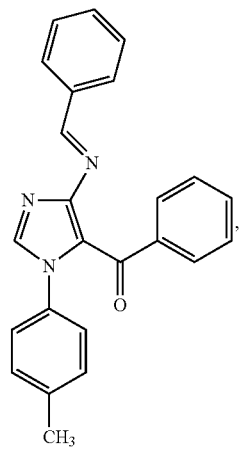
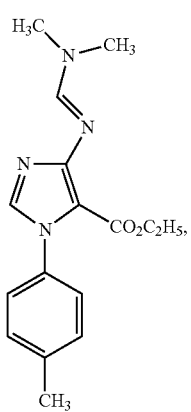

9
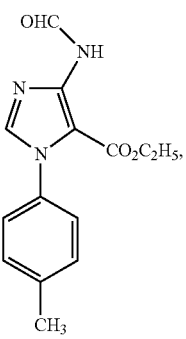
10
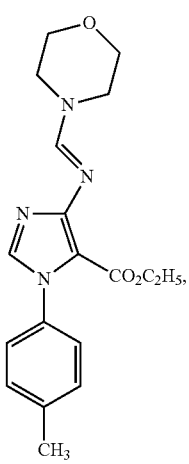
11
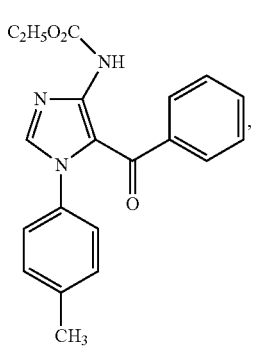
12
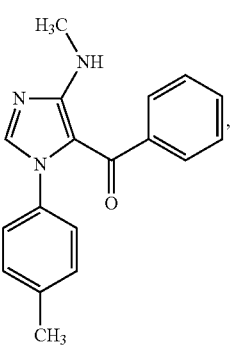
14
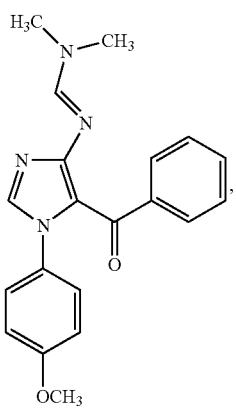
15
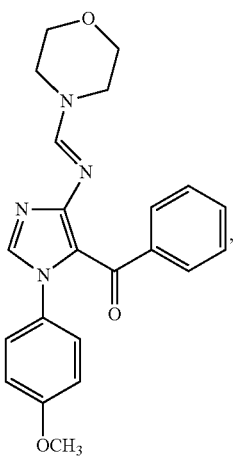
16
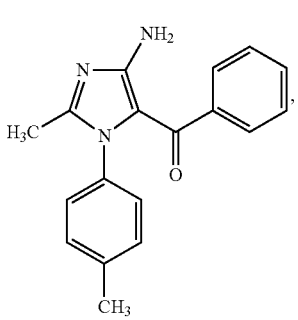
17
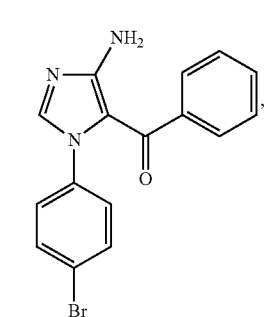

18
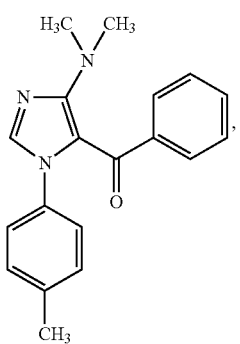
19
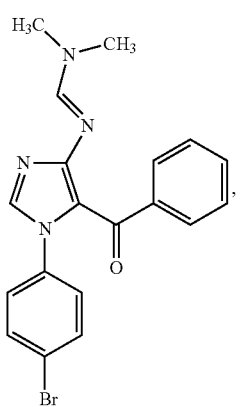
20
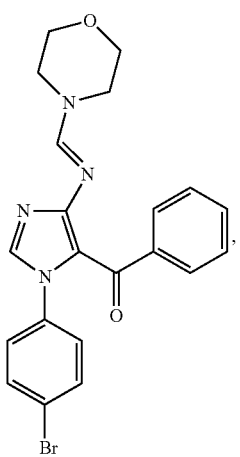
21
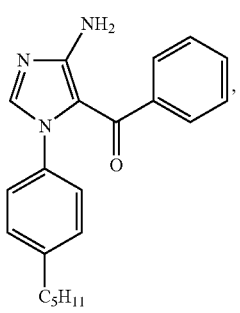
22
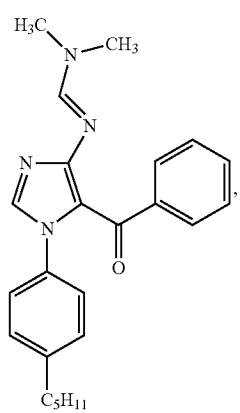
23
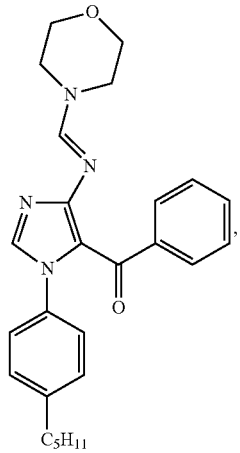
24
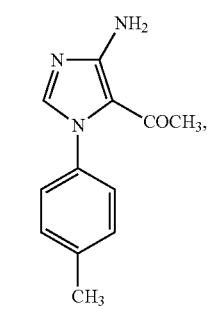
25
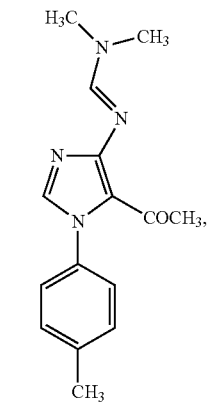

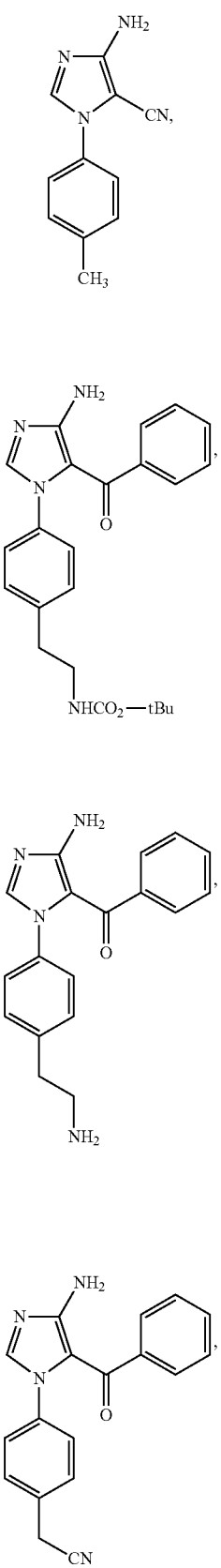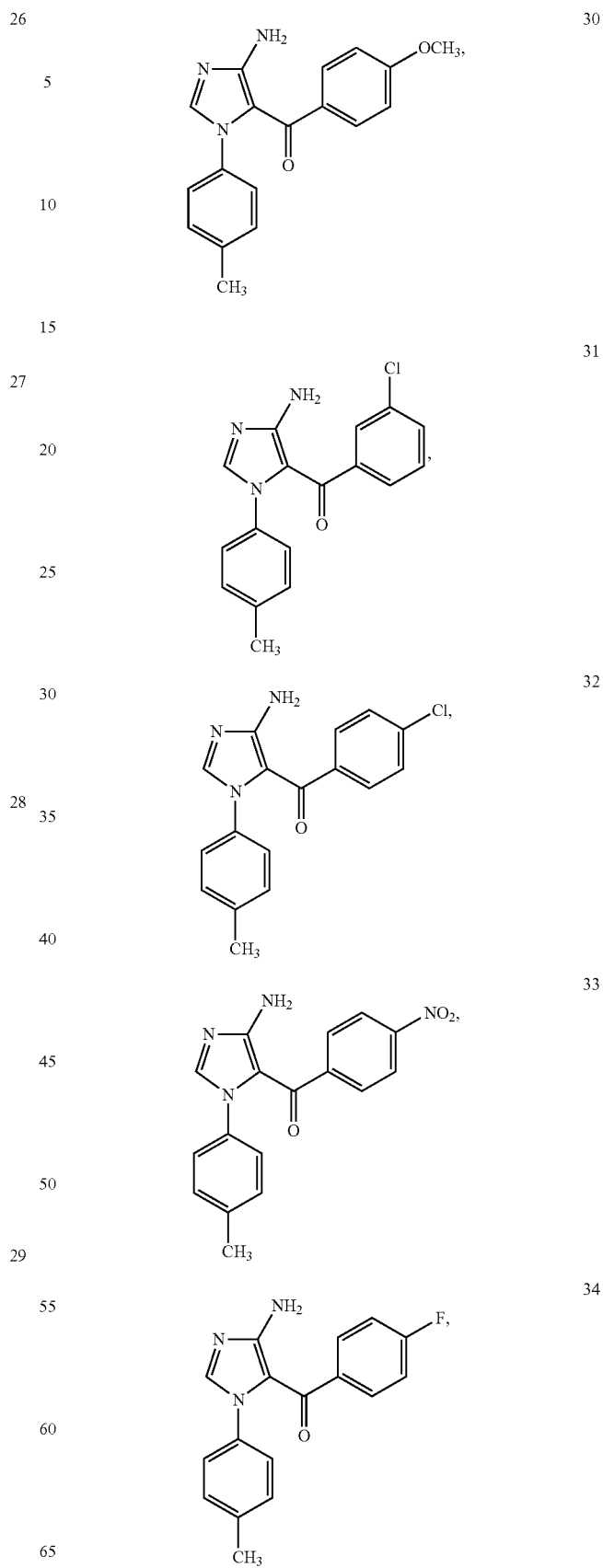

85
-continued
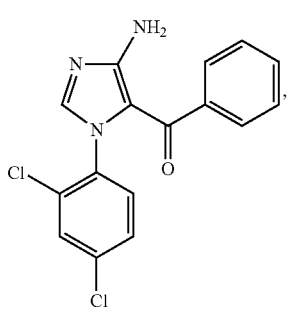
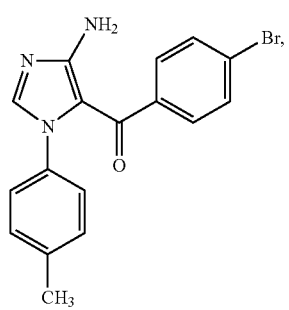
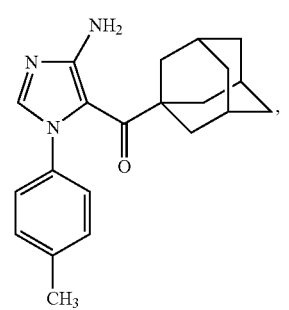
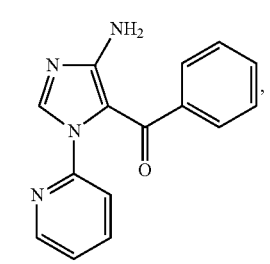
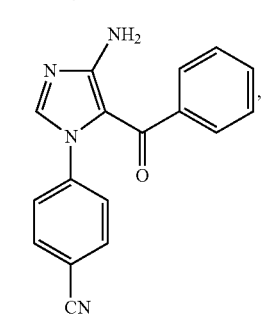
86
-continued
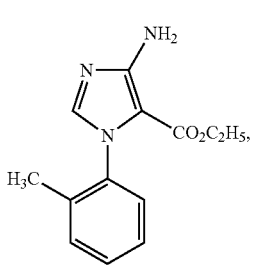
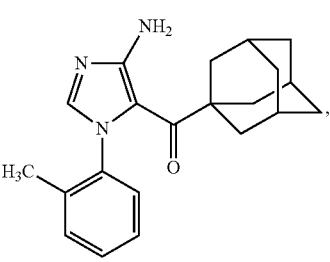
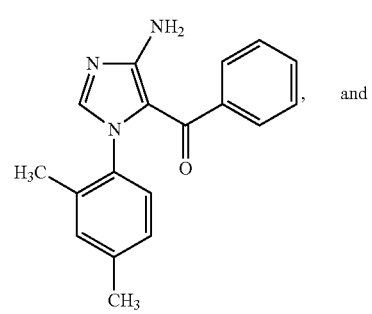
, and
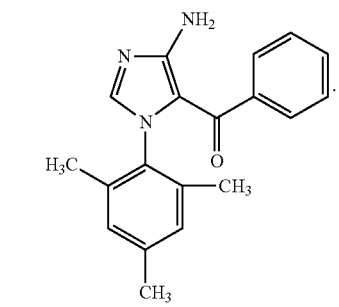
* * * * *

```
                       SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Primer for PCR

<400> SEQUENCE: 1
gtccttcgtg tgggctacat                                            20

<210> SEQ ID NO 2
<211> LENGTH: 20
<212> TYPE: DNA
<213> ORGANISM: Artificial Sequence
<220> FEATURE:
<223> OTHER INFORMATION: Primer for PCR

<400> SEQUENCE: 2
cgaggatctt cggttgacat                                            20

<210> SEQ ID NO 3
<211> LENGTH: 20
<212> TYPE: DNA
<213> ORGANISM: Artificial Sequence
<220> FEATURE:
<223> OTHER INFORMATION: Primer for PCR

<400> SEQUENCE: 3
ttcatccacc gagacatcaa                                            20

<210> SEQ ID NO 4
<211> LENGTH: 20
<212> TYPE: DNA
<213> ORGANISM: Artificial Sequence
<220> FEATURE:
<223> OTHER INFORMATION: Primer for PCR

<400> SEQUENCE: 4
ctccatgctg tcctgtctga                                            20

<210> SEQ ID NO 5
<211> LENGTH: 20
<212> TYPE: DNA
<213> ORGANISM: Artificial Sequence
<220> FEATURE:
<223> OTHER INFORMATION: Primer for PCR

<400> SEQUENCE: 5
ccatggcagt gtcccagccg                                            20
```

<210> SEQ ID NO 6
<211> LENGTH: 20
<212> TYPE: DNA
<213> ORGANISM: Artificial Sequence
<220> FEATURE:
<223> OTHER INFORMATION: Primer for PCR

<400> SEQUENCE: 6
ggcaggcgtg ttgacagggg                                               20

<210> SEQ ID NO 7
<211> LENGTH: 21
<212> TYPE: DNA
<213> ORGANISM: Artificial Sequence
<220> FEATURE:
<223> OTHER INFORMATION: Primer for PCR

<400> SEQUENCE: 7
cgcgacccca agaacatcaa t                                             21

<210> SEQ ID NO 8
<211> LENGTH: 19
<212> TYPE: DNA
<213> ORGANISM: Artificial Sequence
<220> FEATURE:
<223> OTHER INFORMATION: Primer for PCR

<400> SEQUENCE: 8
caccgtcgaa gctgtaggt                                                19

<210> SEQ ID NO 9
<211> LENGTH: 20
<212> TYPE: DNA
<213> ORGANISM: Artificial Sequence
<220> FEATURE:
<223> OTHER INFORMATION: Primer for PCR

<400> SEQUENCE: 9
ggtgaagtgg agtggaaagg                                               20

<210> SEQ ID NO 10
<211> LENGTH: 20
<212> TYPE: DNA
<213> ORGANISM: Artificial Sequence
<220> FEATURE:
<223> OTHER INFORMATION: Primer for PCR

<400> SEQUENCE: 10
tgccctcgta aaatgtggta                                               20

<210> SEQ ID NO 11
<211> LENGTH: 20
<212> TYPE: DNA
<213> ORGANISM: Artificial Sequence
<220> FEATURE:
<223> OTHER INFORMATION: Primer for PCR

<400> SEQUENCE: 11
cccaactaag gggctctctc                                               20

<210> SEQ ID NO 12
<211> LENGTH: 21
<212> TYPE: DNA
<213> ORGANISM: Artificial Sequence
<220> FEATURE:
<223> OTHER INFORMATION: Primer for PCR

<400> SEQUENCE: 12
attctcccac cactcctgac t    21

<210> SEQ ID NO 13
<211> LENGTH: 23
<212> TYPE: DNA
<213> ORGANISM: Artificial Sequence
<220> FEATURE:
<223> OTHER INFORMATION: Primer for PCR

<400> SEQUENCE: 13
tgacctgcag gaaaacatta aga    23

<210> SEQ ID NO 14
<211> LENGTH: 22
<212> TYPE: DNA
<213> ORGANISM: Artificial Sequence
<220> FEATURE:
<223> OTHER INFORMATION: Primer for PCR

<400> SEQUENCE: 14
agccctgtat gtcttcacac tg    22

<210> SEQ ID NO 15
<211> LENGTH: 20
<212> TYPE: DNA
<213> ORGANISM: Artificial Sequence
<220> FEATURE:
<223> OTHER INFORMATION: Primer for PCR

<400> SEQUENCE: 15
agacctgtgc gccctccgta    20

<210> SEQ ID NO 16
<211> LENGTH: 20
<212> TYPE: DNA
<213> ORGANISM: Artificial Sequence
<220> FEATURE:
<223> OTHER INFORMATION: Primer for PCR

<400> SEQUENCE: 16
tttgcagcag ctcctcgggc    20

<210> SEQ ID NO 17
<211> LENGTH: 22
<212> TYPE: DNA
<213> ORGANISM: Artificial Sequence
<220> FEATURE:
<223> OTHER INFORMATION: Primer for PCR

<400> SEQUENCE: 17
actttctgga gccctcctgg ca    22

<210> SEQ ID NO 18
<211> LENGTH: 21
<212> TYPE: DNA
<213> ORGANISM: Artificial Sequence
<220> FEATURE:
<223> OTHER INFORMATION: Primer for PCR

<400> SEQUENCE: 18
tttgttgcac tacacagcat g    21

<210> SEQ ID NO 19
<211> LENGTH: 19

<212> TYPE: DNA
<213> ORGANISM: Artificial Sequence
<220> FEATURE:
<223> OTHER INFORMATION: Primer for PCR

<400> SEQUENCE: 19
tacaggcctt gctcagctc                                                    19

<210> SEQ ID NO 20
<211> LENGTH: 20
<212> TYPE: DNA
<213> ORGANISM: Artificial Sequence
<220> FEATURE:
<223> OTHER INFORMATION: Primer for PCR

<400> SEQUENCE: 20
tgtgggagtt gcattcactg                                                   20

<210> SEQ ID NO 21
<211> LENGTH: 20
<212> TYPE: DNA
<213> ORGANISM: Artificial Sequence
<220> FEATURE:
<223> OTHER INFORMATION: Primer for PCR

<400> SEQUENCE: 21
aactttggca ttgtggaagg                                                   20

<210> SEQ ID NO 22
<211> LENGTH: 20
<212> TYPE: DNA
<213> ORGANISM: Artificial Sequence
<220> FEATURE:
<223> OTHER INFORMATION: Primer for PCR

<400> SEQUENCE: 22
acacattggg ggtaggaaca                                                   20

<210> SEQ ID NO 23
<211> LENGTH: 20
<212> TYPE: DNA
<213> ORGANISM: Artificial Sequence
<220> FEATURE:
<223> OTHER INFORMATION: Primer for PCR

<400> SEQUENCE: 23
cttcttggtg ttgtgctgga                                                   20

<210> SEQ ID NO 24
<211> LENGTH: 20
<212> TYPE: DNA
<213> ORGANISM: Artificial Sequence
<220> FEATURE:
<223> OTHER INFORMATION: Primer for PCR

<400> SEQUENCE: 24
gattgatcct gaccccttga                                                   20

<210> SEQ ID NO 25
<211> LENGTH: 27
<212> TYPE: DNA
<213> ORGANISM: Artificial Sequence
<220> FEATURE:
<223> OTHER INFORMATION: Primer for PCR

```
<400> SEQUENCE: 25
aggcatgact aattgcatgg taactcg                                27

<210> SEQ ID NO 26
<211> LENGTH: 27
<212> TYPE: DNA
<213> ORGANISM: Artificial Sequence
<220> FEATURE:
<223> OTHER INFORMATION: Primer for PCR

<400> SEQUENCE: 26
ctcataatga tatggctttt aagcccc                                27

<210> SEQ ID NO 27
<211> LENGTH: 21
<212> TYPE: DNA
<213> ORGANISM: Artificial Sequence
<220> FEATURE:
<223> OTHER INFORMATION: Primer for PCR

<400> SEQUENCE: 27
aaggagaggg aagggaatc a                                       21

<210> SEQ ID NO 28
<211> LENGTH: 20
<212> TYPE: DNA
<213> ORGANISM: Artificial Sequence
<220> FEATURE:
<223> OTHER INFORMATION: Primer for PCR

<400> SEQUENCE: 28
tagccaacgc cacagaaacc                                        20
```